(12) United States Patent
Bertolotti et al.

(10) Patent No.: US 11,364,211 B2
(45) Date of Patent: Jun. 21, 2022

(54) METHODS FOR SELECTING PHOSPHATASE SELECTIVE AND NON-SELECTIVE PHOSPHATASE INHIBITORS

(71) Applicant: MEDICAL RESEARCH COUNCIL, Swindon (GB)

(72) Inventors: Anne Bertolotti, Cambridge (GB); Indrajit Das, Cambridge (GB); Agnieszka Krzyzosiak, Cambridge (GB); Adrien Rousseau, Cambridge (GB); Kim Schneider, Cambridge (GB); Anna Gudny Sigurdardottir, Cambridge (GB)

(73) Assignee: United Kingdom Research and Innovation, Swindon (GB)

( * ) Notice: Subject to any disclaimer, the term of this patent is extended or adjusted under 35 U.S.C. 154(b) by 0 days.

(21) Appl. No.: 15/564,863

(22) PCT Filed: Apr. 8, 2016

(86) PCT No.: PCT/GB2016/050990
§ 371 (c)(1),
(2) Date: Oct. 6, 2017

(87) PCT Pub. No.: WO2016/162688
PCT Pub. Date: Oct. 13, 2016

(65) Prior Publication Data
US 2018/0125801 A1 May 10, 2018

(30) Foreign Application Priority Data

Apr. 8, 2015 (GB) ..................................... 1505971
Apr. 8, 2015 (GB) ..................................... 1505975

(51) Int. Cl.
| | |
|---|---|
| *A61K 31/155* | (2006.01) |
| *C07C 281/18* | (2006.01) |
| *C07D 213/61* | (2006.01) |
| *A61P 21/00* | (2006.01) |
| *A61P 25/14* | (2006.01) |
| *C12Q 1/42* | (2006.01) |
| *C07D 239/30* | (2006.01) |
| *A61P 25/28* | (2006.01) |
| *G01N 33/573* | (2006.01) |
| *C12N 11/14* | (2006.01) |

(Continued)

(52) U.S. Cl.
CPC ............ *A61K 31/155* (2013.01); *A61P 21/00* (2018.01); *A61P 25/14* (2018.01); *A61P 25/28* (2018.01); *C07C 281/18* (2013.01); *C07D 213/61* (2013.01); *C07D 239/30* (2013.01); *C12N 11/14* (2013.01); *C12Q 1/42* (2013.01); *G01N 21/31* (2013.01); *G01N 33/53* (2013.01); *G01N 33/573* (2013.01); *C07K 2317/92* (2013.01); *G01N 2333/916* (2013.01)

(58) Field of Classification Search
CPC ........ A61K 31/155; A61P 25/14; A61P 21/00; A61P 25/28; C07C 281/18; C07D 213/61; C07D 239/30; C12Q 1/42; G01N 21/31; G01N 33/53; G01N 33/573; G01N 2333/916; C07K 2317/92
See application file for complete search history.

(56) References Cited

U.S. PATENT DOCUMENTS

| | | |
|---|---|---|
| 3,982,020 A | 9/1976 | Houlihan et al. |
| 4,109,008 A | 8/1978 | Cognacq et al. |

(Continued)

FOREIGN PATENT DOCUMENTS

| | | | |
|---|---|---|---|
| DE | 27 00 561 A1 | 7/1977 | |
| EP | 2066312 B1 * | 3/2012 | ........... A61K 31/155 |

(Continued)

OTHER PUBLICATIONS

Abdulkarim, Baroj et al., "A Missense Mutation in PPP1R15B Causes a Syndrome Including Diabetes, Short Stature, and Microcephaly," *Diabetes*, vol. 64, pp. 3951-3962, 2015.

(Continued)

*Primary Examiner* — James D. Anderson
*Assistant Examiner* — William Y Lee
(74) *Attorney, Agent, or Firm* — Bookoff McAndrews, PLLC

(57) ABSTRACT

The present invention discloses a method to discover selective inhibitors of phosphatases. Thus the invention provides a method for screening a test compound to determine whether the compound binds a holophosphatase selectively or non-selectively comprising: i) providing a first holophosphatase wherein said holophosphatase is captured/immobilised; ii) testing a test compound for its ability to bind to the first holophosphatase; iii) providing a second holophosphatase wherein said second holophosphatase is captured/immobilised; iv) testing the same test compound for its ability to bind to the second holophosphatase; v) comparing the binding of the test compound to said first holophosphatase with the binding to said second phosphatase wherein a compound that binds a holophosphatase selectively will bind to said first holophosphatase but not said second holophosphatase; or will bind to said second holophosphatase but not said first; or wherein a compound that binds a holophosphatase non-selectively will bind to both said first holophosphatase and said second holophosphatase.

6 Claims, 19 Drawing Sheets
Specification includes a Sequence Listing.

(51) Int. Cl.
G01N 21/31 (2006.01)
G01N 33/53 (2006.01)

(56) References Cited

U.S. PATENT DOCUMENTS

2005/0136444 A1  6/2005  Scully et al.
2009/0306430 A1  12/2009  Becq et al.
2018/0111896 A1  4/2018  Bertolotti et al.

FOREIGN PATENT DOCUMENTS

| GB | 1223491 A | 2/1971 |
|---|---|---|
| WO | WO 01/25192 A1 | 4/2001 |
| WO | WO 02/11715 A2 | 2/2002 |
| WO | WO 2005/031000 A2 | 4/2005 |
| WO | WO 2007/060342 A2 | 5/2007 |
| WO | WO 2008/041133 A2 | 4/2008 |
| WO | WO 2008/041134 A2 | 4/2008 |
| WO | WO 2014/108520 A1 | 7/2014 |
| WO | WO 2014/138298 | 9/2014 |
| WO | WO 2015/120446 A1 | 8/2015 |
| WO | WO 2016/001389 | 1/2016 |
| WO | WO 2016/001390 | 1/2016 |
| WO | WO 2016/162689 | 10/2016 |

OTHER PUBLICATIONS

Bairwa, R. et al., Novel Molecular Hybrids of Cinnamic Acids and Guanylhydrazones as Potential Antitubercular Agents, *Bioorganic & Medicinal Chem. Lett.*, vol. 20, pp. 1623-1625, 2010.

Berge, Stephen M. et al., "Pharmaceutical Salts," *J. Pharm. Sci.*, vol. 66, pp. 1-19, 1977.

Bertolotti, Anne et al., Dynamic Interaction of BiP and ER Stress Transducers in the Unfolded-Protein Response, *Nature Cell Biology*, vol. 2, pp. 326-332, 2000.

Boens, Shannah et al., Interactor-Guided Dephosphorylation by Protein Phosphatase-1, *Phosphatase Modulators, Methods in Molecular Biology*, vol. 1053, pp. 271-281, 2013.

Bollen, Mathieu et al., "The Extended PP1 Toolkit: Designed to Create Specificity," *Trends Biochem. Sci.*, vol. 35, pp. 450-458, 2010.

Boyce, Michael et al., A Selective Inhibitor of EIF2α Dephosphorylation Protects Cells From ER Stress, *Science*, vol. 307, pp. 935-939, 2005.

Cao, Stewart Siyan et al., "Unfolded Protein Response," *Current Biology*, vol. 22, pp. R622-R626, 2012.

Chen, Ruming et al., "G-actin Provides Substrate-Specificity to Eukaryotic Initiation Factor 2α Holophosphatases," *eLife: Biochemistry, Biophysics and Structural Biology*, vol. 4, pp. 1-18, 2015.

Chen, Ting, et al., Chemical Genetics Identify eIF2α Kinase Heme Regulated Inhibitor as Anti-Cancer Target, Nat. Chem. Biol., vol. 7, pp. 610-616, 2011.

Choy, Meng S. et al., Regulation of Protein Phosphatase 1 by Intrinsically Disordered Proteins, *Biochem. Soc. Trans.*, vol. 40, pp. 969-974, 2012.

Choy, Meng S., et al., "Structural and Functional Analysis of the GADD34:PP1 eIF2α Phosphatase," *Cell Rep.*, vol. 11, pp. 1885-1891, 2015.

Choy, Meng S. et al., "Understanding the Antagonism of Retinoblastoma Portein Dephosphorylation by PNUTS Provides Insights into the PP1 Regulatory Code," *Proc. Natl. Acad. Sci. USA*, vol. 111, pp. 4097-4102, 2014.

Costa-Mattioli, Mauro et al., "eIF2α Phosphorylation Bidirectionally Regulates the Switch from Short to Long-Term Synaptic Plasticity and Memory," *Cell*, vol. 129, pp. 195-206, 2007.

Das, Indrajit et al., "Preventing Proteostasis Diseases by Selective Inhibition of a Phosphatase Regulatory Subunit," *Science*, vol. 348, pp. 239-242, 2015.

Donzé, Oliver et al., "Abrogation of Translation Initiation Factor eIF-2 Phosphorylatioin Causes Malignant Transformation of NIH 3T3 Cells," vol. 14, pp. 3828-3834, 1995.

Duennwald, Martin L. et al., "Impaired ERAD and ER Stress Are and Specific Events in Polyglutamine Toxicity," *Genes & Development*, vol. 22, pp. 3308-3319, 2008.

Duffy, Siobain et al., "Site-Specific, Enzymatic Biotinylation of Recombinant Proteins in *Spodoptera Frugiperda* Cells Using Biotin Acceptor Peptides," *Anal. Biochem.*, vol. 262, pp. 122-128, 1998.

Frostell-Karlsson, Asa et al., "Biosensor Analysis of the Interaction Between Immobilized Human Serum Albumin and Drug Compounds for Prediction of Human Serum Albumin Binding Levels," *J. Med. Chem.*, vol. 43, pp. 1986-1992, 2000.

Gardner, Thomas S. et al., "The Synthesis of Compounds for the Chemotherapy of Tuberculosis v. Some Transformations of Pyridylaldehyde Thiosemicarbazones," *J. Org. Chem.*, vol. 20, pp. 976-980, 1955.

Gilmartin, Aidan G. et al., "Allosteric Wip1 Phosphatase Inhibition Through Flap-Subdomain Interaction", *Nature Chemical Biology*, vol. 10, pp. 181-190, 2014.

Hall, Alan H. et al., "Guanabenz Overdose," *Annals of Internal Medicine*, vol. 102, pp. 787-788, 1985.

Hamamura Kazurori et al., "Salubrinal Acts as a Dusp2 Inhibitor and Suppresses Inflammation in Anti-Collagen Antibody-Induced Arthritis," *Cellular Signalling*, vol. 27, pp. 828-835, 2015.

Harding, Heather P. et al., "An Integrated Stress Response Regulates Amino Acid Metabolism and Resistance to Oxidative Stress," *Molecular Cell*, vol. 11, pp. 619-633, 2003.

Harding, Heather P. et al., "Perk is Essential for Translational Regulation and Cell Survival During the Unfolded Protein Response," *Molecular Cell*, vol. 5, pp. 897-904, 2000.

Harding, Heather P. et al., "Regulated Translation Initiation Controls Stress-Induced Gene Expression in Mammalian Cells," *Molecular Cell*, vol. 6, pp. 1099-1108, 2000.

Harding, Heather P. et al., "Ppp1r15 Gene Knockout Reveals an Essential Role for Translation Initiation Factor 2 Alpha (eIF2α) Dephosphorylation in Mammalian Development", *Proc. Nat. Acad. Sci. USA*, vol. 106, pp. 1832-1837, 2009.

Henry, Earl Webb et al., "Comparison of Trembler and Trembler-J Mouse Phenotypes: Varying Severity of Peripheral Hypomyelination," *J. Neuropathology and Experimental Neurology*, vol. 42, pp. 688-706, 1983.

Heroes, Ewald et al., "The PP1 Binding Code: A Molecular-Lego Strategy That Governs Specificity," *The FEBS Journal*, vol. 280, pp. 584-595, 2013.

Jazcilevich, S. et al., "Induction of Fatty Liver in the Rat After Cycloheximide Administration," *Laboratory Investigation*, vol. 23, pp. 590-594, 1970.

Jousse, Céline et al., "Inhibition of a Constitutive Translation Initiation Factor 2α Phosphatase, CReP, Promotes Survival of Stressed Cells," *J. Cell Biol.*, vol. 163, pp. 767-775, 2003.

Lee, Yun-Young et al., "An Upstream Open Reading Frame Regulates Translation of GADD34 During Cellular Stresses That Induce eLF2α Phosphorylation," vol. 284, pp. 6661-6673, 2009.

Li, Wen-Tai et al., "Synthesis and Biological Activities of 2-Amino-1-Arylidenamino Imidazoles as Orally Active Anticancer Agents," *J. Med. Chem.*, vol. 53, pp. 2409-2417, 2010.

Lin, Wensheng et al., "Endoplasmic Reticulum Stress in Disorders of Myelinating Cells," *Nat Neuroscience*, vol. 12, pp. 379-385, 2009.

Marciniak, Stefan J. et al., "CHOP Induces Death by Promoting Protein Synthesis and Oxidation in the Stressed Endoplasmic Reticulum," *Genes & Development*, vol. 18, pp. 3066-3077, 2004.

Nguyen, Phu Hai et al., "Structure-Activity Relationship Study Around Guanabenz Identifies Two Derivatives Retaining Antiprion Activity but Having Lost [alpha]2-Adrenergic Receptor Agonistic Activity," *ACS Chemical Neuroscience*, vol. 5, pp. 1075-1082, 2014.

Nishitoh, Hideki et al., "ASK1 is Essential for Endoplasmic Reticulum Stress-Induced Neuronal Cell Death Triggered by Expanded Polyglutamine Repeats," *Genes and Development*, vol. 16, pp. 1345-1355, 2002.

(56) References Cited

OTHER PUBLICATIONS

Novoa, Isabel et al., "Feedback Inhibition of the Unfolded Protein Response by GADD34-Mediated Dephosphorylation of eIF2α," *J. Cell Biol.*, vol. 153, pp. 1011-1021, 2001.
Pavitt, Graham D. et al., "New Insights into Translational Regulation in the Endoplasmic Reticulum Unfolded Protein Response," *Cold Spring Harbor Perspectives in Biology*, vol. 4, pp. 1-13, 2012.
Pervin, Shehla et al., "Increased Susceptibility of Breast Cancer Cells to Stress Mediated Inhibition of Protein Synthesis," *Cancer Research*, vol. 68, pp. 4862-4874, 2008.
Powers, Evan T. et al., "Biological and Chemical Approaches to Diseases of Proteostasis Deficiency," *Annu. Rev. Biochem.*, vol. 78, pp. 959-991, 2009.
Ring, Joshua R. et al., "Improving the Inhibitory Activity of Arylidenaminoguanidine Compounds at the n-methyl-d-aspartate Receptor Complex From a Recursive Computational-Experiment Structure-Activity Relationship Study", *Bioorganic & Medicinal Chemistry*, vol. 21, pp. 1764-1774, 2013.
Robert, Francis et al., "Initiation of Protein Synthesis by Hepatitis C Virus is Refractory to Reduced eIF2 GTP Met-tRNA$_i^{Met}$ Ternary Complex Availability," *Molecular Biology of the Cell*, vol. 17, pp. 4632-4644, 2006.
Scheuner, Donalyn et al., "Translational Control is Required for the Unfolded Protein Response and in Vivo Glucose Homeostasis," *Molecular Cell*, vol. 7, pp. 1165-1176, 2001.
Schilling, Gabriele et al., "Intranuclear Inclusions and Neuritic Aggregates in Transgenic Mice Expressing a Mutant N-terminal Fragment of Huntingtin," *Human Molecular Genetics*, vol. 8, pp. 397-407, 1999.
Stenlund, Peter et al., "Studies of Small Molecule Interactions With Protein Phosphatases Using Biosensor Technology," *Analytical Biochemistry*, vol. 353, pp. 217-225, 2006.
Tavernarakis, Nektarios, "Ageing and the Regulation of Protein Synthesis: A Balancing Act?" *Trends in Cell Biology*, vol. 18, pp. 228-235, 2008.
Tsaytler, Pavel et al., "Exploiting the Selectivity of Protein Phosphatase 1 for Pharmacological Intervention," *FEBS Journal*, vol. 280, pp. 766-770, 2013.
Tsaytler, Pavel et al., "Selective Inhibition of a Regulatory Subunit of Protein Phosphatase 1 Restores Proteostasis," *Science*, vol. 332, pp. 91-94, 2011.
Virshup, David M. et al., "From Promiscuity to Precision: Protein Phosphatases Get a Makeover," *Molecular Cell*, vol. 33, pp. 537-545, 2009.
International Search Report in PCT/GB2016/050990, dated Aug. 30, 2016 (6 pages).
International Search Report in PCT/GB2016/050991, dated Jun. 6, 2016 (6 pages).
CAPLUS Registry No. 849334-94-7, Hydrazinecarboximidamide, 2-[(2,3-dichlorophenyhmethylene]-hydrochloride, Apr. 27, 2005 (1 page).
CAPLUS Registry No. 94023-67-3, 2-[(2,3-Dichlorophenyl)methylene]hydrazinecarboximidamide, Sep. 8, 1985 (1 page).
Krzyzosiak et al., "Target-Based Discovery of an Inhibitor of the Regulatory Phosphatase PPP1R15B," *Cell*, vol. 174, pp. 1216-1228 (2018).
Database Registry No. 1563208-37-6, Hydrazinecarboximidamide, 2-[(3,4,5-trifluorophenyl)methylene], Chemical Abstracts Service, Mar. 6, 2014.
Database Registry No. 1704405-00-4, Hydrazinecarboximidamide, 2-[(2,4,5-trifluorophenyl)methylene], Chemical Abstracts Service, May 14, 2015.
Database Registry No. 849460-24-8, Hydrazinecarboximidamide, 2-[(3,5-dibromophenyhmethylene], Chemical Abstracts Services, Apr. 29, 2005.
Tribouillard-Tanvier et al., Antihypertensive Drug Guanabenz Is Active In Vivo Against Both Yeast and Mammalian Prions, *PLoS ONE*, vol. 3, Issue 4, pp. 1-7 (2008).
Way et al., "Harnessing the Integrated Stress Response for the Treatment of Multiple Sclerosis," *Lancet Neurol.*, vol. 15, No. 4, pp. 434-443 (2016).

\* cited by examiner

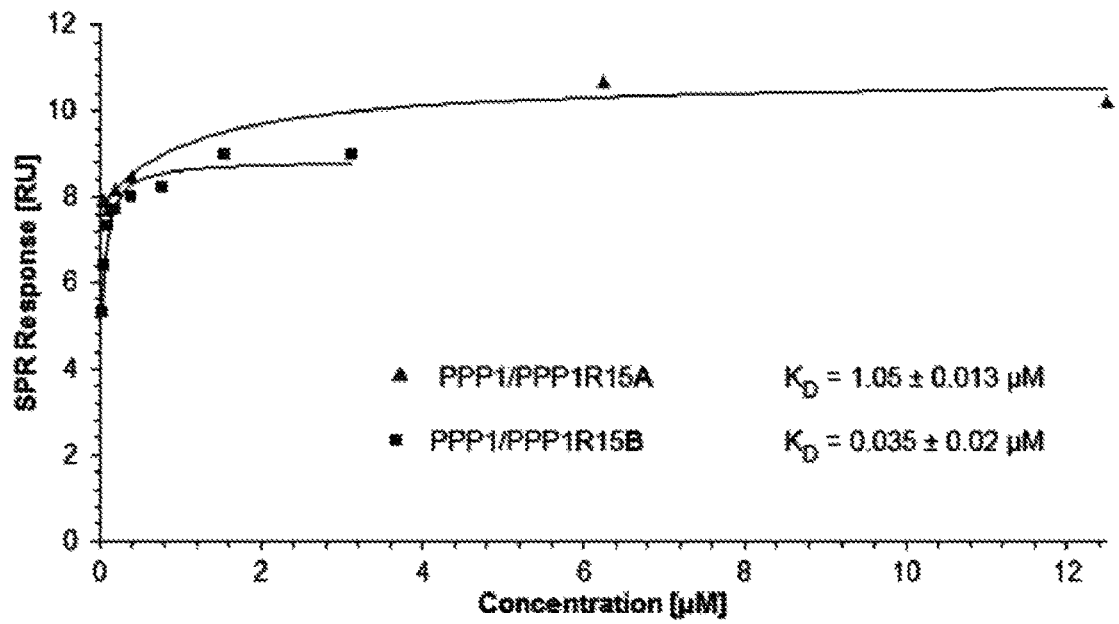
Fig. 1
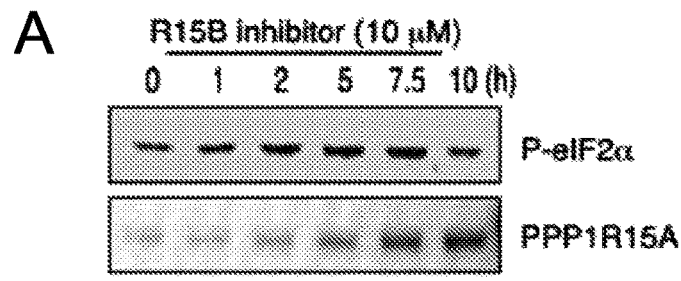
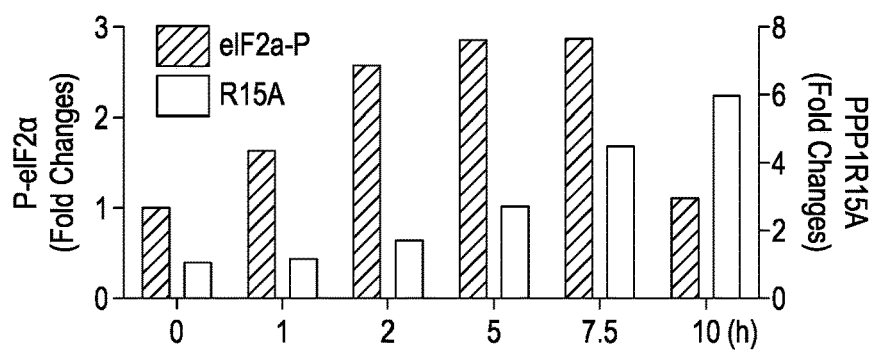
Fig. 2

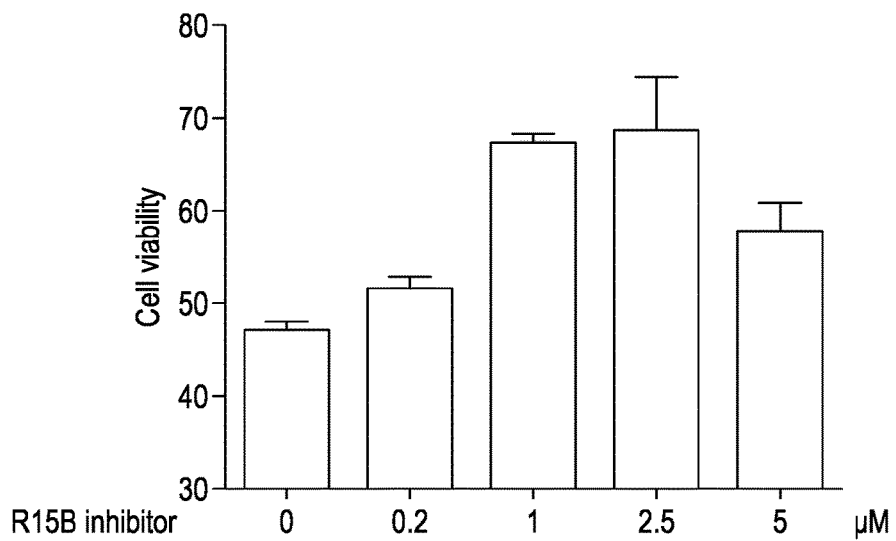
Fig. 3
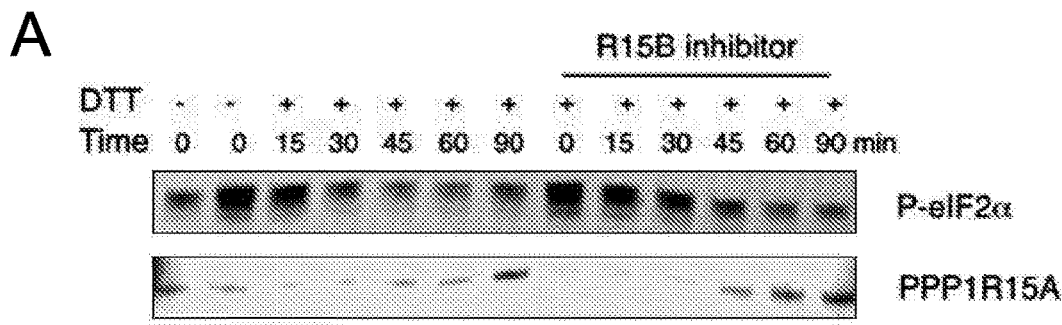
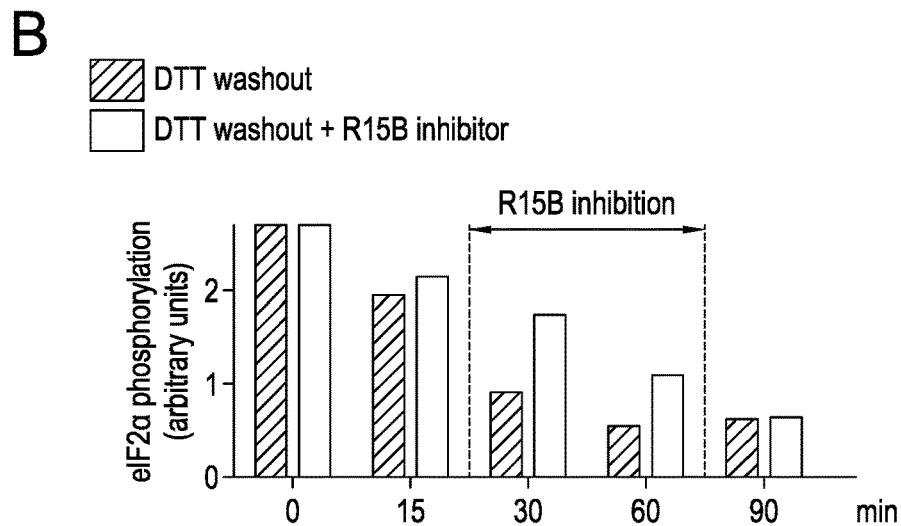
Fig. 4

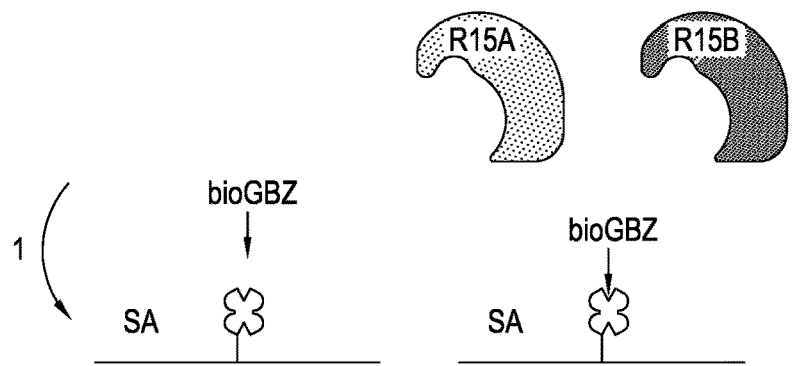
Fig. 13A
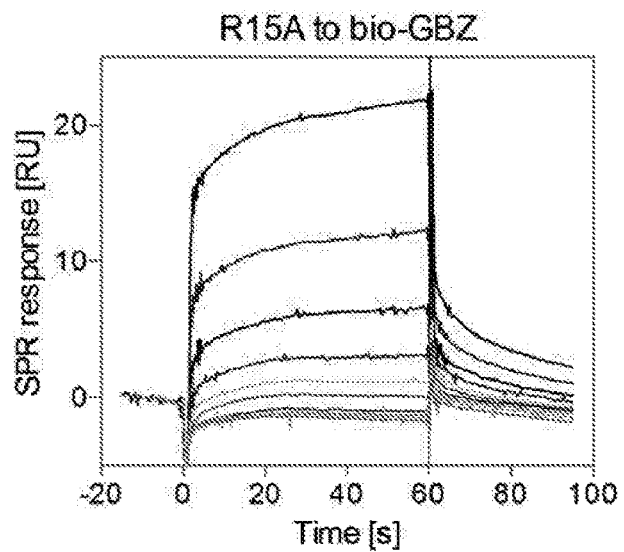
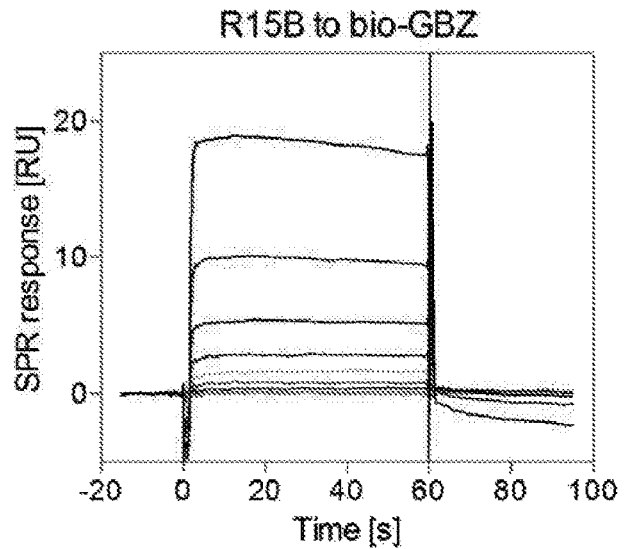
Fig. 13B

```
PR15A_HUMAN  ------------------------------------------------------MAPGQAPHQA  10
PR15B_HUMAN  MEPGTGGSRKRLGPRAGFRFWPPFFPRRSQAGSSKFPTPLGPENSGNPTLLSSAQPETRV  60
                                                                   :: .*  :.

PR15A_HUMAN  TPWRDAHPFFLLSPVMGLLSR--AWSRLRGLGPLEPWLVEAVKGAALVEAGLEGEART--  66
PR15B_HUMAN  SYWTKL-LSQLLAPLPGLLQKVLIWSQLFGGMFPTRWLDFAGVYSA--LRALKGREKPAA  117
             : *.   **:*; ***.;   **;* *     **  *  :*   ,*;*;. :

PR15A_HUMAN  -----------------PLAIPH---------TPWGRRPEEEAEDSGGPGEDRETLGLKTSSS  103
PR15B_HUMAN  PTAQKSLSSLQLDSSDPSVTSPLDWLEEGIHWQYSPPDLKLELKAKGSALDPA-AQAFLL  176
                              *.;            *  *;    :  .*, ;    ::

PR15A_HUMAN  LPEAWGLLDD----DDGMYGEREATSVPRGQGSQFADGQRAPLSPSLLIRTLQGSDKNPG  159
PR15B_HUMAN  EQQLWGVELLPSSLQSRLYSNRELGSSPSGPLN---------------------------  209
              : **:      :. :*.;** * * *

PR15A_HUMAN  EEKAEEEGVAEEEGVNKFSYPPSHRECCPAVEEEDDEEAVKK-----------EAH  204
PR15B_HUMAN  ------IQRIDNFSVVSYLLNPSYLDCFPRLEVSYQNSDGNSEVVGFQTLTPESSCLRED  263
                   :: ,*  .:    **; ;*  * ;*. ::. :.                .  .

PR15A_HUMAN  RTSTSALSPGSKPSTWVSCPGEEENQATEDKR------TERSKGARKT------------  246
PR15B_HUMAN  HCHPQPLSAELIPASWQGCPPLSTEGLPEIHHLRMKRLEFLQQANKGQDLPTPDQDNGYH  323
             :  ,.**   *;;* ,**  . :   * ::      *  : *.*

PR15A_HUMAN  ----------SVSPRSSGSDPRSWEYRSGEASEE-----KEEKAH---KETGKGEAAPGPQS  290
PR15B_HUMAN  SLEEEHSLLRMDPKHCRDNPTQFVPAAGDIPGNTQESTEEKIELLTTEVPLALEEEESPSE  383
             ;.*;  ..;:* .;   ;*:   ;*.  ***  ;    .*. .    .*;..

PR15A_HUMAN  SAPAQRPQLKSWWCQPSDEEEGEVKALGAAEKDGEA---ECPPCIPPPSAFLKAWVYWPG  347
PR15B_HUMAN  GCPSSEIP-------MEKEPGEGRISVVDYSYLEGDLPISARPACSN------KLIDYILG  431
             ..*:..         .:  **;..:; ;  :*;       * *         *  *  *

PR15A_HUMAN  EDTEEEEDE--EE------DEDSDSGSDEEEGEAEASSSTPATGVFL------KSWVYQPGE  395
PR15B_HUMAN  GASSDLETSSDPEGEDWDEEAEDDGFDSDSSLSDSDLEQDPEGLHLWNSFCSVDPYNPQN  491
             ;,; *,  *   .   ;*  ,*.* *.;.. :::..:   *:.*  .    *;* ;

PR15A_HUMAN  DTEEEEDEDSDTGSAEDEREAETSASTPPASAFLKAWVYRPGEDTEEEEDEDVDSEDKED  455
PR15B_HUMAN  FTAT--------------------IQTAARIVPEEPSDSEK--DLSG--KSD  519
             *                        ; .*   * *  ::.*; *:..  *,*

PR15A_HUMAN  DSEAALGEAESDPHPSHPDQR-AHFRGWGYRPGKETEEEEAAEDWGEA--------EPCPF  507
PR15B_HUMAN  L-E---NSSQSGSLPETPEHSSGEEDDWESS-----ADEAESLKLWNSFCNSDDPYNPLNF  571
             * .  ,;:*   *, *::  ..  *       ::* *:; * ,      :* *

PR15A_HUMAN  RVAIYVPGEKPPPPW---AP-----------PRLPLRLQ----RRLKRPET---PTHDPD  546
PR15B_HUMAN  KAPFQTSGENEKGCRDSKTPSESIVAISECHTLLSCKVQLLGSQESECPDSVQRDVLSGG  631
             :. ;., **;     :*         *    ::*  :. ; *;;   .,

PR15A_HUMAN  PETPLKARKVRFSEKVTVHFLAVWAGPAQAARQGPWEQLARDRSRFARRITQAEELSPC  606
PR15B_HUMAN  RHTHVKRKKVTFLEEVTEYY-----ISGDEDRKGPWEEFARDGCRFQKRIQETEDAIGYC  696
              .* ;* ;** * *;**  ::         .: *;****;;*** .** ;** ;;;; ;. *

PR15A_HUMAN  LTPAARARAWARLRNPPLAPIPALTQTLPSSSVPSSPVQTTPLSQAVATPSRSSAAAAAA  666
PR15B_HUMAN  LTFEHRERMFNRLQGTCFKGLNVLKQC---------------------------  713
             **  * *,; **;      ;  ;.*,*

PR15A_HUMAN  LDLSGRRG  674
PR15B_HUMAN  --------
```

Fig. 16

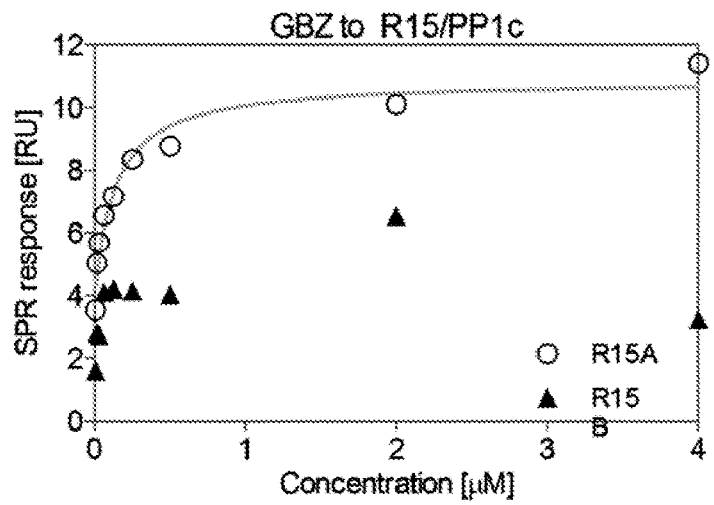
Fig. 21
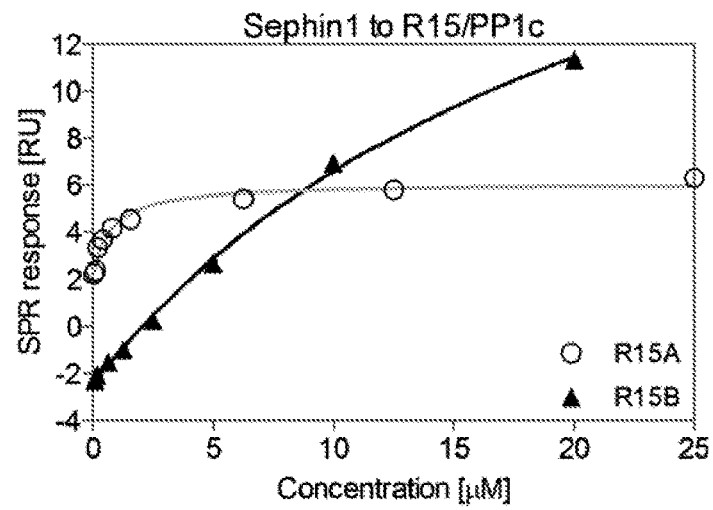
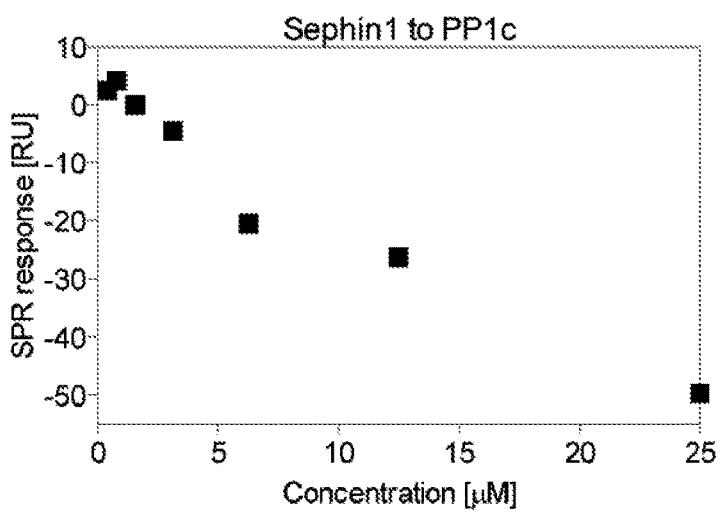
Fig. 22

|  | $K_D$ [μM] [1] | | |
| --- | --- | --- | --- |
|  | PP1/PPP1R15A | PP1/PPP1R15B | PP1 |
| GBZ | 0.122 ± 0.009 | --[2] | -- |
| Sal003 | 29.2 ± 8.0 | 27.5 ± 5.5 | 27.8 ± 6.5 |
| Sephin1 | 0.786 ± 0.036 | 23.0 ± 0.9 | -- |
| TST3 | 0.977 ± 0.12 | 0.033 ± 0.02 | -- |

1) Steady-state binding constant from SPR
2) -- = no binding

METHODS FOR SELECTING PHOSPHATASE SELECTIVE AND NON-SELECTIVE PHOSPHATASE INHIBITORS

CROSS-REFERENCE TO RELATED APPLICATIONS

This application is the U.S. national phase entry under 35 U.S.C. § 371 of International Application No. PCT/GB2016/050990, filed on Apr. 8, 2016, which claims priority to British Patent Application Nos. GB 1505971.0, filed on Apr. 8, 2015, and GB 1505975.1, filed on Apr. 8, 2015.

SEQUENCE LISTING

This application contains a sequence listing, which has been submitted electronically in ASCII format and is hereby incorporated by reference in its entirety. Said ASCII copy of the sequence listing was created on Oct. 6, 2017, under the filename 00012-0026-00000_SL.txt and is 13,164 bytes in size.

The present invention discloses a method to discover selective inhibitors of phosphatases.

BACKGROUND TO THE INVENTION

The reversible phosphorylation of proteins controls virtually all aspects of cell and organismal function, allowing cells to adapt to sudden changes through the antagonistic action of kinases and phosphatases. Consequently, targeting phosphorylation offers a broad range of therapeutic opportunities and kinases have arisen as the most prevalent drug targets in today's pharmaceutical research with more than 3000 approved and experimental drugs. However, while targeting phosphatases should in principle be as attractive as kinases, the therapeutic potential of phosphatases has been overlooked.

The majority of protein phosphorylation occurs on serine and threonine and selective serine/threonine dephosphorylation is achieved by hundreds of different dimeric or trimeric holoenzymes assembled from one of only a few catalytic subunits combined with one amongst hundreds of diverse regulatory subunits (Heroes et al., FEBS Journal, 280, 584-595, 2012).

Phosphatases have been generally considered to be undruggable for a number of reasons. For example, many phosphatases are oligomeric. Thus, inhibition of the catalytic component of the holoenzyme such as PP1c results in inhibition of the many (e.g. hundreds) holophosphatases sharing the same catalytic subunits and may be toxic. Since selectivity is an important property for drug development, the promiscuity of catalytic phosphatases has led them to acquire the reputation of being undruggable.

Secondly, regulatory subunits of phosphatases are intrinsically disordered (Bollen et al., 2010; Choy et al., 2012a) and are therefore, difficult to express and unstable. Amongst the approximately 200 mammalian PP1 (protein phosphatase 1) holophosphatases, only eight have been crystallized. There is therefore a lack of structural information on holophosphatases which means that structure-based drug design is not easily applicable to this class of enzyme. To date, the holophosphatases for which structural information is available only contain a small peptide (less than approximately 100 amino acids) from the regulatory subunits (Ragusa:2010hd; Choy et al., 2014) and these smaller structures make it difficult to guide drug discovery.

In addition, enzymatic assays based on hydrolysis of substrates of artificial substrates will mostly lead to the discovery of catalytic inhibitors which are generally not selective.

Accordingly, there is a need to develop a generic strategy and assay to selectively inhibit phosphatases and enable specific inhibitors, and therefore drugs with a therapeutic application, to be identified.

SUMMARY OF THE INVENTION

Recently, the feasibility of inhibiting selectively a serine/threonine phosphatase has been demonstrated. Guanabenz (Tsaytler et al., Science, 332, 91-94, 2011; Tsaytler and Bertolotti, FEBS Journal, 280, 766-770, 2012) and its derivatives, some of which are disclosed in WO2014108520 (Medical Research Council), were found to selectively inhibit PPP1R15A/GADD34 ("R15A"), a stress-induced regulatory subunit of the serine/threonine protein phosphatase 1, and was proposed as a treatment for diseases associated with protein misfolding stress. Likewise, a Guanabenz derivative, Sephin1 (Das et al., 2015) has been shown to selectively inhibit PPP1R15A/GADD34. Sephin1 has therefore been proposed as a treatment for diseases associated with protein misfolding stress. Other derivatives have been disclosed in WO2016001389A1, WO2016001390A1 and WO2014138298A1, for example, and are proposed to possess similar activity. However, improved assays for selectivity are needed to confirm whether these molecules are selective for R15A inhibition.

Other inhibitors of phosphatases have been identified serendipitously. For example, cyclosporin A and FK506 bind to immunophilin proteins, cyclophilin and FKBP12, respectively, and the resulting complex bind to calcineurin, a heterodimeric phosphatase composed of a catalytic subunit PPP3 and one of two regulatory subunits PPP3R1 or PPP3R2. Cyclosporin A is a phosphatase inhibitor but it does so by an indirect route: cyclosporin does not target the regulatory subunit of calcineurin holophosphatase.

An allosteric WIP1 phosphatase has been reported (Gilmartin et al., 2014). This inhibitor was discovered in an enzymatic assay. To date, there are no assays available to identify selective and allosteric inhibitors of phosphatase.

In summary, while phosphatase inhibitors have been previously described, it is important to note that they have been discovered serendipitously. There is no available method to generically identify a selective phosphatase inhibitor.

One way to identify selective and allosteric inhibitors of phosphatases consists in targeting their regulatory subunits. R15A inhibitors have been serendipitously identified and provided the proof of concept that serine-threonine phosphatases can be selectively inhibited by targeting regulatory subunits (Das et al., 2015; Tsaytler et al., 2011). In principle, the same paradigm could be exploited to selectively inhibit one of the many other PP1 holophosphatases. However, the rational discovery of selective inhibitors of intrinsically disordered regulatory subunits of phosphatases represents an unmet challenge.

The present invention provides an assay method for determining selective binding of holoenzymes such as phosphatases (i.e. holophosphatases). Suitable holophosphatases include members of the superfamily of phosphoprotein phosphatases (PPPs) comprising Ser/Thr protein phosphatases 1-7 (PP1-7), as reviewed, for example, in (Heroes et al., FEBS Journal, 280, 584-595, 2012). PPP1R15A (also known as GADD34 and referred to herein as "R15A") and PPP1R15B (also known as CReP and referred to herein as "R15B") are holophosphatases of the PP1 family.

Accordingly, in a first aspect there is provided a method for screening a test compound to determine whether the compound binds a holophosphatase selectively or non-selectively comprising:
i) providing a first holophosphatase wherein said holophosphatase is captured/immobilised;
ii) testing a test compound for its ability to bind to the first holophosphatase;
iii) providing a second holophosphatase wherein said second holophosphatase is captured/immobilised;
iv) testing the same test compound for its ability to bind to the second holophosphatase;
v) comparing the binding of the test compound to said first holophosphatase with the binding to said second phosphatase
wherein a test compound that binds a holophosphatase selectively will bind to said first holophosphatase but not said second holophosphatase; or will bind to said second holophosphatase but not said first; or wherein a compound that binds a holophosphatase non-selectively will bind to both said first holophosphatase and said second holophosphatase Suitably, the ability of a test compound to bind to a first holophosphatase and the ability of the same test compound to bind to a second holophosphatase are tested sequentially for example using separate chips, beads or reaction mixtures as described in more detail herein to determine a binding affinity of the test compound to each of the holophosphatases separately for comparison.

In one embodiment, the holophosphatase, i.e. said first and/or said second holophosphatase, is an oligomeric enzyme composed of a catalytic and one or more regulatory subunit. There are more than 400 phosphatases regulating virtually all aspects of cellular function, reviewed, for example in Heroes et al. (2012). There are over 200 regulatory subunits that share a few catalytic subunits. Regulatory subunits of phosphatases are intrinsically disordered, i.e. natively unstructured (Bollen et al., 2010; Choy et al., 2012a) and tend to become structured only upon binding to their catalytic subunit. No methods have been provided previously to identify inhibitors of such natively unstructured molecules as developing such methods is generally problematic. When used alone (tagged or untagged), the natively unstructured regulatory subunits of phosphatases are generally unstable or precipitate. Therefore, using the regulatory subunits alone has not allowed compounds of relevant biological activities to be identified.

The present method enables complexes containing the regulatory subunits, which are natively unstructured proteins, when bound to their interaction partners to be generated and used for screening thus allowing new drugs targeting this class of protein to be identified.

Suitably, the holophosphatase is isolated and purified by any available method. The holophosphatase can, for example, be expressed as subunits in a suitable expression system such as a bacterial, insect or mammalian cell expression system. The subunits can be purified by any suitable methods such as, for example, chromatography.

As the regulatory subunits of a holophosphatase are intrinsically disordered, as described above, specific methods for expression and purification may be required. Accordingly, in one embodiment, the regulatory subunit may be tagged to facilitate expression and purification. Suitably, the regulatory subunit may be tagged with two tags. Suitable tags will be familiar to those skilled in the art and include, for example, affinity tags such as Maltose Binding Protein-tag, his-tag etc. In a particular embodiment, for purifying R15A (and/or R15B), as described herein, MBP-tag may be used in combination with his-tag. Advantageously, MBP-tag (Maltose Binding Protein) increases solubility of recombinant proteins expressed in E. coli. The his-tag is also an affinity tag. A MBP-catalytic subunit-His tagged protein can therefore be purified in a two-step procedure, resulting in a pure and relatively stable protein, as described herein for MBP-R15A-His. In another embodiment, the catalytic subunit may also be expressed so as to comprise a tag such as an affinity tag.

Thus, in one embodiment, the holophosphatase can be reconstituted by assembling the subunits. Alternatively, the different subunits can be co-expressed in a suitable expression system (e.g. bacterial, insect or mammalian cell) and the holoenzyme can be purified by any suitable method (for example chromatography).

In another embodiment, the holophosphatase may be an endogenous protein purified from a cell extract by any suitable method, for example by chromatography.

In one embodiment of any aspect or embodiment of the invention, the regulatory subunit may be provided as a truncated version of the full length subunit. Suitably, a truncated version will retain the ability to bind to the catalytic subunit and retain the necessary catalytic function. For example, and as described herein, a suitable truncated version of R15A and/or R15B is one which retains the ability to bind to the catalytic subunit PP1c and retains its catalytic activity of binding to and dephosphorylating eIF2α. In one embodiment, where the regulatory subunit is R15A, it is provided as a truncated fragment comprising amino acids 325-636. In one embodiment, where the regulatory subunit is R15B, it is provided as a truncated fragment comprising amino acids 340-698. The amino acid sequences of R15A and R15B are given here in FIG. 16. Advantageously, using shorter fragments can overcome problems in low protein yields and low stability observed using the full length proteins. However, the fragments described herein, as exemplified for R15A and R15B, are larger than those in previously reconstituted PP1c phosphatases which only contained fragments of regulatory subunits smaller than 100 amino acids (Chen et al., 2015; Choy et al., 2015). In another embodiment, the catalytic subunit may be a truncated form of the native protein. Suitably, such truncated form would retain its ability to bind to the regulatory subunit as well as its catalytic activity.

In one embodiment, said testing a test compound for its ability to bind to said first holophosphatase, said second holophosphatase or said catalytic subunit is through determining binding affinity using a surface plasmon resonance (SPR) approach.

In another embodiment, the holophosphatase is immobilised on a surface. Suitable surfaces are any which allow for subsequent binding analysis to be made. For example, the surface may be a chip such as an SPR (surface plasmon resonance) sensorchip which is suitable for SPR measurements. In other embodiments, the surface may be a bead or resin or e.g. a well of a microplate. Suitably, the holophosphatase is reconstituted by immobilisation on a surface.

In another embodiment, the holophosphatase is immobilised using an affinity capture method or any relevant capture method. Suitable affinity capture methods include using biotin:streptavidin or other similar binding pairs—for example histidine-nickel, GST glutathion etc.

In one embodiment, the catalytic subunit of the holoenzyme, such as, for example, PP1c, is first immobilized on the chip and then it is bound to a regulatory subunit. This is shown schematically in FIG. 33 where catalytic subunits A or B are demonstrated.

In one embodiment, the holophosphatase may be reconstituted on beads using an affinity tagged subunit. For example, His-PP1 and/or MBP-R15A-His may be reconstituted on beads. Suitable beads include amylose beads. Suitably, biotinylated proteins/peptides may be generated using in vivo biotinylation in insect cells. In one embodiment, the tag used on the regulatory and catalytic subunit may be different.

In another embodiment, assays for binding of test compound to a holophosphatase (or catalytic subunit) in accordance with any aspect or embodiment of the invention are carried out in solution.

In one embodiment, the method for screening for a test compound in accordance with any aspect of embodiment of the invention further comprises an additional step:
vi) providing a catalytic subunit of said first and second holophosphatase wherein said catalytic subunit is captured/immobilised;
vii) testing said candidate phosphatase inhibitor molecule for its ability to bind to the catalytic subunit.

A comparison of the binding profile of test compounds with the binding to the catalytic domain of a holoenzyme can be an important step in profiling the selectivity or the lack thereof of the binding molecules. In one embodiment, candidate compounds of interest are those that do not bind to and/or inhibit the catalytic subunit but are selective for the holophosphatase comprising the catalytic subunit in conjunction with one specific regulatory subunit.

In the context of an assay method comprising the additional steps vi) and vii), and with reference to FIG. 33, a compound that binds to A and is a candidate selective A inhibitor (or activator) will bind preferentially to chip A but not B or C. A compound that binds to B and is a candidate selective B inhibitor (or activator) will bind preferentially to chip B but not A or C. A non-selective binder or inhibitor can bind more than one chip.

In another embodiment, the method further comprises determining whether a selective or non-selective inhibitor has an effect on the catalytic subunit alone (e.g. in an enzymatic assay) or wherein an inhibitor which is an inhibitor or activator of a regulatory subunit i.e. A or B or both has no effect on a catalytic subunit.

In one embodiment, the method for screening for a test compound further comprises preforming a confirmatory assay to test for a particular inhibitory/activatory activity in other assays. For example, a test inhibitor or activator may be validated in an enzymatic assay or a cell based assay to demonstrate target engagement. Suitable assays for activity of particular holoenzymes will depend on the particular cell pathways in which they are involved. The skilled person will be aware of suitable assays for any particular holoenzyme in the knowledge of the molecules with which the holoenzyme interacts as substrates.

Target engagement may be validated by repeating the same assay in cells knock out or knocked down for the targeted phosphatase. Knock out cells can be generated by conventional methods (e.g. gene knock out or Crispr/Cas knock out) and gene silencing can be achieved by any suitable method such as siRNA. In the absence of the target, a selective compound will have no effects in cells.

Suitably further validation of a test compound may through validation in biological assays. Any suitable assays revealing the biological activity of the target can be used. For example, if the target is involved in signalling, the induction of the signalling pathway can be monitored by any method (e.g. antibody based method, flow cytometry etc.). A phosphatase inhibitor or activator will alter the signalling pathway. Any other biological assays can be used to monitor the target inhibition or activation. For example the assay can be a growth assay if the target activity impact on cell growth, it can be death assays (if the target activity is important for cell survival), it can be protection from chemicals (if the pathway is involved is protection form chemical) etc.

Suitably, a selective phosphatase inhibitor will increase or prolong the phosphorylation of its substrate. In one embodiment, a selective inhibitor is one which has a binding affinity or biological activity when presented at concentrations below 10 µM, even more preferably below 5 µM, even more preferably below 1 µM and even more preferably below 0.5 µM.

An example of an assay method in accordance with the invention is shown in FIG. 33.

In this example, the method consists of the following steps (FIG. 33):
1. Isolating and purifying a holophosphatase (called A) in this example.

This can be done by any available method, either using the endogenous protein or by expressing the subunits in any suitable system (bacteria, insect or mammalian cells, etc.), purifying them and reconstituting a holophosphatase. In this example, the catalytic subunit of the phosphatase PP1c is in vivo biotinylated for high affinity capture on a streptavidin SPR CHIP.

2. Immobilizing the holophosphatase on the chip

In the example here, the catalytic subunit PP1c is first immobilized on the chip and then it is bound to a regulatory subunit (A or B in the example here).

3. Screening molecules/test compounds binding to the holophosphatase A (chip A)

4. Repeating steps 1-3 with a different phosphatase called B in this example (chip B)

5. Repeat steps 1-2 using the catalytic subunit to generate chip C

6. Profiling the selectivity of test compounds by testing their binding to chip A, B and C.

A selective A inhibitor (or activator) will bind preferentially to chip A but not B or C. A selective B inhibitor (or activator) will bind preferentially to chip B but not A or C. A non-selective inhibitor can bind more than one chip.

The test compounds identified by this method can be tested for their activity on catalytic subunits alone. A selective binder or inhibitor oractivator of a regulatory subunit has no effect on a catalytic subunit.

The compounds identified by this method are validated in other assays including enzymatic assays or cell based assays to demonstrate target engagement. A selective phosphatase inhibitor will increase or prolong the phosphorylation of its substrate. To validate target engagement, the same assay is repeated in cells which are knock out or knocked down for the targeted phosphatase. In absence of the target, a selective compound will have no effects in cells.

The compounds may be validated in biological assays. Suitable assays revealing the activity of a particular target will be familiar to those skilled in the art.

According to another aspect of the invention there is provided a series of assay methods for use in identifying, screening for, evaluating, or characterising candidate polypeptides, polynucleotides, antibodies, peptides or small molecule compounds capable of inhibiting PPP1R15B ("R15B").

In further aspects of the invention, inhibitor compounds are described.

While PPP1R15A inhibitors have been previously described, no selective inhibitors of a different serine/threonine phosphatase have been reported. It was therefore unknown whether another phosphatase could be selectively inhibited. The Applicants investigated whether it is possible to selectively inhibit PPP1R15B and whether such selective inhibition could be beneficial. Contrary to PPP1R15A knock-out mice which appear normal, mice lacking PPP1R15B do not survive the first day of post-natal life (Harding et al., Proc. Natl. Acad. Sci. U.S.A., 106, 1832-1837, 2009). Thus, whereas PPP1R15A inhibition was predicted to be safe, inhibition of PPP1R15B was predicted to be detrimental. However, the inventors have surprisingly found that PPP1R15B can be selectively inhibited and that such inhibition leads to therapeutic benefit.

Inhibition of PPP1R15B instead of PPP1R15A inhibition may be advantageous as the number of therapeutic indications that can be treated with PPP1R15A inhibitors is predicted to be restricted to diseases where PPP1R15A is expressed and where PPP1R15A is in the disease mode of action. PPP1R15B in contrast is constitutively expressed and therefore a more broadly applicable disease target. As described herein, PPP1R15B inhibition can be used in treatment of Huntington's disease. A PPP1R15B selective inhibitor useful in the present invention may be a protein or polypeptide, polynucleotide, antibody, peptide or small molecule compound. Alternatively, PPP1R15B may be inactivated by gene editing.

In one aspect, there is provided a PPP1R115B selective inhibitor, (E)-2-(2,3-dichlorobenzylidene)hydrazine-1-carboximidamide (also referred to herein as "TST3"):

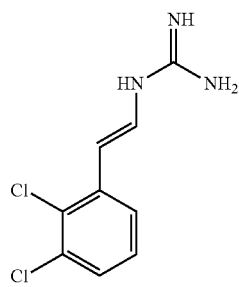 [SMILES: N=C(N)N/C=C/c1cccc(Cl)c1Cl]

According to another aspect of the invention there is provided a PPP1R15B selective inhibitor for use in therapy.

According to another aspect of the invention there is provided a method of treating a subject having a disease state alleviated by the inhibition of PPP1R15B, wherein the method comprises administering to the subject a therapeutically effective amount of a PPP1R15B selective inhibitor.

According to another aspect of the invention there is provided a method of preventing a disease state alleviated by the inhibition of PPP1R15B in a subject, wherein the method comprises administering to the subject a therapeutically effective amount of a PPP1R15B selective inhibitor.

According to another aspect of the invention there is provided a PPP1R15B selective inhibitor for use in the treatment or prevention of a disease state alleviated by the inhibition of PPP1R15B.

According to another aspect of the invention there is provided use of a PPP1R15B selective inhibitor in the manufacture of a medicament for the treatment or prevention of a disease state alleviated by the inhibition of PPP1R15B.

In one embodiment, the disease state alleviated by the inhibition of PPP1R15B is a disorder associated with accumulation of misfolded proteins or proteostasis disorder.

In a further embodiment, the disease is Huntington's disease, Parkinson's disease, a tauopathy, a protein trafficking disease or a myelin disorder.

In another embodiment, the disease is any polyglutamine disorder.

In a further embodiment, the disease is Distal hereditary motor neuropathy with mutations in the chaperone HSJ1.

According to another aspect of the invention there is provided use of a compound, or a pharmaceutically acceptable salt thereof, as a selective inhibitor of PPP1R15B, wherein the compound is selected from the following structures:

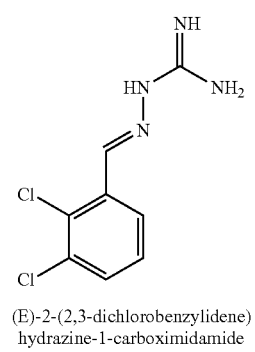

Example 1

(E)-2-(2,3-dichlorobenzylidene) hydrazine-1-carboximidamide

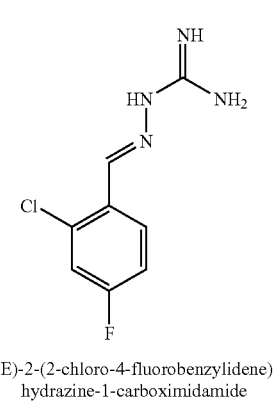

Example 2

(E)-2-(2-chloro-4-fluorobenzylidene) hydrazine-1-carboximidamide

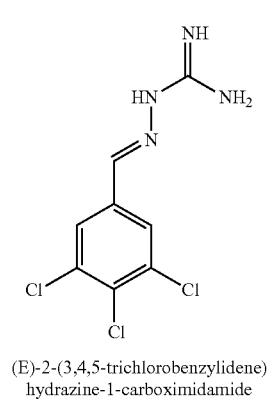

Example 3

(E)-2-(3,4,5-trichlorobenzylidene) hydrazine-1-carboximidamide

Example 4

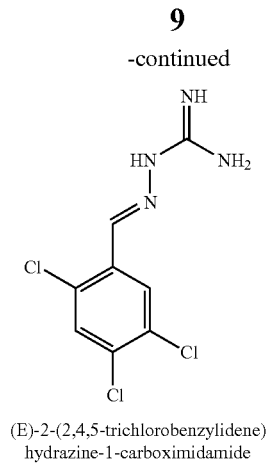

(E)-2-(2,4,5-trichlorobenzylidene)
hydrazine-1-carboximidamide

BRIEF DESCRIPTION OF THE FIGURES

Certain embodiments of the present invention will now be described, by way of example only, with reference to the drawings in which:
Figures FIG. 1 shows the selective binding of a R15B inhibitor of Example 1 to R15B-PP1 over R15A-PP1.

FIG. 2 shows that a selective R15B inhibitor of Example 1 induces a transient phosphorylation of eIF2α in cells in the absence of stress and induces expression of R15A in cells.

FIG. 3 shows that a selective R15B inhibitor of Example 1 protects cells from stress.

FIG. 4 shows the effects of a selective R15B inhibitor on eIF2α phosphorylation following stress. The compound of Example 1 prolongs eIF2α phosphorylation following stress.

FIG. 13 A. shows a cartoon illustrating the SPR method used to determine binding affinities of biotynilated guanabenz (Bio-GBZ) to R15A and R15B. B. SPR sensorgrams of R15A and R15B binding to bio-GBZ immobilized on the SPR sensor chip surface. R15A/B concentration=0.0244-12.5 μM.

FIG. 16 Alignments of human R15A and R15B. Although functionally related, R15A and R15B are different and share only 23% identity.

FIG. 21 shows the steady states affinities of GBZ to R15A-PP1c, R15B-PP1c and PP1c immobilized on SPR chips of the present invention. Binding of GBZ to R15A/PP1c (○) and R15B/PP1c (▲) immobilized on the streptavidin sensor chip surface. Response units were plotted against compound concentration to determine the steady-state binding constant ($K_D$). $K_D$ of GBZ for R15A is 0.1221 μM and no binding was detected for GBZ to R15B.

FIG. 22 shows the steady states affinities of Sephin1 to R15A-PP1c, R15B-PP1c and PP1c immobilized on SPR chips of the present invention. $K_D$ of Sephin1 for R15A is 0.786 μM and for R15B is 23 μM.

DETAILED DESCRIPTION OF THE INVENTION

Figure 5:
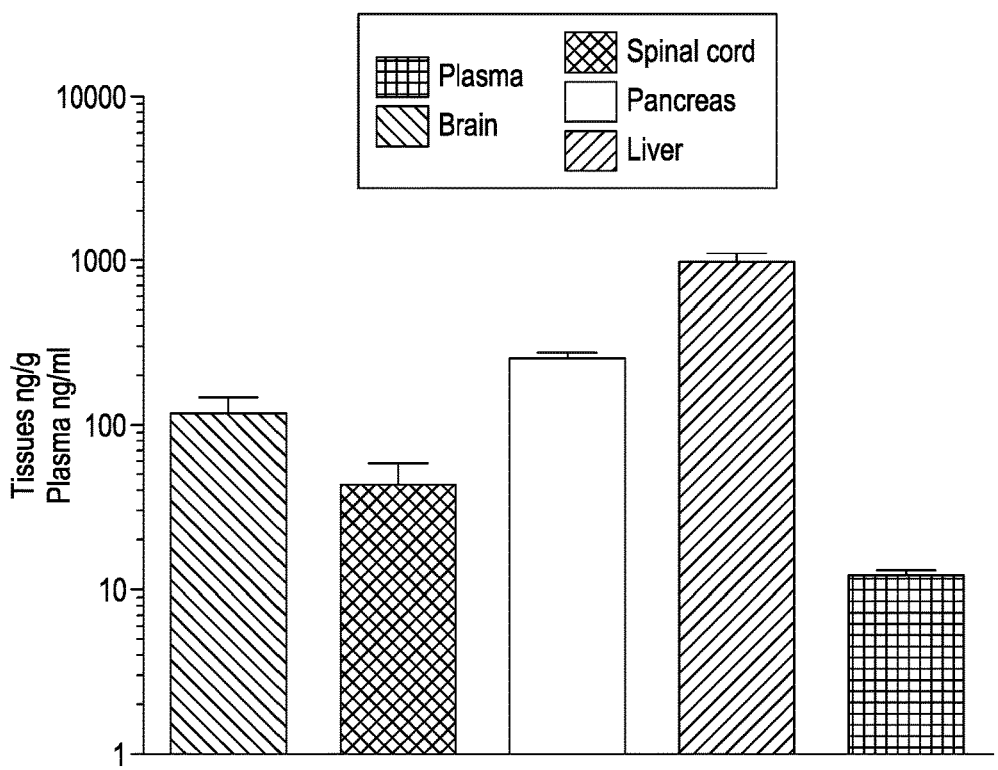
FIG. 5 shows the tissue distribution of a compound of Example 1 which exhibits extensive tissue distribution.

Phosphorylation of the α subunit of eIF2α is the first line of defense against a variety of stresses and is thereby a central component of two partly overlapping signaling pathways: the Unfolded Protein Response (UPR) and the Integrated Stress Response (ISR). To reverse eIF2α phosphorylation, mammalian cells have two eIF2α phosphatases. The eIF2α phosphatases are dimeric holoenzymes that share a catalytic subunit PP1c with about 200 other phosphatases, and are bound to one of two related regulatory subunits: PPP1R15A (Novoa et al., The Journal of Cell Biology, 153, 1345-1355, 2001), a stress inducible protein or PPP1R15B, which is constitutively expressed (Jousse et al., The Journal of Cell Biology, 163, 767-775, 2003).

PPP1R15A ("R15A") inhibition selectively inhibits the stress-induced eIF2α phosphatase composed of PPP1R15A and PP1, while sparing the highly related and constitutive phosphatase PPP1R15B-PP1. PPP1R15A inhibition prolongs eIF2α phosphorylation in stressed cells and this results in prolonging translation attenuation in stressed cells. As a consequence, chaperone availability is increased in stressed cells because the chaperones that are normally engaged in assisting the folding of newly synthetized proteins become available when translation is decreased. This favors protein folding and rescues cells from protein proteostasis defects. Thus, in principle, PPP1R15A inhibitors could treat mammalian diseases involving protein misfolding stress. Inhibition of PPP1R15A in mammals has an attractive therapeutic potential because inhibition of PPP1R15A is predicted to be safe as PPP1R15A/GADD34 knock-out mice are largely indistinguishable from wild-type mice (Marciniak et al., Genes & Development, 18, 3066-3077, 2004). However, the number of therapeutic indications that can be treated with PPP1R15A inhibitors is predicted to be restricted to diseases where PPP1R15A is expressed and where PPP1R15A is in the disease mode of action. Thus, inhibition of PPP1R15A may be powerful and safe but will be restricted to diseases involving PPP1R15A.

Regardless of the limitations associated with PPP1R15A inhibition, the approach of restoring proteostasis by fine tuning translation to increase chaperone availability is in theory powerful, straightforward and applicable to correct a broad range of diseases involving misfolded proteins. As noted above, the use of PPP1R15A inhibitors will most likely be restricted to diseases where PPP1R15A is expressed and where PPP1R15A is in the disease mode of action.

To widen the range of diseases for which selective PP1 inhibition may be used, the present invention seeks to provide a method to identify selective and/or non-selective PP1 inhibitors.

As used herein, the term "PPP1R15A inhibitor" refers to a selective inhibitor selected from the group consisting of polypeptides, polynucleotides, antibodies, peptides or small molecule compounds. The term "PPP1R15A" is used interchangeably with the term "R15A". Suitably, a "PPP1R15A inhibitor" is an inhibitor which is selective for R15A over R15B and/or PPIc. Assays for selective inhibition are described herein.

As used herein, the term "PPP1R15A and PPP1R15B inhibitor" refers to a selective inhibitor selected from the group consisting of polypeptides, polynucleotides, antibodies, peptides or small molecule compounds. Suitably, a "PPP1R15A inhibitor and PPP1R15B inhibitor" is an inhibitor which is binds to and/or inhibits both R15A and R15B. Assays for such inhibitors are described herein.

As used herein, the term "PPP1R15B inhibitor" refers to a selective inhibitor selected from the group consisting of polypeptides, polynucleotides, antibodies, peptides or small molecule compounds. The term "PPP1R15B" is used interchangeably with the term "R15B". Suitably, a "PPP1R15B inhibitor" is an inhibitor which is selective for R15B over R15A and/or PPIc. Assays for selective inhibition are described herein.

In one embodiment, a "selective inhibitor" may be defined as a compound where the difference in KD values between one holophosphatase, such as R15A or R15B, and another is in the region of 3 fold and, preferably greater than 3 fold, or even more preferably 10 or 20 fold.

Test Compounds

A test compound for use in an assay in accordance with any aspect of embodiment of the invention may be a protein or polypeptide, polynucleotide, antibody, peptide or small molecule compound. In one embodiment, the assay may encompass screening a library of test compounds e.g. a library of proteins, polypeptides, polynucleotides, antibodies, peptides or small molecule compounds. Suitable high throughput screening methods will be known to those skilled in the art. For example, high throughput SPR may be carried out using arrays.

Assay

In one embodiment, the invention is described with reference to assays for an inhibitor that is specific for R15B. However, it will be appreciated that the methods described herein are equally applicable to assays for identifying specific or non-specific inhibitors of holophosphatases more generally in accordance with any aspect or embodiment of the invention.

The inhibitors described herein in Examples 1 to 4 selectively bind to the PPP1R15B-PP1 complex but do not bind, or binding is significantly less, to the PPP1R15A-PP1 complex. Preferably, the PPP1R15B inhibitor exhibits a $K_D$ for the PPP1R15B-PP1 complex of 1 µM or less and exhibits binding 5 times greater, preferably 10 times greater, or even more preferably at least 20 times greater for the PPP1R15A-PP1 complex.

For example, the compound of Example 1 has a $K_D$ of 0.035 µM for PPP1R15B-PP1 and 1 µM for PPP1R15A-PP1 and the compound of Example 2 has a $K_D$ of 5 µM for PPP1R15A-PP1 and a $K_D$ of 0.143 µM for PPP1R15B-PP1. The compound of Example 2 had previously been thought to be a non-selective inhibitor (WO2014108520). However, previously it was not possible to measure $K_D$ values. With the novel assays described herein, the present inventors have established the $K_D$ values and revealed that, for the compound of Example 2, the difference in affinities is greater than 30 fold. Example 2 is therefore considered to be a selective inhibitor of PPP1R15B-PP1. Example 3 was found to have a $K_D$ of 0.149 µM for PPP1R15B-PP1 and 3.93 µM for PPP1R15A-PP1 and the compound of Example 4 was found to have a $K_D$ of 0.457 µM for PPP1R15A-PP1 and a $K_D$ of 0.022 µM for PPP1R15B-PP1.

In one embodiment of the invention, there is provided an assay for determining polypeptides, polynucleotides, antibodies, peptides or small molecule compounds which selectively inhibit PPP1R15B over PPP1R15A. In another embodiment, there is provided an assay for determining polypeptides, polynucleotides, antibodies, peptides or small molecule compounds which selectively inhibit PPP1R15A over PPP1R15B. In a further embodiment, there is provided an assay for determining polypeptides, polynucleotides, antibodies, peptides or small molecule compounds which inhibit both PPP1R15B and PPP1R15A.

Selective binding may be to either PPP1R15B alone or to PPP1R15B in a complex with PP1. Likewise, selective binding may be to either PPP1R15A alone or to PPP1R15A in a complex with PP1.

In another embodiment, there is provided a competitive binding assay wherein the assay comprises contacting a compound disclosed herein with PPP1R15B and a candidate polypeptide, polynucleotide, antibody, or fragment thereof, peptide, or small molecule compound and detecting any change in the interaction between the compound and PPP1R15B.

Alternatively, the competitive binding assay may comprise contacting a compound disclosed herein with PPP1R15B in the presence of a known substrate of PPP1R15B and detecting any change in the interaction between PPP1R15B and said known substrate.

Optionally, the assay is used as a screen or a high throughput screen (HTS).

Whilst a binding assay can be used to screen for candidates selectively binding to PPP1R15B, the properties of a candidate are not necessarily predicted by a binding assay. Other assays are therefore needed to assess whether the candidate inhibits PPP1R15B function or not.

In another embodiment of the invention there is provided a suite of assays for determining the selective inhibition of PPP1R15B or PPP1R15A of a candidate selected from a polypeptide, polynucleotide, antibody, peptide or small molecule compound, wherein the assay comprises the steps of:
i) treating mammalian cells with the candidate;
ii) monitoring eIF2α phosphorylation over time;
wherein transient induction of eIF2α phosphorylation indicates selective inhibition of PPP1R15B or PPP1R15A.

Optionally, the assay is used as a high throughput screen. For example, eIF2α phosphorylation can be detected by a method suitable for a HTS such as, but not limited to, immunological detection of eIF2α phosphorylation (e.g. the AlphaScreen® SureFire™ Phospho-eIF2α (Ser51) Assay).

A selective PPP1R15B inhibitor induces a transient eIF2α phosphorylation because eIF2α is ultimately dephosphorylated by PPP1R15A. Thus screening for compounds that only transiently induce eIF2α phosphorylation will lead to the identification of selective PPP1R15B inhibitors. Alternatively, any other method to monitor eIF2α phosphorylation directly or indirectly can be used in a HTS. For example: monitoring translation rates will mirror eIF2α phosphorylation; a selective PPP1R15B inhibitor will only transiently reduce translation rates and this property can be used in a HTS to identify selective PPP1R15B inhibitor. As eIF2α phosphorylation induces ATF4, PPP1R15A and CHOP these genes or proteins can be used as reporters in a screen to identify selective PPP1R15B inhibitors under the conditions described herein where eIF2α phosphorylation is only transient.

In one embodiment, the candidate compound is generated by conventional SAR modification of a compound of any of Examples 1 to 4.

In another embodiment, the PPP1R15B inhibitor is capable of protecting cells from stress by at least 20%, more preferably at least 30%, even more preferably at least 40%, at least 50%, at least 60%, at least 70%, at least 80%, and more preferably still, by at least 90%.

For example, the inhibitor of Example 1 protects cells from cytotoxic ER stress caused by tunicamycin. Cytoprotection against ER stress can be measured by any suitable assay. For example, cytoprotection can be measured in HeLa cells in which ER stress is elicited by the addition of media containing tunicamycin, a drug that blocks N-glycosylation, thereby preventing protein folding and inducing the unfolded protein response. Cell viability can be detected in the presence and absence of PPP1R15B inhibitor after a set period of time, by measuring the reduction of WST-8 into formazan using a standard cell viability kit (such as Cell Viability Counting Kit-8 from Dojindo). Cytoprotection from ER stress is measured in terms of the percentage increase in viable cells (relative to control) after ER stress.

By extension, a compound of Example 1 is capable of protecting cells against tunicamycin-induced stress but also other types of stresses such as, but not restricted to, stress induced by thapsigargin, stress caused by misfolding of proteins, amino acid analogues (for example azetidine, canavanine), reducing agents (DTT) and oxidative stress.

Cytoprotection from stress can be used to identify further PPP1R15B inhibitors. Optionally, the assay is used as a high throughput screen. For example, HTS can be used to measure cell survival under stress in order to identify new PPP1R15B inhibitors.

In one embodiment, there is provided a comparative cell viability assay to determine selectively of a PPP1R15B inhibitor comprising the steps of i) treating PPP1R15A and PPP1R15B knock-out cells with the PPP1R15B inhibitor, and then ii) comparing with the viability of wild-type, PPP1R15A and PPP1R15B knock-out cells.

This assay is analogous to the assay used to demonstrate selectivity of PPP1R15A inhibitors. Cells lacking either PPP1R15A or PPP1R15B activity are viable while cells lacking both the constitutive (PPP1R15B-PP1) and the stress-induced (PPP1R15A-PP1) eIF2α phosphatase are not viable (Harding et al., Proc. Natl. Acad. Sci. U.S.A., 106, 1832-1837, 2009; Tsaytler et al., Science, 332, 91-94, 2011). PPP1R15A and PPP1R15B knock-out cells have been used to evaluate the selectivity of a PPP1R15A inhibitor. Guanabenz reduces the viability of cells lacking PPP1R15B because the lack of both PPP1R15A and PPP1R15B activity is deleterious (Tsaytler et al., FEBS Journal, 280, 766-770, 2011). Thus, the inventors have reasoned that the selectivity of PPP1R15B inhibitors could be revealed in cells by comparing the viability of wild-type, PPP1R15A and PPP1R15B knock-out cells following a treatment with PPP1R15B inhibitors. Inactivation of both PPP1R15A and PPP1R15B is lethal (Harding et al., Proc. Natl. Acad. Sci. U.S.A., 106, 1832-1837, 2009). Thus, cells lacking PPP1R15A activity which have been treated with a PPP1R15B inhibitor selectively reduce their viability which confirms the presence of a selective PPP1R15B inhibitor.

This cell viability assay can be used for a HTS to identify other PPP1R15B inhibitors which will be selectively toxic to cells lacking PPP1R15A or where PPP1R15A has been inhibited. Such cells can be generated by conventional gene inactivation method (knock-out, Crispr/Cas9, siRNA for example). Alternatively, PPP1R15A can be pharmacologically inhibited with Guanabenz or any other selective PPP1R15A inhibitor. A selective PPP1R15B inhibitor will reduce viability of cells treated with a PPP1R15A inhibitor to a greater degree than cells treated with PPP1R15B inhibitor only.

Phosphatase activity assays may also be used to screen for PPP1R15B inhibitors.

In one embodiment, the invention describes a method to identify selective phosphatase inhibitors.

Kits and Apparatus

In other aspects or embodiments of the invention, kits and/or apparatus arranged for use and/or when used for a screening method in accordance with the invention are provided. Suitable kits and/or apparatus may include SPR chips or other solid surfaces generated to "display" a first and/or second holophosphatase through surface attachment to a chip or solid surface, e.g. a bead or microtitre plate. Suitably a chip or bead may be arranged in such a way as to enable the screening method as described herein to be carried out. Accordingly, in another aspect there is provided a kit for use in a method of screening in accordance with any aspect of embodiment of the invention. Suitably said kit may comprise a first holophosphatase captured onto a first surface and a second holophosphatase captured onto a second surface. Such first and/or second surfaces may be chips or beads suitable for analysis of a binding reaction by SPR. In one embodiment, the kit or apparatus in accordance with this aspect of the invention is one when used for a screening method as described herein.

Therapeutic Applications

Inhibitors identified using an assay in accordance with any aspect or embodiment of the invention, including inhibitors of PPP1R15A and/or PPP1R15B have potential therapeutic applications in treating and preventing various diseases and disorders. Inhibition of eIF2α dephosphorylation decreases translation and as a result, increases the availability of chaperones to favour folding.

Figure 11:
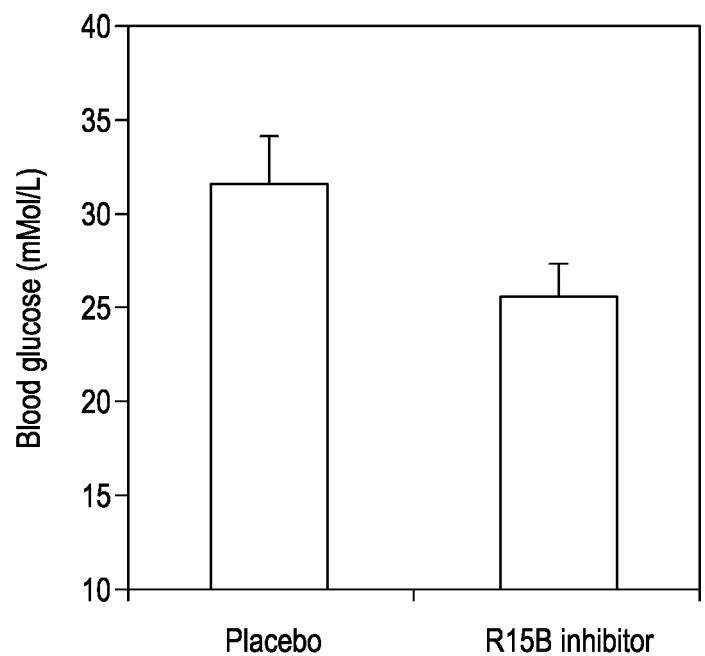
FIG. 11 shows blood glucose levels in obese mice db/db animals (n=5 per condition) following treatment with compound of Example 1.

The inventors have shown, for example, that:
  a PPP1R15B inhibitor (exemplified by the compound set out in Example 1) has good tissue distribution;
  PPP1R15B inhibition is safe in a mammal (FIG. 5, 6, 7);
  inhibition of PPP1R15B prevents a disease in a mammal (FIG. 9); and
  inhibition of PPP1R15B reduces a metabolic disorder in a mammal (FIG. 11).

One aspect of the invention relates to PPP1R15B inhibitors for use in therapy.

Another aspect of the invention relates to a method of treating a subject having a disease state alleviated by the inhibition of PPP1R15B, wherein the method comprises administering to the subject a therapeutically effective amount of a PPP1R15B inhibitor.

A further aspect of the invention relates a method of preventing a disease state alleviated by the inhibition of PPP1R15B in a subject, wherein the method comprises administering to the subject a therapeutically effective amount of a PPP1R15B inhibitor.

Another aspect of the invention relates to PPP1R15B inhibitors for use in the treatment or prevention of a disease state alleviated by the inhibition of PPP1R15B.

Yet another aspect of the invention relates to use of a PPP1R15B inhibitor in the manufacture of a medicament for the treatment or prevention of a disease state alleviated by the inhibition of PPP1R15B.

PPP1R15B related diseases are diseases that can be ameliorated by inhibiting PPP1R15B. These include disorders associated with accumulation of misfolded proteins or perturbation of protein homeostasis (proteostasis) such as Huntington's disease and other polyglutamine disorders, Parkinson's disease, Alzheimer's disease, ataxias and other polyglutamine disorders as well as retinal degeneration, glaucoma, amyotrophic lateral sclerosis (ALS) and prion diseases; disorders associated with aggregation of the microtubule-associated protein tau and include Alzheimer's disease, amyotrophic lateral sclerosis and parkinsonism-dementia complex, argyrophilic grain disease, chronic traumatic encephalopathy, corticobasal degeneration, diffuse neurofibrillary tangles with calcification (DNTC), Down's syndrome, familial British dementia (FBD), familial Danish dementia (FDD), frontotemporal dementia and parkinsonism linked to chromosome 17 (FTDP-17), frontotemporal lobar degeneration (FTLD), Gerstmann-Sträussler-Scheinker disease, Gaudeloupean parkinsonism, myotonic dystrophy, neurodegeneration with brain iron accumulation, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, SLC9A6-related mental retardation, subacute sclerosing panencephalitis, tangle-only dementia, and white matter tauopathy with globular glial inclusions; myelin disorders, such as multiple sclerosis, Pelizaeus-Merzbacher disease, vanishing white matter disease, acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, diffuse white matter injury, Guillain-Barre Syndrome, central pontine myelinolysis, inherited demyelinating diseases such as leukodystrophy, and Charcot Marie Tooth disease; diseases caused by the misfolding or trafficking defects of any protein made in the endoplasmic reticulum (ER), such as cystic fibrosis, congenital hypothyroid goiter, familial neurohypophyseal diabetes, procollagen biosynthesis disorders including osteogenesis imperfect, hypercholesterolemia, alpha-1 antitrypsin deficiencies, lysosomal disorder, retinis pigmentosa (RP), and inflammatory bowel disease; metabolic diseases, such as diabetes, Wolcott-Rallison syndrome, obesity, insulin resistance, hyperlipidemia, fatty liver disease and atherosclerosis; and other disorders including rheumatoid arthritis, type-1 diabetes and vitiligo.

In one preferred embodiment, an inhibitor of PPP1R15B, such as but not restricted to a compound of any of Examples 1 to 4, is for use in treating disorders associated with pathological UPR or ISR and/or defects in protein homeostasis.

In one embodiment the PPP1R15B inhibitor has the structure of the compound of any of Examples 1 to 4.

In one embodiment, the PPP1R15B inhibitor has the structure of the compound of Example 1.

In another embodiment, the PPP1R15B inhibitor has the structure of the compound of Example 2.

In a further embodiment, the PPP1R15B inhibitor has the structure of the compound of Example 3.

In yet another embodiment, the PPP1R15B inhibitor has the structure of the compound of Example 4.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "therapeutically effective amount" refers to that amount of the compound being administered which will relieve to some extent one or more of the symptoms of the disease of disorder being treated.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

The phrase "manufacture of a medicament" includes the above described compound directly as the medicament in addition to its use in a screening programme for further active agents or in any stage of the manufacture of such a medicament.

Diseases with Potential Protein or Peptide Misfolding and/or Aggregation in Their Mode of Action Disease-causing proteins are expressed throughout life but degenerative diseases are mostly late-onset. This suggests that the different disease-causing proteins gradually become detrimental over time. While it is now well established that misfolded proteins cause distinct degenerative diseases, why they accumulate remains largely unclear. Cells normally strive to ensure that proteins are correctly folded and indeed all cells have powerful and sophisticated protein quality control systems that very efficiently handle potentially harmful proteins for decades. However, the protein quality control mechanisms seem to gradually fail with age, leading to the accumulation of misfolded proteins with the resulting catastrophic consequences for cells and organisms. These misfolded/aggregated proteins or peptides can be present inside or outside the cell and can be found at any location. In principle, boosting the natural cellular defenses against misfolded proteins should represent a generic approach to reduce the pathology in diverse protein misfolding diseases where misfolded/aggregation prone proteins are present in the pathology. The present invention describes such an approach and demonstrates both its safety and efficacy in a mammal.

Neurodegenerative diseases such as Alzheimer's disease (AD), Parkinson's disease (PD), Huntington's disease (HD), ataxias and other polyglutamine disorders, tauopathies as well as, retinal degeneration, glaucoma, amyotrophic lateral sclerosis (ALS) and prion diseases are devastating and affect an increasing number of individuals in the ageing population. These diseases are clinically diverse but share a common mechanism. They are caused by the progressive dysfunction and death of specific nerve cells in selective regions of the brain due to the accumulation of specific proteins of aberrant shape. The misfolded and aggregation prone proteins include, but are not restricted to: Aβ42, α-synuclein, TAU, TDP-43, TLS/FUS, SOD1, Huntingtin and other proteins with polyglutamine expansion, prions and the translation product(s) of C9ORF72.

The Applicant has demonstrated that the compound of Example 1 selectively inhibits PPP1R15B-PP1, correcting a protein misfolding disease in mice. Inhibitors of PPP1R15B described in the present invention therefore have therapeutic applications in the treatment of a variety of diseases where a misfolded protein is involved and in particular with an accumulation of misfolded proteins.

As an example, the Applicant has shown that the compound of Example 1 ameliorates Huntington's disease in a mammal. Thus, without wishing to be bound by theory, it is believed that an inhibitor of PPP1R15B such as but not restricted to, a compound of any of Examples 1 to 4, has a protective effect against diverse diseases caused by misfolded/aggregated proteins such as but not restricted to Alzheimer's disease (AD), Parkinson's disease (PD), Huntington's disease (HD), ataxias and other polyglutamine disorders as well as, retinal degeneration, glaucoma, Amyotrophic Lateral Sclerosis (ALS), tauopathies and prion diseases.

The present invention provides for the therapy of polyglutamine disorders. Huntington's disease belongs to a broader group of disorders, "polyglutamine disorders", characterized by expansion of CAG codons translated in glutamine in unrelated proteins. Huntington's disease is caused by an expansion in the gene encoding Huntingtin; Spinal and bulbar muscular atrophy, Dentalorubral-pallidoluysian atrophy, and Spinocerebellar ataxias are caused by expansion in genes encoding Androgen Receptor, Atrophin 1, Ataxin 1, 2, 3, α-voltage dependent calcium channel subunit and TBP respectively. CAG expansion is translated in polyglutamine and causes aggregation of the affected protein. Accordingly, prevention and/or treatment of polyglutamine disorders such as these are within the scope of the invention.

The diseases include any diseases where misfolding/aggregation is involved with the proteins known today and described above but will also apply to new proteins and perhaps new diseases in the future.

In a preferred embodiment, the invention provides for the therapy of proteostasis diseases.

In another embodiment, an inhibitor of PPP1R15B such as but not restricted to, a compound of any of Examples 1 to 4, is for use in treating a disease where accumulation of misfolded proteins is involved in the mode of action.

In a further embodiment, the disease or disorder is Alzheimer's disease (AD), Parkinson's disease (PD), Huntington's disease (HD), ataxias or other polyglutamine disorder, retinal degeneration, glaucoma, Amyotrophic Lateral Sclerosis (ALS), tauopathies or a prion disease.

In a particular embodiment, a compound of any of Examples 1 to 4 is for use in the treatment of Huntington's disease.

In another particular embodiment, the compound any of Examples 1 to 4 is for use in the treatment of Parkinson's disease.

In one embodiment, the disease or disorder is associated with aggregation of the microtubule-associated protein tau.

The Applicant has demonstrated that the compound of Example 1 selectively inhibits PPP1R15B-PP1, correcting a protein misfolding disease in mice. PPP1R15B inhibitors can also be useful to prevent or stop the progression of diseases that are caused by the same mechanism: accumulation of misfolded proteins.

Examples of such diseases include, Alzheimer's disease, amyotrophic lateral sclerosis, parkinsonism and dementia, argyrophilic grain disease, chronic traumatic encephalopathy, corticobasal degeneration, diffuse neurofibrillary tangles with calcification (DNTC), Down's syndrome, familial British dementia (FBD), familial Danish dementia (FDD), frontotemporal dementia and parkinsonism linked to chromosome 17 (FTDP-17) (caused by MAPT mutations), frontotemporal lobar degeneration (FTLD) (some cases caused by C9ORF72 mutations), Gerstmann-Sträussler-Scheinker disease, Gaudeloupean parkinsonism, myotonic dystrophy, neurodegeneration with brain iron accumulation, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, SLC9A6-related mental retardation, subacute sclerosing panencephalitis, tangle-only dementia, white matter tauopathy with globular glial inclusions.

In one embodiment, the disease is a myelin disorder.

Myelin is an abundant protein of both the central and peripheral nervous system. It is produced by two cell types: oligodendrocytes in the central nervous system and Schwann cells in the peripheral nervous system. Myelin forms a sheath around axons to insure the speed of conduction of electrical impulses along an axon, and to prevent electrical current from dissipating from the axon. Myelin function is essential for the nervous system.

Myelin disorders affect more than 2.5 million people worldwide and are defined as any disease associated with damage in myelin. Myelin disorders are manifested by diverse symptoms including but not restricted to motor impairments, sensory impairments, cognitive dysfunction, emotional disturbances, and impaired coordination.

There are many demyelinating disorders, the most common of which is multiple sclerosis (MS). Multiple sclerosis is an autoimmune disease affecting the brain and spinal cord resulting in demyelination in the brain. In addition to MS, other demyelinating disorders include but are not limited to Pelizaeus-Merzbacher disease and vanishing white matter disease, acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathy, anti-MAG peripheral neuropathy, adrenoleukodystrophy, adrenomyeloneuropathy, diffuse white matter injury, Guillain-Barre Syndrome, central pontine myelinolysis, inherited demyelinating diseases such as leukodystrophy, and Charcot Marie Tooth (CMT) disease.

CMT disease is a group of myelin neuropathies caused by mutations in a number of genes. Mutations in the peripheral myelin protein PMP22 are the most common causes of CMT. A mutation in PMP22 (Trembler-J) causes the misfolding of PMP22 and results in a disease in mice that resembles CMT in human due to defects in myelin in the peripheral nervous system. The Applicants have demonstrated that the compound of Example 1 can improve myelination in explants from neuropathic mice. The Applicants have demonstrated that improving myelination in explants from neuropathic mice predicts efficacy in a mammal (Das et al. in press). Therefore the compound of Example 1 will be useful in treating CMT in mammals and other myelin disorders where it is known that the mechanisms are similar and involve the eIF2α pathway (Lin and Popko, Nat. Neurosci., 12, 379-385, 2009).

In one embodiment, an inhibitor of R15B is for use in treating a myelin disorder.

In another embodiment, an inhibitor of PPP1R15B, such as but not restricted to a compound of any of Examples 1 to 4, is for use in treating Charcot Marie Tooth disease.

In a further embodiment, a PPP1R15B inhibitor of the present invention is for use in treating myelin disorders of the central nervous system, for example, multiple sclerosis. It is known that the mechanisms of CMT and MS are similar with an exhaustion of myelin producing cells (Schwann cells in CMT and oligodendrocytes in MS) and involve pathological signalling of the eIF2α-RRR1R15A pathway (Lin and Popko, Nat. Neurosci., 12, 379-385, 2009). Since the Applicants have demonstrated that Example 1 is effective in a myelinopathy and have also demonstrated the bioavailability of a compound of Example 1 in both the central and peripheral nervous system (FIG. 5), it is anticipated that PPP1R15B inhibitors will be useful in treating multiple sclerosis.

In one embodiment, the disease is a disease arising as a consequence of a mutation in a protein resulting in its misfolding and mislocalization or trafficking defects.

The Applicants have demonstrated that the compound of Example 1 can rescue defects caused by one misfolded protein, PMP22, synthetized in the endoplasmic reticulum (ER). Due to the mechanism of action (decreasing translation to increase folding) an inhibitor of PPP1R15B, in accordance with the present invention, will also be useful for the treatment of diseases due to the misfolding or trafficking defects of any protein made in the ER, including transmembrane or secreted proteins.

Examples of such diseases include: cystic fibrosis caused by mutations impairing folding of the transmembrane protein (CFTR); congenital hypothyroid goiter with thyroglobulin deficiency due to the misfolding and/or trafficking defect of the hormone thyroglobulin; familial neurohypophyseal diabetes insipidus caused by misfolding and absence of circulating arginine vasopressin (this may also include certain forms of genetically inherited nephrogenic diabetes insipidus); procollagen biosynthesis disorders where the disease is caused by a failure to fold, assemble and synthetize collagen, such as, but not restricted to, osteogenesis imperfect; more generally, any genetic diseases of connective tissues where protein misfolding/lack of synthesis or mislocalization is in the mode of action such as growth plate dysplasia associated with defects of proteins from extracellular matrix; hypercholesterolemia, with molecular defects caused by mutations in the LDL receptor causing lack of synthesis, altered intracellular transport, or abnormal function; Alpha-1 antitrypsin deficiencies due to the misfolding of alpha 1 antitrypsin; lysosomal disorder due to misfolding of proteins associated for lysosomal function such as Gaucher disease and Niemann-Pick disease and Anderson-Fabry disease; retinis pigmentosa (RP), which is the most common form of hereditary retinal degeneration caused by the misfolding of rhodopsin proteins, their ER retention and the resulting ER stress and cell death; and inflammatory bowel disease which is associated with ER stress.

For the same seasons, an inhibitor of PPP1R15B according to the invention can be used to treat the following disorders, associated with pathological UPR and/or defects in a transmembrane protein (Lin and Popko, Nat. Neurosci., 12, 379-385, 2009). These disorders include, but are not restricted to Pelizaeus-Merzbacher disease associated with mutations in the membrane proteolipid protein (PLP) gene, and vanishing white matter (VWM) disease as well as multiple sclerosis, a common myelin disorder.

In one embodiment, the invention relates to PPP1R15B inhibitors for use in the treatment of diseases arising from a mutation in a protein resulting in the protein's misfolding and mislocalization or trafficking defects.

In a another embodiment, the disease arising from a mutation in a protein resulting in the protein's misfolding and mislocalization or trafficking defects is selected from cystic fibrosis, congenital hypothyroid goiter, familial neurohypophyseal diabetes insipidus, procollagen biosynthesis disorders such as osteogenesis, hypercholesterolemia, alpha-1 antitrypsin deficiencies, lysosomal disorders such as Gaucher disease, Niemann-Pick disease and Anderson-Fabry disease, retinis pigmentosa and inflammatory bowel disease.

In one embodiment, the disease is a metabolic disease.

It is known that metabolic diseases such as diabetes, obesity, insulin resistance, hyperlipidemia, fatty liver disease, and atherosclerosis are associated with pathological ER stress and it is believed that pharmacological modulators of the UPR may have therapeutic benefit (Cao and Kaufman, 2012, Curr Biol, vol. 22 (16)). However, as no PPP1R15B inhibitors were previously available and PPP1R15B inhibition was predicted to be deleterious, and furthermore, since it is challenging to inhibit phosphatases, it was unclear whether PPP1R15B could be a therapeutic target in metabolic diseases.

The inventors have demonstrated that the compound of Example 1 can ameliorate a metabolic disorder in a mammal (FIG. 11). Therefore, PPP1R15B inhibitors will be useful to treat metabolic disorders such as, but not restricted to diabetes, obesity, fatty liver disease, and atherosclerosis.

In one embodiment, the PPP1R15B inhibitors described herein are for use in the treatment of metabolic disorders.

In a preferred embodiment, the metabolic disorder is selected from diabetes, obesity, fatty liver disease, and atherosclerosis.

PPP1R15B selective inhibitors are also useful in the treatment of other disorders including rheumatoid arthritis, diabetes, Wolkott Rallison syndrome, inflammatory bowel disease and vitiligo, which involve UPR in their mechanism of action (Cao and Kaufman, 2012, Curr Biol, vol. 22 (16)).

Reducing protein synthesis has been described to increase life span (see, for example, Tavernarakis, N. (2008). (Ageing and the regulation of protein synthesis: a balancing act? *Trends Cell Biol*, 18(5), 228-235. http://doi.org/10.1016/j.tcb.2008.02.004.). Those compounds in accordance with the invention that have been demonstrated to reduce protein synthesis by inhibiting R15B may therefore be used in treatments for increasing life-span/reducing ageing.

Compounds

In one embodiment of the invention, there is provided compounds of Examples 1 to 4, and their use as PPP1R15B selective inhibitors:

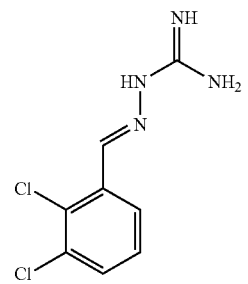

Example 1

(E)-2-(2,3-dichlorobenzylidene)hydrazine-1-carboximidamide

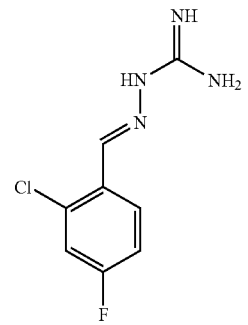

Example 2

(E)-2-(2-chloro-4-fluorobenzylidene)hydrazine-1-carboximidamide

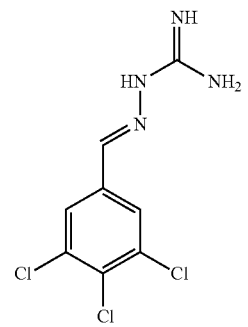

Example 3

(E)-2-(3,4,5-trichlorobenzylidene)hydrazine-1-carboximidamide

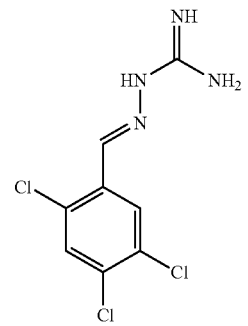

Example 4

(E)-2-(2,4,5-trichlorobenzylidene)hydrazine-1-carboximidamide

The compounds described herein advantageously exhibit no activity toward the adrenergic α2A receptor relative to prior art compounds such as Guanabenz. This loss in alpha-2 adrenergic activity renders the compounds therapeutically useful in the treatment of the diseases and disorders disclosed herein. In contrast, Guanabenz derivatives with adrenergic activity cannot be used therapeutically because this causes side effects such as hypotension, drowsiness, lethargy and even coma. (Hallet al. *Ann Intern Med* 102, 787-788, 1985). The absence of alpha-2 adrenergic activity means that the compounds of the invention can be administered at a dosage suitable to treat the aforementioned diseases, without any significant effect on blood pressure.

Salts and Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al., J Pharm Sci, 66, 1-19 (1977). Salts which are not pharmaceutically or veterinarily acceptable may still be valuable as intermediates.

Esters are formed either using organic acids or alcohols/hydroxides, depending on the functional group being esterified.

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art. Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3rd edition, ed. March, J., John Wley and Sons, N.Y., 1985).

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of Examples 1 to 4 where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to any of the exemplified compounds in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Antibodies

References to "antibody" include but are not limited to monoclonal, human, humanized or chimaeric antibodies. The antibody may be an antibody fragment including a VH or VL domain or a single chain antibody molecule (scFv). In one embodiment the antibody is human.

Pharmaceutical Compositions

According to a further aspect of the invention there is provided a pharmaceutical composition comprising a PPP1R15B inhibitor. In one embodiment, the pharmaceutical composition is for use in therapy combined with any pharmaceutically acceptable carrier, adjuvant or vehicle.

The term "pharmaceutical composition" in the context of this invention means a composition comprising an active agent, or a pharmaceutically acceptable salt thereof, and additionally one or more pharmaceutically acceptable excipients.

Suitable pharmaceutically acceptable excipients are known to those skilled in the art and generally include an acceptable composition, material, carrier, diluent or vehicle suitable for administering a PPP1R15B inhibitor of the invention to an animal.

In one embodiment the animal is a mammal. In another embodiment the mammal is human.

Pharmaceutical formulations include those suitable for oral, topical (including dermal, buccal, ocular and sublingual) rectal or parenteral (including subcutaneous, intradermal, intramuscular and intravenous), nasal, intra-ocularly and pulmonary administration e.g., by inhalation. The formulation may, where appropriate, be conveniently presented in discrete dosage units and may be prepared by any of the methods well known in the art of pharmacy.

Dosages may be varied depending on the requirements of the patient, the severity of the condition being treated and the characteristics of the active ingredient being employed. Determination of the effective dose is within the remit of the skilled person, without undue burden. Suitable dosage forms for administration to mammals, including humans are typically in the range of up to 100 mg/kg body weight, or may be 0.1 mg/kg, 10 mg/kg, 20 mg/kg, 30 mg/kg for example.

According to a further aspect of the invention, there is provided a process for the preparation of a pharmaceutical composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound disclosed herein in conjunction or association with a pharmaceutically acceptable carrier or vehicle. All methods include the step of bringing into association an active compound with liquid carriers or finely divided solid carriers or both and then, if necessary, shaping the product into the desired formulation.

In one aspect, there is provided a use of a PPP1R15B inhibitor as described herein in the manufacture of a medicament for use in the treatment of a disease or disorder alleviated by the selective inhibition of PPP1R15B.

Combinations

In a particularly preferred embodiment, the one or more PPP1R15B inhibitors of the invention are administered in combination with one or more other active agents, for example, existing drugs available on the market. In such cases, the inhibitors of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of resistance.

Beneficial combinations may be suggested by studying the inhibitory activity of the test inhibitors with agents known or suspected of being valuable in the treatment of a particular disorder. This procedure can also be used to determine the order of administration of the agents, i.e. before, simultaneously, or after delivery. Such scheduling may be a feature of all the active agents identified herein.

In another aspect or embodiment, the present invention relates to PPP1R15B selective inhibitors and methods of screening for PPP1R15B selective inhibitors. The invention further relates to compounds which selectively inhibit PPP1R15B and their use in therapy.

Accordingly, further aspects and embodiments of the invention are provided in the following numbered clauses provided as statements of invention:

1. An assay method for identifying and/or determining polypeptides, polynucleotides, antibodies, peptides or small molecule compounds which selectively bind PPP1R15B over PPP1R15A.

2. The assay according to clause 1, wherein the assay is a competitive binding assay comprising contacting a PPP1R15B selective inhibitor with PPP1R15B and a candidate polypeptide, polynucleotide, antibody, peptide or small molecule compound and detecting any change in the interaction between the PPP1R15B selective inhibitor and PPP1R15B.

3. The assay according to clause 2, wherein the assay is used as a screen or high throughput screen.

4. An assay for determining the selective inhibition of PPP1R15B of a candidate selected from a polypeptide, polynucleotide, antibody, peptide or small molecule compound, wherein the assay comprises the steps of:
   i) treating mammalian cells with the candidate;
   ii) monitoring eIF2α phosphorylation over time;
   wherein transient induction of eIF2α phosphorylation indicates selective inhibition of PPP1R15B.

5. The assay according to clause 4, wherein the assay is used as a high throughput screen.

6. A cell viability assay for determining selectivity of a PPP1R15B inhibitor comprising the steps of:
   i) treating cells with the PPP1R151B inhibitor;
   ii) comparing viability with the viability of wild-type, PPP1R151A and PPP1R15B knock-out cells;
   wherein a reduction in viability in the treated cells indicates the presence of a PPP1R15B selective inhibitor.

7. An assay for determining the selective inhibition of PPP1R15B of a candidate selected from a polypeptide, polynucleotide, antibody, peptide or small molecule compound, wherein the assay comprises the steps of:
   i) treating mammalian cells or organisms with the candidate;
   ii) monitoring PPP1R15A over time;
   wherein transient induction PPP1R15A indicates selective inhibition of PPP1R15B.

8. A selective PPP1R15B inhibitor for use in therapy.

9. A selective PPP1R15B inhibitor for use in the prevention or treatment of a disease or disorder alleviated by the selective inhibition of PPP1R15B.

10. A selective PPP1R15B inhibitor for use according to clause 9, wherein the disease or disorder is a proteostasis disease.

11. A selective PPP1R15B inhibitor for use according to clause 10, wherein the proteostasis disease is Huntington's disease, Parkinson's disease, Alzheimer's disease, a tauopathy, ataxias, retinal degeneration, glaucoma, amyotrophic lateral sclerosis (ALS) or a prion disease.

12. A selective PPP1R15B inhibitor for use according to clause 11, wherein the disease is Huntington's disease.

13. A selective PPP1R15B inhibitor for use according to clause 11, wherein the disease is Parkinson's disease.

14. A selective PPP1R15B inhibitor for use according to clause 11, wherein the disease is a tauopathy.

15. A selective PPP1R15B inhibitor for use according to clause 9, wherein the disease is a protein trafficking disease.

16. A selective PPP1R15B inhibitor for use according to clause 9, wherein the disease or disorder is a myelin disorder.

17. A selective PPP1R15B inhibitor for use according to clause 16, wherein the myelin disorder is multiple sclerosis, Pelizaeus-Merzbacher disease, vanishing white matter disease, acute disseminated encephalomyelitis, periventricular leukomalacia, periventricular white matter injury, Tabes Dorsalis, Devic's disease, optic neuritis, progressive multifocal leukoencephalopathy, transverse myelitis, chronic inflammatory demyelinating polyneuropathyl, anti-MAG peripheral neuropathy, adrenoleukodystrophy, adrenomyeloneuropathy, diffuse white matter injury, Guillain-Barre Syndrome, central pontine myelinolysis, leukodystrophy or Charcot Marie Tooth disease.

18. A selective PPP1R15B inhibitor for use according to clause 9, wherein the disease or disorder is cystic fibrosis, congenital hypothyroid goitre, familial neurohypophyseal diabetes, a procollagen biosynthesis disorder including osteogenesis imperfect, hypercholesterolemia, an alpha-1 antitrypsin deficiency, lysosomal disorder, retinis pigmentosa or inflammatory bowel disease.

19. A selective PPP1R15B inhibitor for use according to clause 9, wherein the disease or disorder is a metabolic disease.

20. A selective PPP1R15B inhibitor for use according to clause 19, wherein the metabolic disease is diabetes, Wolcott Rallison syndrome, obesity, insulin resistance, hyperlipidemia, fatty liver disease or atherosclerosis.

21. A selective PPP1R15B inhibitor for use according to clause 9, wherein the disease or disorder is rheumatoid arthritis, type-1 diabetes or vitiligo.

22. A selective PPP1R15B inhibitor for use according to clause 9, wherein the disease or disorder is associated with aggregation of the microtubule-associated protein tau.

23. A method of treating a subject having a disease state alleviated by the inhibition of PPP1R15B, wherein the method comprises administering to the subject a therapeutically effective amount of a PPP1R15B inhibitor.

24. An assay according to any one of clauses 1 to 4, inhibitor for use according to any one of clauses 8 to 22 or method of treatment according to clause 23, wherein the PPP1R15B selective inhibitor is a compound selected from:
(E)-2-(2,3-dichlorobenzylidene)hydrazine-1-carboximidamide;
(E)-2-(2-chloro-4-fluorobenzylidene)hydrazine-1-carboximidamide;
(E)-2-(3,4,5-trichlorobenzylidene)hydrazine-1-carboximidamide; and
(E)-2-(2,4,5-trichlorobenzylidene)hydrazine-1-carboximidamide.

25. A selective PPP1R15B inhibitor for use in the treatment of Huntington's disease, wherein the inhibitor is a compound selected from:
(E)-2-(2,3-dichlorobenzylidene)hydrazine-1-carboximidamide;
(E)-2-(2-chloro-4-fluorobenzylidene)hydrazine-1-carboximidamide;
(E)-2-(3,4,5-trichlorobenzylidene)hydrazine-1-carboximidamide; and
(E)-2-(2,4,5-trichlorobenzylidene)hydrazine-1-carboximidamide.

26. A selective PPP1R15B inhibitor for use in the treatment of Parkinson's disease, wherein the inhibitor is a compound selected from:
(E)-2-(2,3-dichlorobenzylidene)hydrazine-1-carboximidamide;
(E)-2-(2-chloro-4-fluorobenzylidene)hydrazine-1-carboximidamide;
(E)-2-(3,4,5-trichlorobenzylidene)hydrazine-1-carboximidamide; and
(E)-2-(2,4,5-trichlorobenzylidene)hydrazine-1-carboximidamide.

27. Use of a compound selected from:
(E)-2-(2,3-dichlorobenzylidene)hydrazine-1-carboximidamide;
(E)-2-(2-chloro-4-fluorobenzylidene)hydrazine-1-carboximidamide;
(E)-2-(3,4,5-trichlorobenzylidene)hydrazine-1-carboximidamide; and
(E)-2-(2,4,5-trichlorobenzylidene)hydrazine-1-carboximidamide,
as a PPP1R15B selective inhibitor.

EXAMPLES

Example A

Preparation of the Compounds According to the Present Invention

The compounds according to the present invention can be prepared according to the following procedures:
General Procedure A:

To a solution of benzaldehyde (1eq.) in ethanol (300 ml) was sequentially added a minoguanidine hydrochloride (1eq.) and sodium acetate (1eq.) at 25° C. The resulting reaction mixture was heated at 80° C. for next ~6 hours. Reaction completion was monitored on TLC using dichloromethane/methanol (8/2) as mobile phase. After completion of reaction, the reaction mixture was allowed to cool down to 25° C. and dumped in the saturated solution of $NaHCO_3$ (700 ml). The resulting precipitate were filtered off under vacuum and washed with water (100 ml). The resulting solid material was triturated with diethylether (2×25 ml) and dried under vacuum to provide the desired substituted aminoguanidine derivative.

The following compounds were prepared according to general procedure A:

Example 1

(E)-2-(2,3-dichlorobenzylidene)hydrazine-1-carboximidamide

Prepared following general procedure A from 2,3-dichlorobenzaldehyde in 85% yield (considering mono acetate salt) LC-MS: m/z=231.23 (M+H). $^1$H-NMR (DMSO-$d_6$): δ (ppm) 11.85 (brs, 1H); 8.35 (s, 1H); 8.19-8.21 (dd, 1H); 7.56-7.59 (dd, 1H); 7.32-7.36 (t, 1H); 7.04 (brs, 4H); 1.84 (s, 3H); MS (ESI+): m/z=231.23[M+H]$^+$ Example 2

(E)-2-(2-chloro-4-fluorobenzylidene)hydrazine-1-carboximidamide

Prepared following general procedure A from 2-chloro-4-fluorobenzaldehyde in 67% yield. $^1$H-NMR (DMSO-$d_6$): δ (ppm) 5.80 (brs, 2H); 5.84 (brs, 2H); 7.19-7.34 (m, 4H); 8.16 (s, 1H); MS (ESI+): m/z=215.1 [M+H]$^+$ Example 3

(E)-2-(3,4,5-trichlorobenzylidene)hydrazine-1-carboximidamide

Prepared following general procedure A from 3,4,5-trichlorobenzaldehyde in 70.88% yield. $^1$H-NMR (DMSO- $d_6$): δ (ppm) 7.96 (s, 2H); 7.89 (s, 1H); 6.20 (brs, 2H); 5.69 (brs, 2H); MS (ESI+): m/z=265.1 [M+H]$^+$ Example 4

(E)-2-(2,4,5-trichlorobenzylidene)hydrazine-1-carboximidamide

Prepared following general procedure A from 2,4,5-trichlorobenzaldehyde with 78.76% yield. $^1$H-NMR (DMSO-$d_6$): δ (ppm) 8.43 (s, 1H); 8.12 (s, 1H); 7.77 (s, 1H); 6.33 (brs, 2H); 5.83 (brs, 2H); MS (ESI+): m/z=265.17 [M+H]$^+$ Protein Expression, Purification and Analysis by Surface Plasmon Resonance
Protein Expression and Purification PPP1R15A$^{325-636}$ and PPP1R15B$^{340-698}$ were expressed and purified as follows: the cDNAs encoding amino acids 325-636 of PPP1R15A and 340-698 of PPP1R15B were His-tagged and cloned into pMAL-c5x. The amino acid sequences of R15A and R15B are set out in FIG. 16. Recombinant PPP1R15A/B were expressed in BL21-Gold cells and purified by affinity chromatography on a HisTrap HP column (GE Healthcare), followed by a MBPTrap HP column (GE Healthcare). cDNA encoding for human PP1γ (PP1c) was cloned into the baculovirus transfer vector pDW464 to add a biotin acceptor peptide (BAP). The vector also encodes for the *E. coli* biotin holoenzyme synthetase (BirA), so that BAP-tagged proteins can be biotinylated in vivo in *Spodoptere frugiperda* (Sf9) insect cells (Duffy et al., Anal. Biochem., 262, 122-128, 1998). The Bac-to-Bac baculovirus expression system (Life Technologies) was used to generate the recombinant bacmid DNA and Sf9 insect cells were used to amplify the viral stocks. Cultures were harvested by centrifuging at 1,200 g for 15 minutes, cell pellets were resuspended in lysis buffer (50 mM Tris pH 7.4, 150 mM NaCl, 0.2% Triton, 5% Glycerol, 1 PiC tablet (Roche) per 50 ml and 0.2 mM PMSF) and followed by gentle sonication. The protein was first purified on a 5 ml HiTrap Q HP column (GE Healthcare) followed by a HiLoad 16/600 Superdex 200 column (GE Healthcare). The positive fractions confirmed by SDS-PAGE and western blot were pooled, concentrate to ~1 µM and stored at −80° C.

Capture of Biotin-PP1 on the SA Sensor Chip

A Biacore T200 (GE Healthcare) system was used for all experiments and biotinylated PP1 was captured using a Sensor Chip SA (GE Healthcare, catalog no BR-1005-31). The streptavidin coated surface was activated by 1 min injection with a solution of 50 mM NaOH and 1 M NaCl. Biotin-PP1 was diluted in the running buffer (50 mM Tris pH 7.5, 100 mM NaCl, 0.1 mM EGTA, 1 mM MnCl2, 0.05% Tween 20) and injected at approximately 300 nM concentration directly to streptavidin coated surface for 100 sec or to reach immobilization level of biotin-PP1 corresponding to ~7000 RU. A blank immobilization was performed for one of the SA sensor chip surface to use as a reference.

Determining Steady-State Binding Constants of Small Molecules to eIF2α Holophosphatase Complexes Using the Biotin-PP1 Surface With minor deviations, the same procedure and conditions were used in all binding experiments. Small molecules were stored as 50 mM stock solutions in 100% DMSO. Prior to determining binding constants, serial dilutions of either 12 or 8 concentrations of the compounds were prepared in the running buffer in a 96-well plate. Prior to each compound dilution series the regulatory subunit, R15A or R15B, was diluted to 15 µM in the running buffer and captured on the biotin-PP1 surface, to form the holophosphatase complex on the sensor chip surface. Then, without regenerating the surface, the compound dilution series was injected onto the surface of the chip Sensorgrams were analyzed using the Biacore T200 evaluation software and the binding constants determined based on a steady-state model. Kinetic experiments are carried out using different concentrations of the compound and their respective equilibrium binding levels determined. These equilibrium response levels (Req) are plotted against concentration and fitted using a global fit, which is able to determine steady-state affinity constants, i.e. the concentration at 50% saturation is KD (Frostell-Karlsson et al., J. Med. Chem., 43, 1986-1992, 2000).

Mammalian Cell Culture

HeLa cells were cultured in Dulbecco's Modified Eagle's Media (DMEM) supplemented with penicillin, streptomycin, containing 5% and 10% fetal bovine serum (FBS), respectively. MEF cells were cultured in DMEM supplemented with penicillin, streptomycin, glutamine, 55 µM β-mercaptoethanol, 1X non-essential amino acids (Sigma-Adrich) and 10% FBS. Where indicated, cells were treated with 2.5 µg/ml tunicamycin, 1 mM DTT (Sigma-Adrich) and or the indicated compounds at the indicated concentrations.

Protein Analyses by Immunoblots

For immunoblots, HeLa cells (80,000 cells/ml) were plated in 12-well plates 24 hours before each experiment. Immediately after the indicated treatments, cells were lysed in 75 µl Laemmli Buffer, boiled at 95° C. for 5 minutes and sonicated. Proteins were separated and analysed as described (Tsaytler et al., Science, 332, 91-94, 2011) with the following antibodies: phospho-elf2α [pS52] and PPP1R15A/GADD34 (10449-1-AP; ProteinTech Group, 1/1000 dilution).

Assessment of Cell Viability

Cells were plated in 24-well plates at a density of 15,000 (HeLa) or 12,000 cells/ml (MEFs) 24 hours prior to treatment. ER stress was elicited by addition of fresh media containing 2.5 µg/ml tunicamycin (Sigma-Aldrich). Compounds of Example 1 were dissolved in DMSO and added as indicated. DMSO was used as a mock treatment. Cell viability was assessed by measuring the reduction of WST-8 [2-(2-methoxy-4-nitrophenyl)-3-(4-nitrophenyl)-5-(2,4-disulfophenyl)-2H-tetrazolium] into formazan using Cell viability Counting Kit-8 (Dojindo) according to the supplier's recommendation, 48 hours after tunicamycin treatment.

Animal Studies

All animal care and procedures were performed in compliance with the regulation on the use of Animals in Research (UK Animals Scientific Procedures Act of 1986) with local ethical approval.

For studying the effect of a compound of Example 1 on weight, C3H/B6 mice were gavaged orally once a day with compounds of Example 1 and mice weight was recorded daily for 2 weeks.

To assess the efficacy of a compound of Example 1 in ameliorating a disease phenotype, 28-day old transgenic mice or littermate control were orally administered daily with a compound of Example 1 (2 mg/kg) or vehicle for a duration of 4 weeks. Disease progression was evaluated by weighting the mice during the treatment and by assessing their motor performances after 4 weeks of treatment.

To assess whether of a compound of Example 1 had the side effects of Guanabenz, mice (n>3) were gavaged orally with 10 mg/kg of compound or Guanabenz. Their activity was monitored 30 minutes following dosing. Guanabenz treated mice did not move 30 minutes after dosing, due to the hypotensive activity of Guanabenz, in contrast to mice treated with compound of Example 1 which were as active as untreated mice.

Eight weeks old HD-N171-82Q mice and their wild-type littermates were first habituated for 1 min on a static rotor and 1 min at constant speed (4 rpm). Habituation was repeated. The test session consisted of four trials with 15 min intervals in between. For each trial 5 mice were placed on an accelerating rotor (4 to 40 rpm) and the latency to fall was recorded, with a maximum limit for individual animal set at 300 s.

For treatment of a metabolic disorder, Db/db animals (n=5 per condition) were treated once a day with 1 mg/kg of compound of Example 1 for three weeks. Blood glucose levels were measured with a blood glucose meter (DSI) between 9 and 10 am. Data are mean +/− S.e.m.

Quantitative RT-PCR

RNA from brain was extracted in trizol (Life Technologies). RNA concentration was measured using a NANO-DROP1000 spectrophotometer (Thermo Fisher Scientific), and 1 µg was reverse transcribed to cDNA using a SuperScript reverse transcriptase (Life Technologies). Quantitative PCR with primers GAPDH (f): ACCACAGTCCATGC-CATCAC, GAPDH (r): TCCACCACCCTGTTGCTGTA, PPP1R15A (f): CCTCCTGAAACTTGGGGACT;

and PPP1R15A (r): GCTGTGATGTGGGATAAGCG was performed using SYBR® Select Master Mix (Ref 4472908, applied biosystems) on a Corbett Rotor-Gene version 6000. Expression of each gene was normalized to the housekeeping gene GAPDH and expressed as fold change calculated using Paffl equation.

DRG Cultures

Dorsal root ganglia (DRG) dissected from wild-type or Pmp22Tr-J (PMP22mutant) (Henry et al., Neuropathol. Exp. Neurol., 42, 688-706, 1983) embryo at 13.5 or development (E13.5) were cultured on collagen coated coverslips in neurobasal media supplemented with 4 g/l glucose, 2 mM L-glutamine, 2% B27 supplement and 50 ng/ml neuronal growth factor (NGF) for 7 days. To differentiate Schwann cells and induce myelination, the cultured DRGs were then maintained in C-media (MEM media supplemented with 4 g/l glucose, 2 mM L-glutamine, 10% FCS, 50 ng/ml NGF). The C-media was replaced every other day with freshly added 50 µg/ml ascorbic acid ±5 nM of compound of Example I and cultured for 14 days for myelination by the Schwann cells. The cultured DRGs were then fixed in 4% paraformaldehyde and immunostained with MBP (Rat Myelin basic protein, 1/250 dilution, ab73498).

The reference for the mice is Pubmed ID: 631386.

Biochemical Assay

Assay 1: A Selective PPP1R15B Inhibitor Selectively Binds to PPP1R15B-PP1 (FIG. 1)

Surface Plasmon Resonance (SPR) was used to measure the binding affinity of compounds to the PPP1R15A/B-PP1 phosphatase complex. Biotin acceptor peptide (BAP) was fused to the N-terminus of PP1γ, which enables the biotinylation of the BAP-tagged protein in Sf9 insect cells. After purification the BAP-PP1γ protein was captured on a streptavidin sensor chip (SA-chip, GE healthcare) to a response level of ~5.000 RU. Using controlled biotinylation enables orientated and uniform immobilization on the sensor chip surface. The PP1γ was then used to capture PPP1R15A/B and form a holophosphatase complex on the surface of the streptavidin chip. This complex can then be used to test binding of compounds. 10 µM PPP1R15A/B protein concentration was used to form the holophosphatase complex during a 80 s injection. After PPP1R15A/B has been captured a concentration series of a compound is injected over the surface of the chip, measuring the binding of the compound to the holophosphatase. After the concentration series (8 or 12 concentrations) is completed the surface is regenerated with 3 M NaCl and we can capture R15A/B again to form a fresh holophosphatase complex to measure a binding of another compound concentration series. Analysing the level of equilibrium binding as a function of concentration gives interaction affinities or steady-state binding affinity ($K_D$).

FIG. 1 shows the $K_D$ values for the compound of Example 1. A $K_D$ of 0.035 µM for PPP1R15B-PP1 and 1 µM for PPP1R15A-PP1 demonstrates that the compound of Example 1 selectively binds to the PP1R15B-PP1 complex but that binding is significantly less to the PPP1R15A-PP1 complex.

Assay 2: A Selective PPP1R15B Inhibitor Induces a Transient Phosphorylation of eIF2α in Cells, in the Absence of Stress (FIGS. 2A and B)

The selectivity of a compound of Example 1 was revealed using an in vitro binding assay with recombinant proteins. However, whilst a binding assay can be used to screen for selective compounds binding to PPP1R15B, the properties of a compound are not necessarily predicted by a binding assay. Thus, other assays are needed to assess whether the compound inhibits PPP1R15B function or not.

Human cells were treated with a PPP1R15B inhibitor and eIF2α phosphorylation was monitored over time. The inventors found that, in the absence of stress (under conditions where cells do not express PPP1R15A) treatment of cells with a compound of Example 1 induced eIF2α phosphorylation. This was manifested between 1 and 7.5 hours after addition of the compound of Example 1. However, at 10 hours following the addition of the compound of Example 1, eIF2α phosphorylation returned to basal levels. This suggested that there was an active eIF2α phosphatase at this time point. Indeed, the inventors noticed that PPP1R15A was induced at the late time points following addition of the compound of Example 1 (see Assay 3). The transient induction of eIF2α phosphorylation demonstrates that the compound is a selective inhibitor of PPP1R15B in cells. Furthermore, this establishes that the compound of Example 1 spares PPP1R15A. This assay can serve to identify other selective PPP1R15B inhibitors.

Assay 3: A Selective PPP1R15B Inhibitor Induces Expression of PPP1R15A in Cells (FIGS. 2A and B)

Cells and organisms usually have mechanisms to compensate for deficiencies. The inventors therefore considered whether cells might compensate for PPP1R15B inhibition by inducing PPP1R15A. It has been previously reported that PPP1R15A levels are increased in the liver of PPP1R15B knock-out mice (Harding et al., Proc. Natl. Acad. Sci. U.S.A., 106, 1832-1837, 2009). It is unknown whether this compensatory response is specific to the liver or if it can happen in cells or other tissues. Furthermore, prior to this study, it was unknown whether PPP1R15A induction can be observed upon pharmacological inhibition of PPP1R15B, as they were no selective inhibitors of PPP1R15B prior to this study.

FIG. 2B demonstrates that cells treated with a compound of Example 1 were found to induce PPP1R15A. This property, induction of PPP1R15A, can be used as a method to screen for PPP1R15B inhibitors as compounds which induce PPP1R15A expression in cells will possess PPP1R15B inhibition properties. For example, an assay using a PPP1R15A gene or promoter fused to a reporter gene can be designed and developed in to a HTS screen to identify compounds that induce PPP1R15A.

Assay 4: A Selective PPP1R15B Inhibitor Protects Cells from Stress (FIG. 3)

FIG. 3 demonstrates that a selective PPP1R15B inhibitor protects cells from stress. Cells where stressed with Tunicamycin (2.5 ug/ml) in the presence of 0.2-5 µM of a compound of Example 1. Cell viability was measured 3 days after treatment.

The inhibitor of Example 1 protects cells from cytotoxic stress caused by tunicamycin. Cytoprotection against ER stress can be measured by a suitable assay. In this instance, cytoprotection was measured in HeLa cells in which ER stress was elicited by the addition of media containing tunicamycin, a drug that blocks N-glycosylation, thereby preventing protein folding and inducing the unfolded protein response. Cell viability was then detected in the presence and absence of a compound of Example 1 after a set period of time, by measuring the reduction of WST-8 into formazan using the standard cell viability kit Cell Viability Counting Kit-8 from Dojindo. Cytoprotection from ER stress was measured in terms of the percentage increase in viable cells (relative to control) after ER stress.

Assay 5: A Selective PPP1R15B Inhibitor Prolongs eIF2α Phosphorylation During Stress-Recovery (FIG. 4)

The inventors reasoned that a PPP1R15B inhibitor should prolong eIF2α phosphorylation following stress. To reveal this activity, it was crucial to search for conditions where PPP1R15A is not expressed, to avoid confounding effects. The inventors took advantage of the fast kinetic and reversibility of stress induction by DTT (Bertolotti et al., Nat. Cell. Biol., 2, 326-332, 2000; Jousse et al., 2003) and monitored eIF2α phosphorylation in cells following a 30 minute treatment with 1 mM DTT and a wash out. The inventors found that the decline in eIF2α phosphorylation that normally occurs after the DTT-washout is delayed and this occurred before any substantial induction of PPP1R15A. Thus, careful monitoring of the kinetic of eIF2α dephosphorylation in the early phase of a stress-recovery paradigm such as the one described here can be used to identify other PPP1R15B inhibitors.

Compound of Example 1 in Mice (FIG. 5) has a Good Tissue Distribution

Analysis of mouse tissues (plasma, brain, spinal cord, pancreas, liver) at different time following oral gavage of a compound of Example 1 revealed that the PPP1R15B inhibitor has an extensive tissue distribution and therefore demonstrates application in the treatment of various diseases and disorders affecting different organs.

Figure 6:
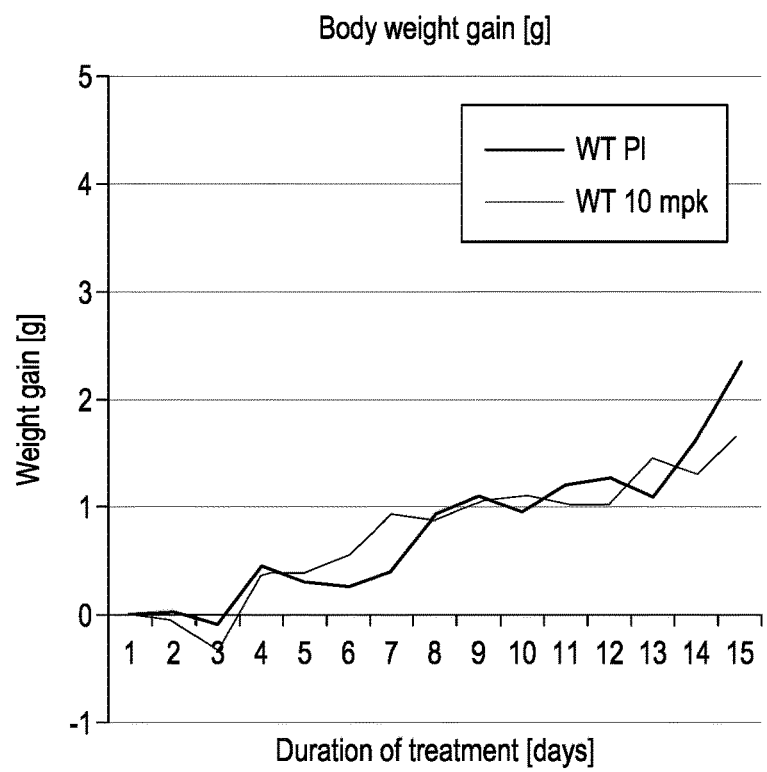
FIG. 6 shows that the treatment of mice with a compound of Example 1 (10 mg/kg) is not toxic.

Treatment of Mice with a Compound of Example 1 is Not Toxic to Mice (FIG. 6)

Mice were treated with Example 1 and monitored closely to detect any clinical signs. It was found that mice treated for 2 weeks with up to 10 mg/mg once a day of a compound of Example 1 were undistinguishable from mice treated with placebo and the mice gained weight normally (FIG. 6). This establishes that PPP1R15B inhibition is not toxic. This was surprising and unanticipated as prior to this study one would have speculated that PPP1R15B inhibitors would be so deleterious that they would have no therapeutic potential.

Figure 7:
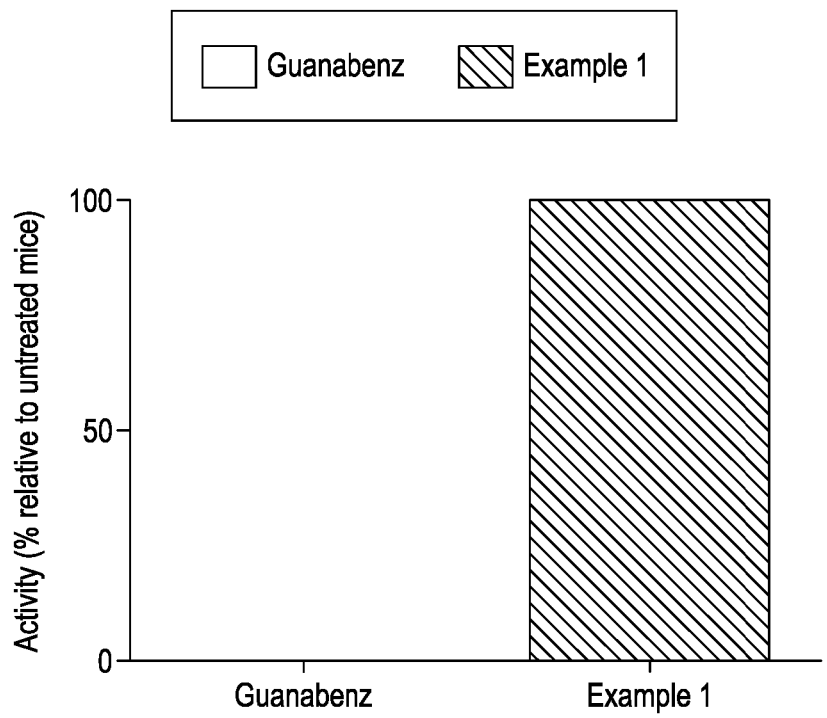
FIG. 7 shows that the treatment of mice with a compound of Example 1 (10 mg/kg) does not cause the side effects of Guanabenz.

Treatment of Mice with a Compound of Example 1 Does Not Cause the Side Effects Caused by Guanabenz (FIG. 7)

In humans, the adrenergic agonist activity of Guanabenz has side effects including drowsiness and coma at high doses (A. H. Hall, Ann Intern Med 102; 787-788; 1985). Due to of these side effects, Guanabenz is no longer used in human. It is anticipated that Guanabenz derivatives have the side effects of Guanabenz, associated with alpha-2 adrenergic activity. While the structure-activity relationship of Guanabenz to alpha-2 adrenergic receptor is not available, the inventors found here that Example 1 is devoid of the side effects of Guanabenz, while structurally very similar.

Figure 8:
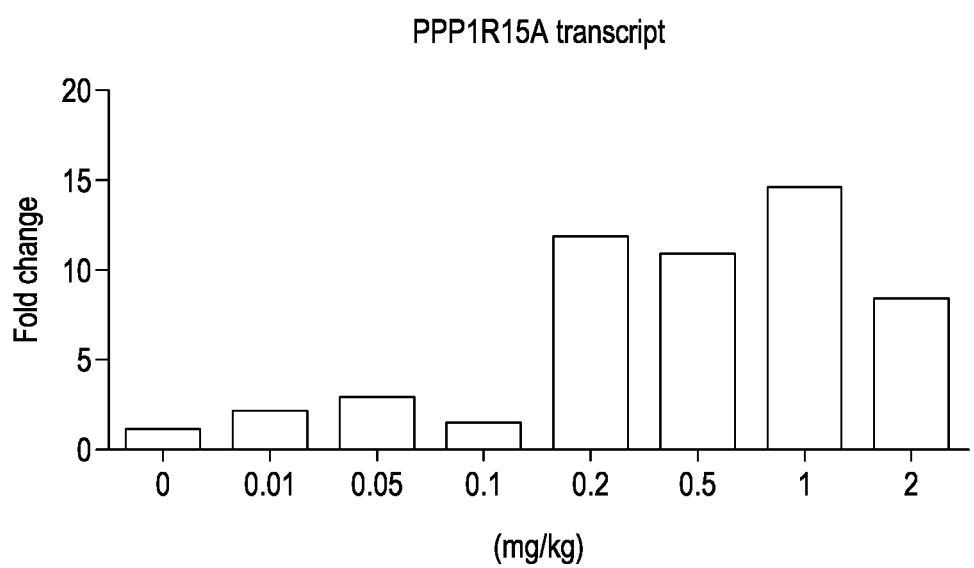
FIG. 8 shows the induction of R15A in a mammal following treatment with a compound of Example 1.

Assay 6: Induction of PPP1R15A in a Mammal Following Treatment with a Compound of Example 1 (FIG. 8)

PPP1R15A induction was assessed by qPCR on total mRNA extracted from brains of mice treated with the indicated doses of compound of Example 1.

Similar to what had been seen in cells, it was found that mice induced PPP1R15A following a treatment with a compound of Example 1 and that this induction was dose-dependent. This explains why a selective PPP1R15B inhibitor is tolerated in mice: PPP1R15A induction dephosphorylates eIF2α, ensuring that the eIF2α phosphorylation which results from PPP1R15B inhibition by a compound of Example 1 is only transient. This is important because a persistent phosphorylation of eIF2α is detrimental. The induction of PPP1R15A in vivo by a PPP1R15B inhibitor is a pharmacodynamic parameter that can be used to evaluate the efficacy and potency of PPP1R15B inhibitors in mammals in pre-clinical or clinical studies.

Figure 9:
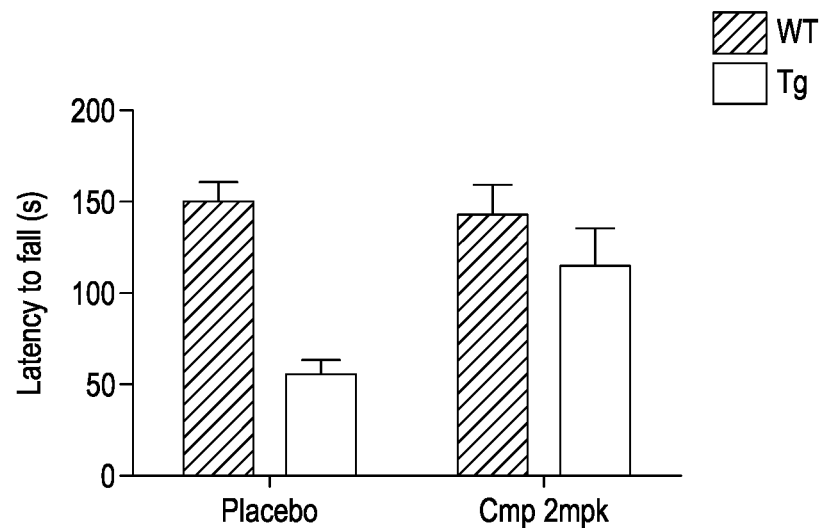
FIG. 9 shows the effectiveness of a R15B inhibitor of Example 1 in preventing disease in a mammal. The example used in FIG. 9 is Huntington's disease using the mouse model HD82GIn (Schilling et al., Hum. Mol. Genet., 8, 387-407, 1999). WT: wild-type mice. Tg: HD82GIn.

A Compound of Example 1 Prevents a Disease in a Mammal (FIG. 9)

Increasing folding by inhibition of PPP1R15B has the potential to benefit a very broad range of human pathologies. To test this, the inventors looked at Huntington's disease (HD), a proteostasis disease caused by accumulation of a misfolded protein, mutant Huntingtin. There are some reports indicating that mutant Huntingtin induces the UPR (Duennwald and Lindquist, Gene & Development, 22, 3308-3319, 2008; Nishitoh et al., Genes & Development, 16, 1345-1355, 2002). However, the inventors' failure to detect PPP1R15A in models of Huntington's disease suggested that PPP1R15A is not a therapeutic target for HD. As HD has no cure to date, the inventors tested whether HD could be prevented by PPP1R15B inhibition. The inventors found that treatment of HD mice with 2 mg/kg of a compound of Example 1 prevented the motor performances impairment (FIG. 9). This demonstrates that PPP1R15B is a valid therapeutic target and that therefore PPP1R15B inhibition will be useful in the treatment and prevention of diseases.

As demonstrated here, to determine whether a disease can be prevented or ameliorated by PPP1R15B inhibition, mouse models or humans can be treated with tolerable doses of inhibitor. To attest target inhibition in vivo, markers of the PPP1R15B pathway can be monitored and used as pharmacodynamics markers. Such markers can be PPP1R15A, as shown here (FIG. 8) or any other on-pathway targets such as UPR or ISR markers (including but not restricted to eIF2α phosphorylation, CHOP, ATF4). As shown here with a compound of Example 1, a PPP1R15B inhibitor will be useful for therapies as long as it is safe and this is determined by the selectivity of the compound for PPP1R15B.

Figure 10:
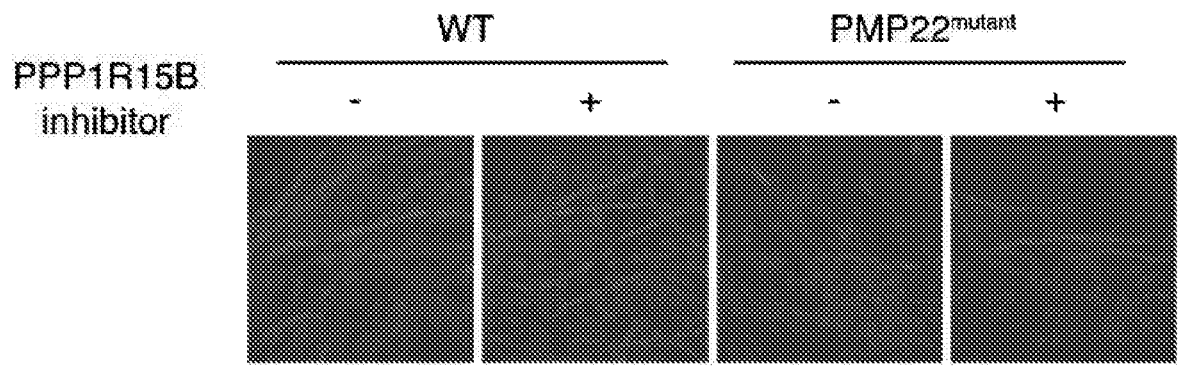
FIG. 10 shows myelin internodes in red (rod shaped) from cultured dorsal root ganglia (DRG) and nuclei in blue (spherical 'blob' shaped) in of the indicated genotype treated with vehicle or compound of Example 1. The myelin internodes in the PMP22-mutant mice are shorter. Treatment with a compound of Example 1 increased the length of myelin internodes in mutant DRG revealing that it improved myelination.

Myelination in Explants from Neuropathic Mice (FIG. 10).

CMT is a group of myelin neuropathies caused by mutations in a number of genes. Mutations in the peripheral myelin protein PMP22 are the most common causes of CMT. A mutation in PMP22 (Trembler-J) causes the misfolding of PMP22 and a disease in mice that resembles CMT in human due to defects in myelin in the peripheral nervous system. Explants from PMP22 mutant mice recapitulates the severe hypomyelination observed in the human diseases. The inventors found that treatment of dorsal root ganglia culture (DRG) from PMP22 mutant mice improved myelination. It has been previously found that the DRG cultures from mutant mice are useful models to predict therapeutic efficacy of compounds. Thus, the data present here demonstrate that the compound of Example 1 will be useful to treat a disease caused by mutation or overproduction of PMP22, such as CMT disease. The compound of Example 1 will also be useful in the treatment of other myelin disorders.

Assessment of PPP1R15B Efficacy in a Metabolic Disease (FIG. 11)

It is known that metabolic diseases such as diabetes, obesity, fatty liver disease, and atherosclerosis are associated with pathological ER stress and it is believed that pharmacological modulators of the UPR may have therapeutic benefit. As there were no PPP1R15B inhibitors available prior to this study it was unclear whether PPP1R15B could be a therapeutic target in metabolic diseases. The inventors tested this possibility and found that treatment of obese mice with a compound of Example 1 reduced the pathological high blood glucose in these mammals (FIG. 11). This demonstrates that treatment with a compound of Example 1 can ameliorate a metabolic disorder.

Having shown in one disease model that treatment with a compound of Example 1 is beneficial, it is evident that the compounds of the invention will be beneficial to other mammalian metabolic disorders such as diabetes, obesity, fatty liver disease, and atherosclerosis.

Example B

Reversible phosphorylation controls the activity of most proteins. With only a few serendipitously-discovered inhibitors of serine/threonine phosphatases, this large family of enzymes is still thought to be undruggable. Here we use surface plasmon resonance to design a method that enabled the rational discovery of TST3 (compound set out in Example 1) a selective inhibitor of PPP1R15B, a regulatory subunit of protein phosphatase 1. Selective inhibition of PPP1R15B caused a rapid and transient accumulation of its phosphorylated substrate, the α subunit of translation initiation factor 2 (eIF2α). This resulted in a rapid and transient attenuation of protein synthesis, a property that we exploited therapeutically to safely prevent the behavioral and molecular defects in a mouse model of Huntington's disease, a paradigmatic protein misfolding disease. This establishes that the intrinsically disordered regulatory subunits of serine/threonine phosphatases are valid and tractable drug targets and provides a generalizable method to identify their selective inhibitors.

To survive, cells respond to harsh conditions by phosphorylating the α subunit of eukaryotic translation initiation factor 2 eIF2 α on Serine 51 to reduce protein synthesis, thereby sparing resources to neutralize challenges (1-3). Dynamic fine-tuning of eIF2α phosphorylation is vital and both a lack and an excess of eIF2α phosphorylation is deleterious (4). To safe-guard against a persistent phosphorylation of eIF2α, mammals have evolved two selective eIF2α phosphatases composed of one or two regulatory subunits, the inducible PPP1R15A (R15A) or the constitutive PPP1R15B (R15B), bound to the catalytic subunit PP1c (5, 6). R15A inhibitors have been serendipitously identified and provided the proof of concept that serine-threonine phosphatases can be selectively inhibited by targeting regulatory subunits (7, 8). Whilst the same paradigm could in principle be exploited to selectively inhibit any other PP1 holophosphatases, the rational discovery of selective inhibitors of intrinsically disordered regulatory subunits of phosphatases represents an unmet challenge.

Figure 12:
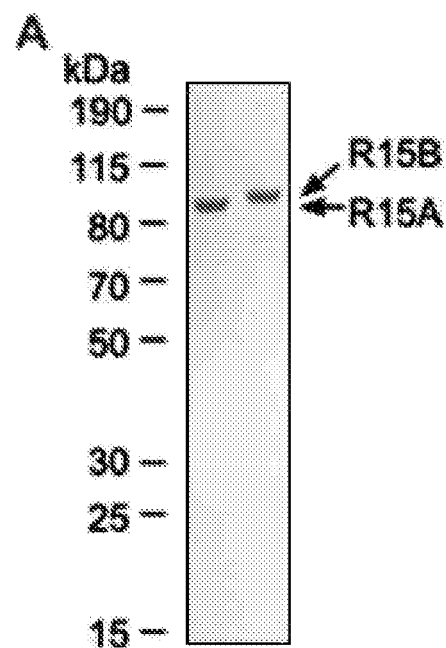
FIG. 12 shows an InstantBlue (Comassie blue)—stained gel showing recombinant proteins MBP-R15A$^{325-636}$-His, MBP-R15B$^{340-698}$-His.
Figure 14:
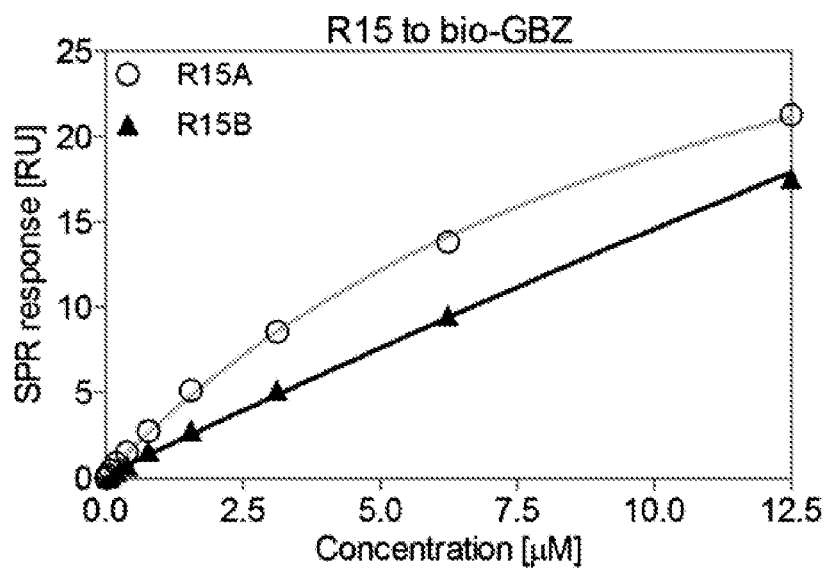
FIG. 14 shows the Response units from FIG. 13 B were plotted against protein concentrations to determine the steady-state binding constant ($K_D$). Binding of R15A (○, blue) and of R15B (▲, magenta). $K_D$ of R15A for bio-GBZ is 11 μM and $K_D$ of R15B for bio-GBZ is 123 μM.

Here we set out to develop a generalizable strategy to identify new selective phosphatase inhibitors. First, we expressed and purified R15A and R15 B (FIG. 12) and used surface plasmon resonance (SPR) to measure binding affinities of known R15A inhibitors to their targets. We tried to immobilized R15 on SPR chip but this method produced inconsistent results, probably because the natively unstructured proteins precipitate on the chip. We therefore used biotynilated guanabenz (GBZ) (7) that we immobilized on the chip and tested binding of the proteins on the immobilized compound (FIGS. 13A and 13B). We found that the known R15A inhibitor GBZ bound to recombinant R15A fragment with a ten times higher affinity than R15B (FIGS. 13 and 14) confirming its selectivity for R15A (7). However, the 11 μM affinity of GBZ for R15A was incompatible with the submicromolar potency of GBZ in cells (7), indicating that the assay used here didn't recapitulate the cellular conditions probably because the isolated regulatory subunit is intrinsically disordered (9).

We therefore designed another assay to circumvent the problem encountered with working with isolated regulatory subunits.

Figure 15:
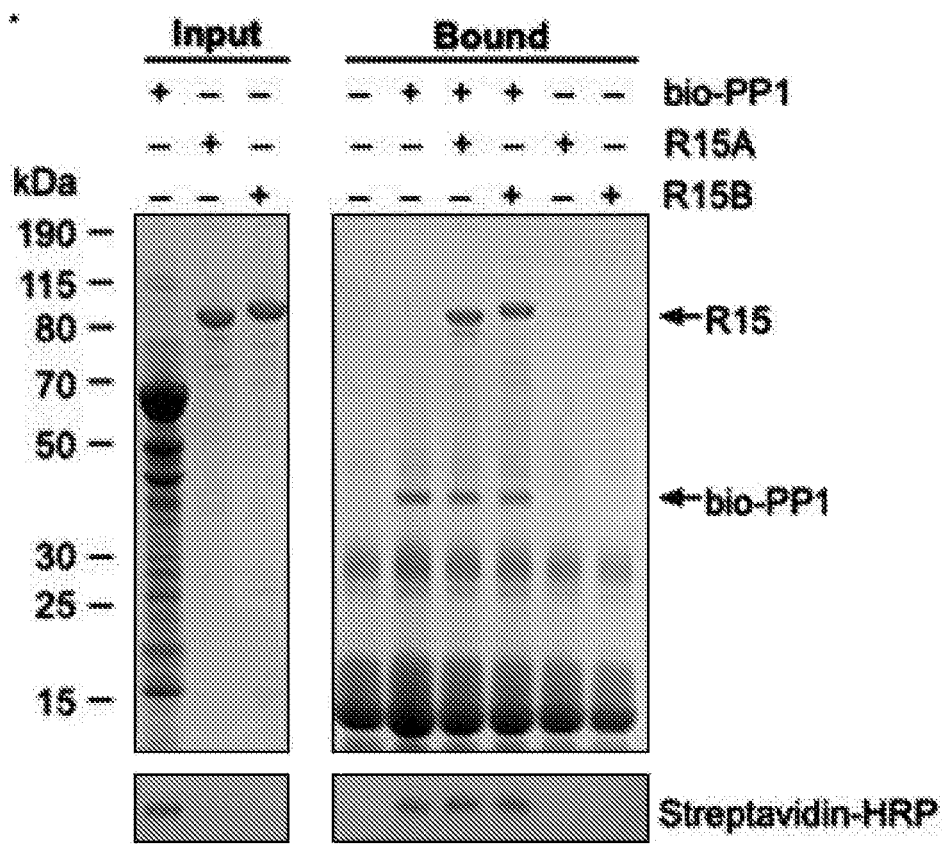
FIG. 15 Upper panel: InstantBlue-stained gel showing recombinant bio-PP1 (partially purified), MBP-R15A$^{325-636}$-His and MBP-R15B$^{340-698}$-His (input). BAP-PP1c, purified on neutravidin beads, bound R15A and R15B (bound). Bio-PP1c=biotinylated PP1. Lower panel: Immunoblot showing biotinylated PP1c.
Figure 17:
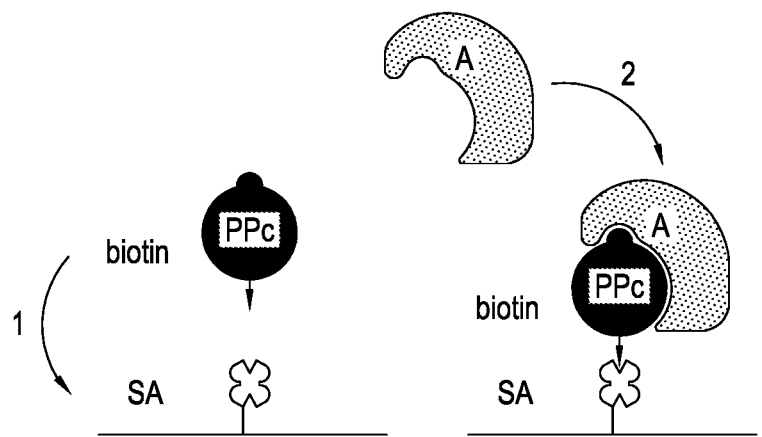
FIG. 17 shows a cartoon depicting the reconstitution of R15 holophosphatases on a streptavidin (SA)—SPR chip.
Figure 18:
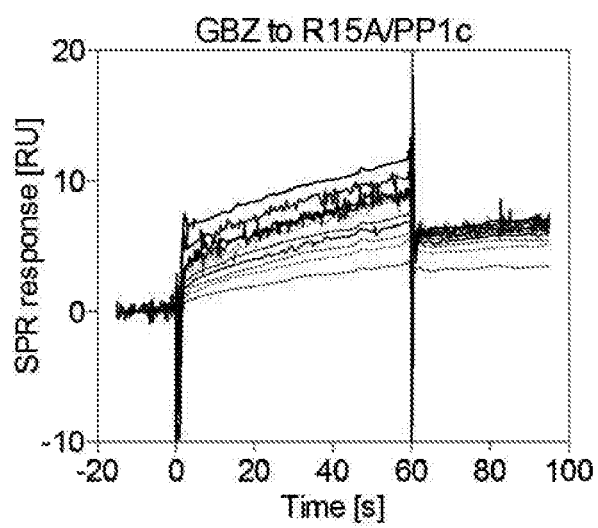
FIG. 18 shows SPR sensograms of guanabenz binding to the R15A-PP1c holophosphatase immobilized on a SPR sensorchip.
Figure 19:
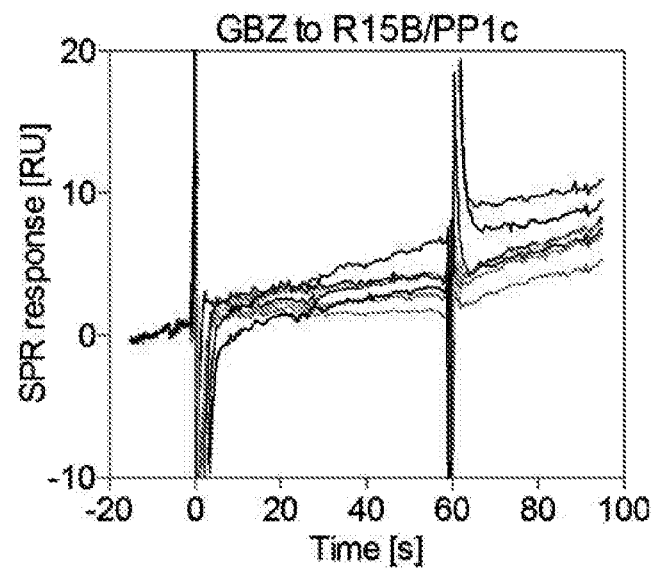
FIG. 19 shows SPR sensograms of guanabenz binding to the R15B-PP1c holophosphatase immobilized on a SPR sensorchip.
Figure 20:
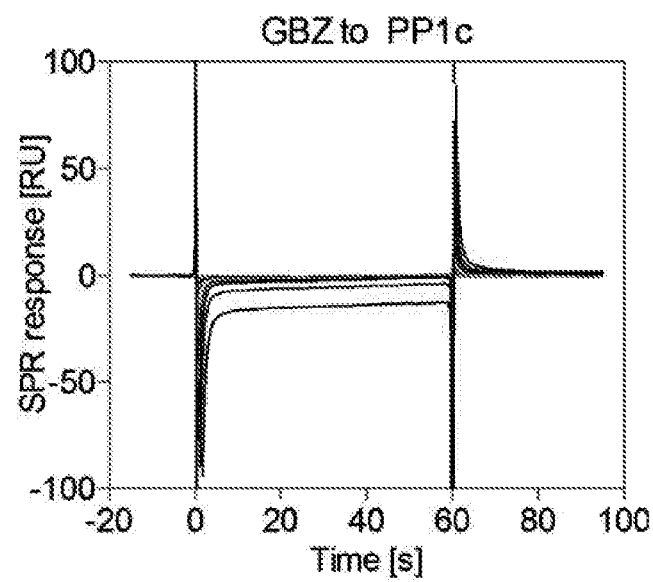
FIG. 20 shows SPR sensograms of guanabenz binding to the PP1c holophosphatase immobilized on a SPR sensorchip.

In cells, regulatory subunits of phosphatases fold upon binding to PP1c (9) suggesting holophosphatases may be required to design relevant assays. We reconstituted a recombinant R15A-PP1c using an in vivo biotynilated PP1c and a large R15A fragment (amino acid 325-636), known to bind GBZ (7) and Sephin1 (8). The R15A-PP1c complex was purified by affinity capture on neutravidin resin (FIG. 15). Likewise, the paralogous holophosphatase R15B-PP1c was purified (FIG. 15). Note that R15A and R15B are functionally related but with very different sequences (FIG. 16). The R15-PP1c holophosphatases were next immobilized on a SPR streptavidin sensor chip in two steps (FIG. 17). SPR experiments showed that GBZ and Sephin1 strongly bound to R15A-PP1c but not or weakly to the R15B-PP1c (FIGS. 18-22) and not to PP1c alone (FIG. 18-22), confirming their selectivity for R15A. The measured steady-state affinities of GBZ and Sephin1 for R15A-PP1c, 0.122 μM and 0.786 μM respectively were compatible with the submicromolar potency of the inhibitors in cell-based assays (7) and in vivo (8). Thus, SPR experiments conducted with recombinant holophosphatases provide a quantitative method to measure relevant binding affinities of known inhibitors to R15A.

Figure 24:
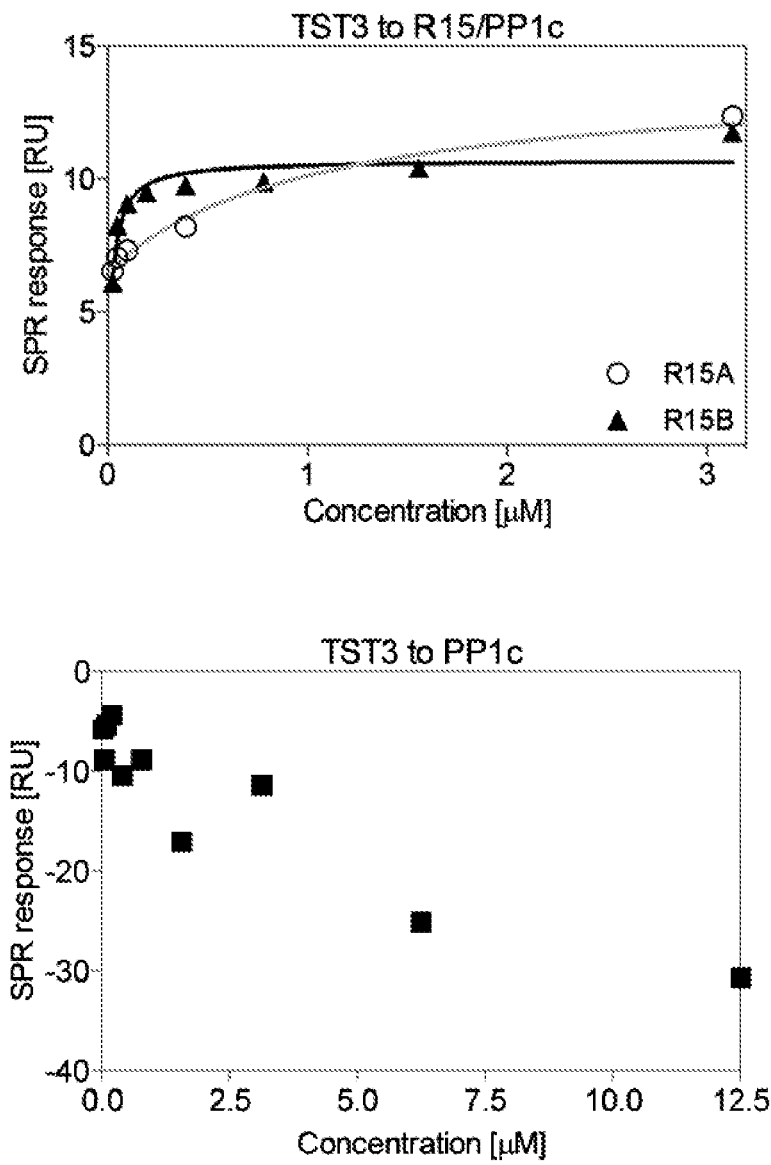
FIG. 24 shows the steady states affinities of TST3 to R15A-PP1c, R15B-PP1c and PP1c immobilized on SPR chips of the present invention.

We next used the method established here to search for selective phosphatase inhibitors with novel properties. We synthetized GBZ derivatives and identified TST3 (rational inhibitor of a holophosphatase), a compound which bound strongly and selectively to R15B ($K_D$=0.033 μM) (FIG. 24).

Figure 23:
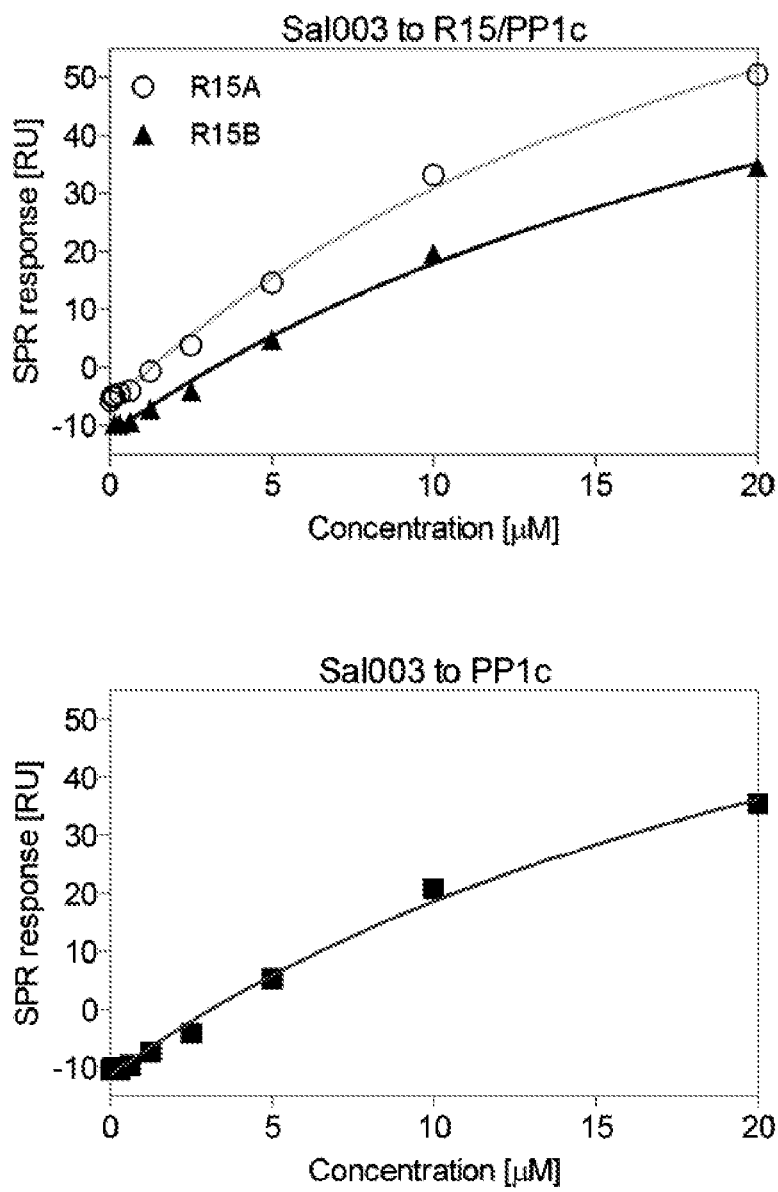
FIG. 23 shows the steady states affinities of Salubrinal to R15A-PP1c, R15B-PP1c and PP1c immobilized on SPR chips of the present invention.
Figures 25, 26:
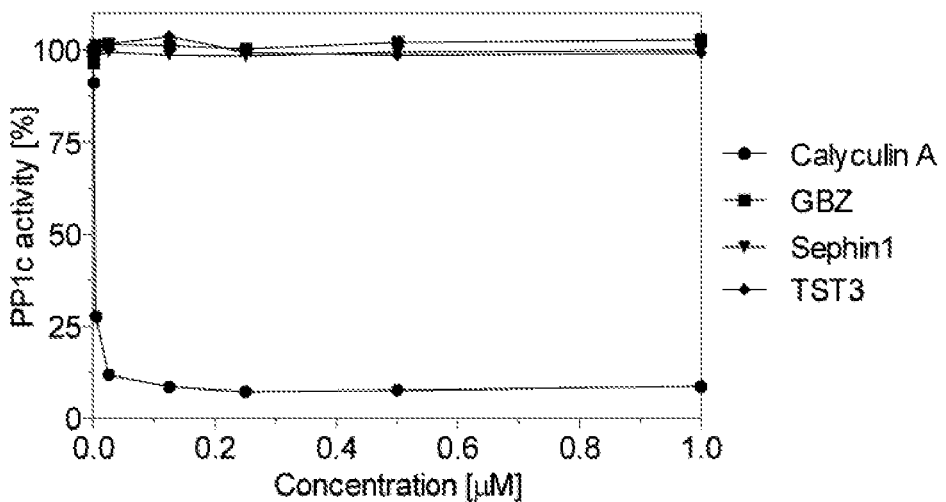
FIG. 25 shows the steady states affinities of different compounds to R15A-PP1c, R15B-PP1c and PP1c immobilized on SPR chips of the present invention.
Table showing GBZ, Sephin1 Sal003 and TST3 and their respective affinities ($K_D$) for the eIF2α holophospatases or PP1c alone. (--): No binding. Representative results of at least three independent experiments are shown in each panel. Data are means±SD, n=3. $K_D$ values were calculated with a steady-state affinity model by the Biacore T200 analysis software (Biaevaluation Version 1.0).
FIG. 26 In contrast to calyculin A, a catalytic inhibitor of PP1, TST3, like GBZ and Sephin1 does not inhibit PP1c FIG. 27 TST3 transiently induces eIF2α phosphorylation by selectively inhibiting R15B. Immunoblots of the indicated proteins in HeLa cells lysates treated with TST3 at 10 μM FIG. 28 TST3 transiently reduces protein synthesis because it selectively inhibits R15B but not R15A. Autoradiogram of newly synthesized proteins radiolabeled with $^{35}$S-methionine from HeLa cells lysates treated with TST3 at 10 µM for the indicated time. Lower panel: InstantBlue staining.

We also measured the binding affinities of Salubrinal (Sal003), a known inhibitor of both R15A and R15B and found that it binds R15A, R15B as well as PP1 (FIG. 23) with affinities >20 μM (FIG. 25).

Figure 27:
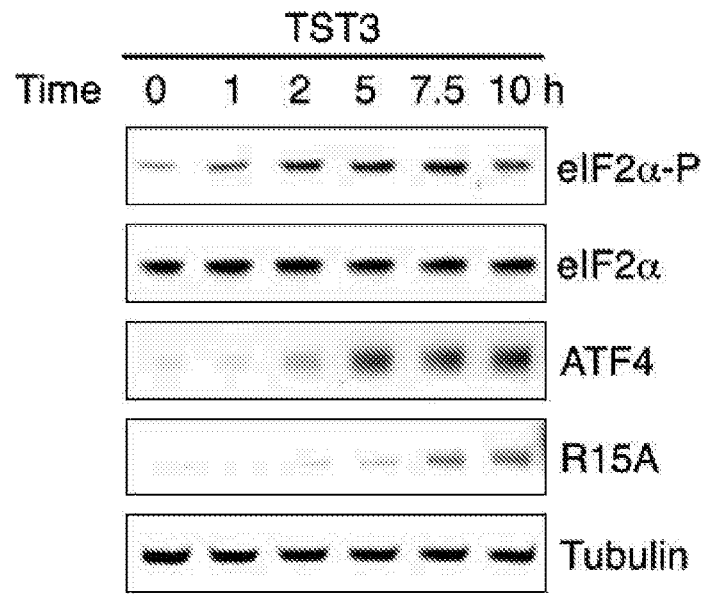
Figure 28:
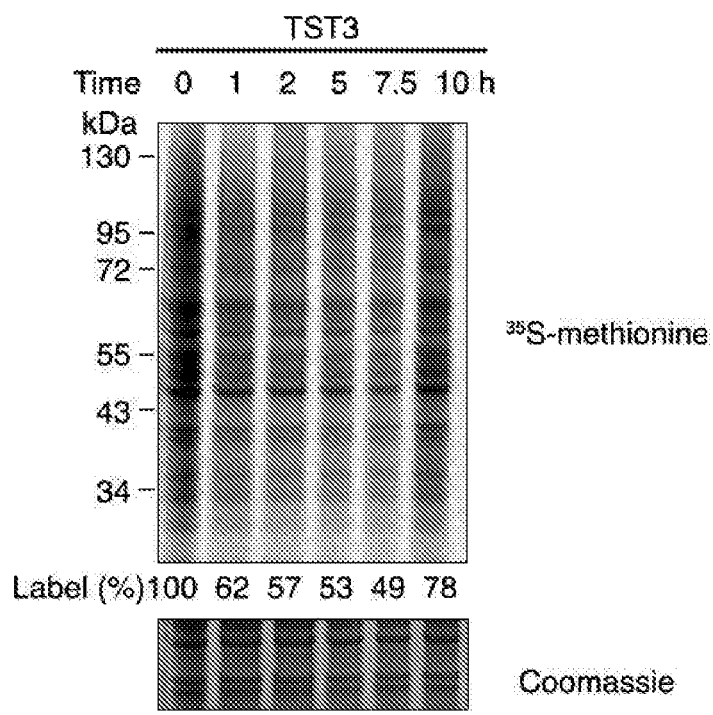
Figure 29:
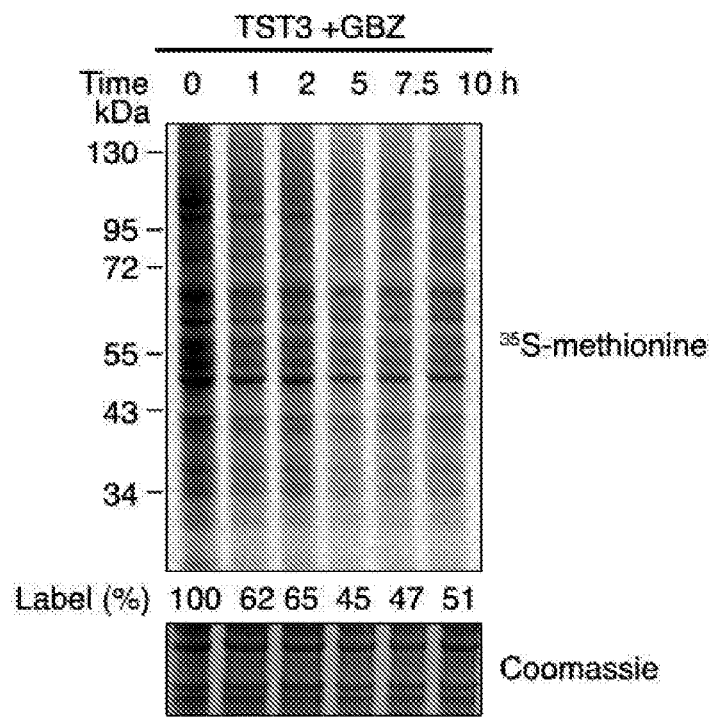
FIG. 29 TST3 persistently inhibits protein synthesis in the presence of GBZ. Autoradiogram of newly synthesized proteins radiolabeled with $^{35}$S-methionine from HeLa cells lysates treated with TST3+/− GBZ at 10 µM for the indicated time. Lower panel: InstantBlue staining.
Figure 30:
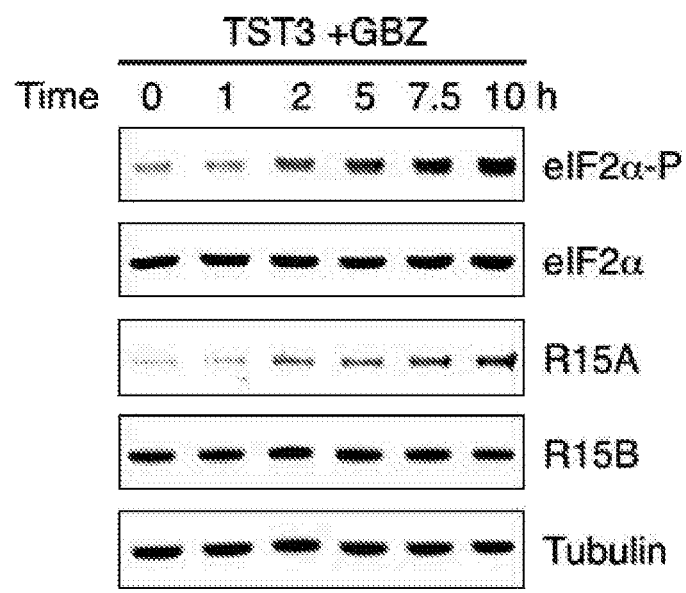
FIG. 30 TST3 persistently induces eIF2α phosphorylation in the presence of GBZ. Immunoblots of the indicated proteins in HeLa cells lysates treated with TST3+GBZ at 10 µM.

We next confirmed that TST3 doesn't inhibit PP1 in an enzymatic assay (FIG. 26) and then characterized it in cells. Under basal conditions, GBZ did not affect eIF2α phosphorylation or translation rates, as expected because PPP1R15A is not expressed without stress (5, 7). In contrast to GBZ, TST3 rapidly and transiently increased eIF2α phosphorylation (FIG. 27). Translation rates paralleled eIF2α phosphorylation and translation was rapidly and transiently decreased by TST3 (FIG. 28). Transcripts encoding ATF4 and R15A escape the general translation attenuation resulting from eIF2α phosphorylation (10, 11). TST3 induced expression of ATF4 and R15A (FIG. 27). Notably, R15A expression coincided with the translation recovery observed after 10 hours after TST3 addition (FIG. 27, 28). This suggests that R15A mediated eIF2α dephosphorylation and translation recovery in TST3-treated cell, implying that TST3 is a selective R15B-PP1c inhibitor.

Figure 31:
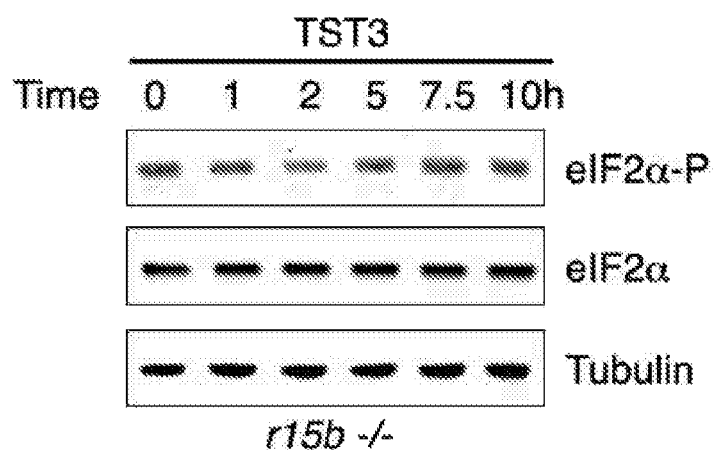
FIG. 31 TST3 activity is abolished in r15b knock out cells. Immunoblots of the indicated proteins in r15a$^{mut/mut}$ or r15b$^{mut/mut}$ MEFs lysates treated with TST3 at 10 µM for the indicated time.
Figure 32:
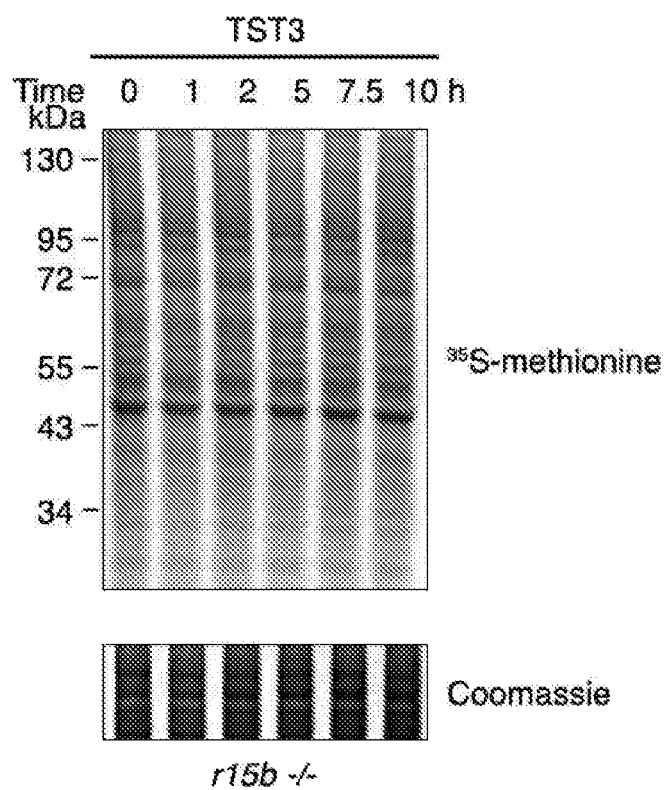
FIG. 32 TST3 has no effect on protein synthesis in r15B−/− cells. Upper panel: Autoradiogram of newly synthesized proteins radiolabeled with $^{35}$S-methionine from r15a$^{mut/mut}$ or r15b$^{mut/mut}$ MEFs lysates treated with TST3 at 10 µM for the indicated time.

If so, TST3 should provoke a persistent phosphorylation of eIF2α and a persistent inhibition of protein synthesis in absence of R15A. Indeed the TST3-induced eIF2α phosphorylation and translation attenuation were rendered persistent in the presence of the R15A inhibitor GBZ or upon generic inactivation of R15A. Importantly, all the measurable effects of TST3 on eIF2α phosphorylation and translation were abolished in r15b −/− cells (FIG. 31-32). This demonstrates that TST3 is a selective inhibitor of R15B. Selective inhibition of R15B provokes a transient phosphorylation of eIF2α and a transient attenuation of protein synthesis.

The combination of assays described here defines the activities of R15 inhibitors. As previously shown (7), a selective R15A inhibitor does not affect translation or eIF2α phosphorylation in unstressed cells. In contrast, we show here that a selective R15B inhibitor transiently induce eIF2α phosphorylation in absence of stress. It is so because R15A is induced by a selective R15B inhibitor. The combination of a R15A and a R15B inhibitor defines the activity of an R15A/B inhibitor: A R15A/B inhibitor induces a persistent inhibition of protein synthesis in cells. It also induces ATF4, confirming it's on-target effect.

Figure 33:
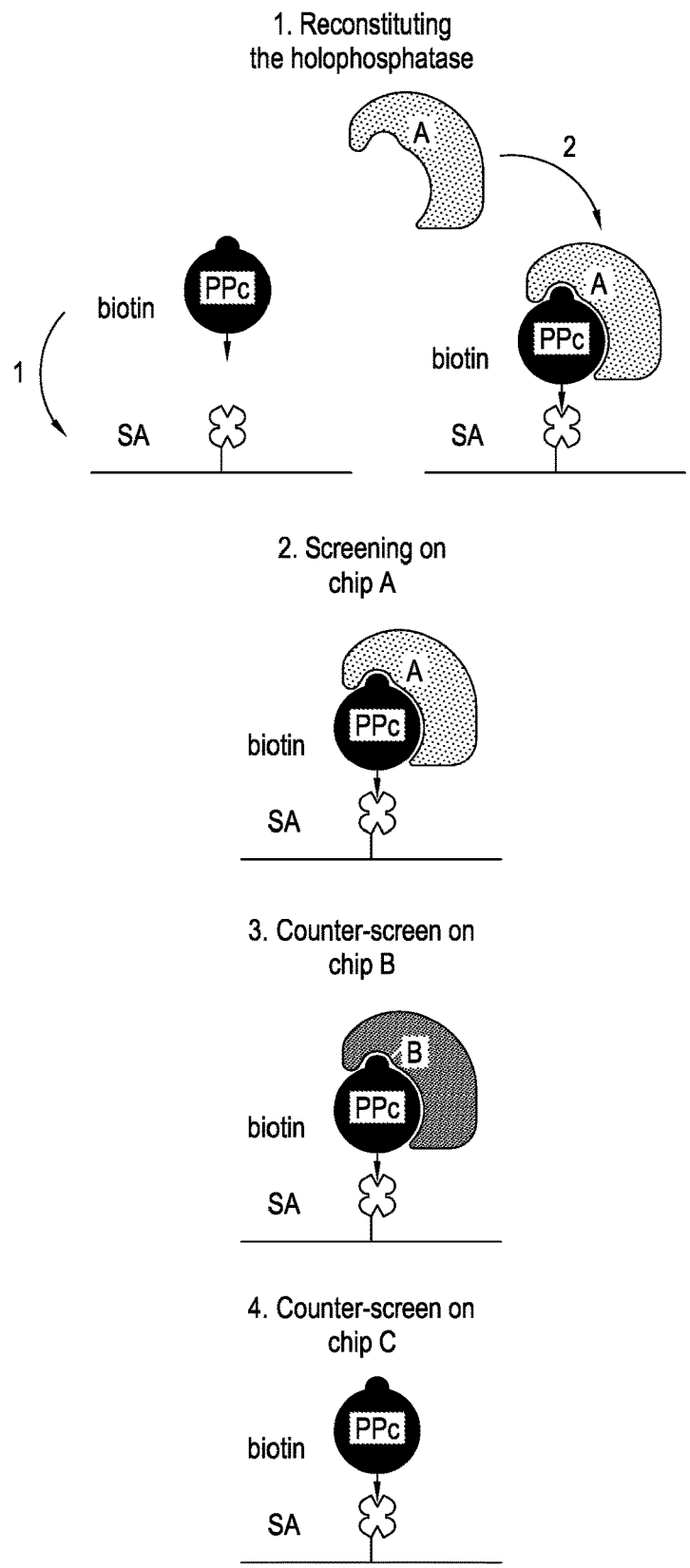
FIG. 33 is a schematic illustration of the format of an enzyme binding assay in which the catalytic subunit of the holophosphatase (PPc) is immobilised to a chip and is then bound to a regulatory subunit (A or B). Compounds can be tested for their ability to bind to chips having a different form of the holoenzyme bound (chips A or B).

Here, we have described a method that enabled the discovery of TST3, a selective inhibitor of the constitutive eIF2α phosphatase R15B and thereby demonstrated that rational drug discovery can be applied to intrinsically disordered regulatory subunits of phosphatases. Selective inhibition of R15B results in a transient attenuation of protein synthesis, a property that was exploited therapeutically to safely prevent HD in mice. Selective R15B inhibitors such as TST3 may be useful for the treatment of diverse diseases caused by misfolded proteins. Moreover, the method provided here is in principle generalizable to other phosphatases as well as intrinsically disordered proteins, creating new and broad opportunities for drug discovery. The method is summarized in a cartoon FIG. 33.

Materials and Methods
Protein Expression and Purification

MBP-R15A$^{325-636}$-His and MBP-R15B$^{340-698}$-His were expressed and purified as described before (Das et al. (2015) Science 348, 239-242) cDNA encoding for human PP1γ was cloned into the baculovirus transfer vector pDW464 to add a N-terminal biotin acceptor peptide (BAP). The vector also encodes for the E. coli biotin holoenzyme synthetase (BirA), so that BAP-tagged proteins can be biotinylated (bio-PP1c) in vivo in Spodoptere frugiperda (Sf9) insect cells (Duffy et al (1998) Anal. Biochem. 262, 122-128). The Bac-to-Bac baculovirus expression system (Thermo Fisher Scientific) was used to generate the recombinant bacmid DNA and Sf9 insect cells were used to amplify the viral stocks. The protein was produced using Sf9 insect cells in Insect-Xpress media (Lonza). bio-PP1 was purified by anion exchange chromotography on a HiTrap Q HP column (GE Healthcare), followed by gel filtration (HiLoad 16/600 Superdex 200 column, GE Healthcare). The proteins were analyzed on BOLT SDS-PAGE 4-12% Bis-Tris gels (Thermo Fisher Scientific) stained with InstantBlue (Expedeon) and the presence of a biotinylated PP1 was confirmed by a western blot using a Pierce High Sensitivity Streptavidin-HRP antibody (Thermo Fisher Scientific). This results in a partially pure protein, full purification is reached in later stages due to the high affinity and specificity of the biotin to streptavidin (on the SPR chip).

Binding of R15 to Bio-PP1c

Partially purified bio-PP1c (100 μl) was incubated on neutravidin agarose beads (Thermo Fisher Scientific) for 2 hours at 4° C. with shaking in IP buffer (50 mM Tris pH 7.5, 100 mM NaCl, 0.1 mM EGTA, 0.05% Tween 20, 0.1% NP40). The beads were then washed three times with the IP buffer and incubated in the presence or absence of 10 μM R15 (A or B) over night at 4° C. with shaking in IP buffer. The beads were then washed three times with IP buffer and bound proteins were eluted by boiling in 60 μl of Laemmli buffer. Bound proteins were then analyzed on BOLT SDS-PAGE 4-12% Bis-Tris gels (Thermo Fisher Scientific) stained with InstantBlue (Expedeon) the presence of a biotinylated PP1c was confirmed by a western blot using a Pierce High Sensitivity Streptavidin-HRP antibody (Thermo Fisher Scientific).

Surface Plasmon Resonance (SPR)
Capture of Bio-GBZ or Bio-PP1c on the SA Sensor Chip A Biacore T200 (GE Healthcare) system was used for all experiments and biotinylated GBZ (bio-GBZ) (Tsaylter 2011) or bio-PP1 was captured on a Sensor Chip SA (GE Healthcare). The streptavidin coated surface was activated by 1 minute injection with a solution of 50 mM NaOH and 1 M NaCl three times at a flow rate of 10 μl/min. bio-GBZ or bio-PP1c was diluted in the running buffer (50 mM Tris pH 7.5, 100 mM NaCl, 0.1 mM EGTA, 0.05% Tween 20, 0.1% DMSO) and injected at approximately 300 nM concentration at a flow rate of 10 μl/min directly to streptavidin coated surface to reach immobilization level of bio-GBZ or bio-PP1c corresponding to ~200 and 6000 RU, respectively. A blank immobilization was performed for one of the SA sensor chip surface to use as a reference.

Determining Steady-State Binding Constants of Small Molecules to R15 Holophosphatase Complexes Using the Bio-PP1c Surface With minor deviations, the same procedure and conditions were used in all binding experiments. Small molecules were stored as 50 mM stock solutions in 100% DMSO. Prior to determining binding constants, serial dilutions of either 12 or 8 concentrations of the compounds were prepared in the running buffer in a 96-well plate. Prior to each compound dilution series the regulatory subunit, MBP-R15A$^{325-636}$-His or MBP-R15B340-698-His, was diluted to 10 μM in the running buffer and captured on the bio-PP1c surface at a flow rate of 30 μl/min for 1 minute to form the holophosphatase complex on the sensor chip surface. This was followed by 1 minute stabilization period, to wash off any unspecific binding. Then, without regenerating the surface, the compound dilution series was injected onto the surface of the chip at a flow rate of 30 μl/min for 1 minute, followed by 2 minutes dissociation time. After each dilution series the surface was regenerated using 3 M NaCl for 90 seconds. After regeneration, SPR responses generally returned to base levels and the bio-PP1c surface was ready for the next compound dilution series. In order to be able to correct for small variations in DMSO concentration between samples, eight solvent samples ranging from 0.06 to 8% DMSO were injected every 50th cycle. The flow cell temperature was 10° C.

Data Analysis

Sensorgrams were analyzed using the Biacore T200 evaluation software and the binding constants determined based on a steady-state model. Kinetic experiments are carried out using different concentrations of the compound and their respective equilibrium binding levels determined. These equilibrium response levels ($R_{eq}$) are plotted against concentration and fitted using a global fit, which is able to determine steady-state affinity constants, i.e. the concentration at 50% saturation is $K_D$ (Frostell-Karlsson (2000) as above).

PP1c Catalytic Activity Assay

Purified PP1c (30 nM) was incubated in 50 mM Tris pH 7, 1.5 mM EGTA, 3 mM $MnCl_2$, 0.01% Brij-35, 0.15% β-mercaptoethanol with indicated concentrations of CalyculinA, GBZ, Sal003, Sephin1 and TST3 for 30 minutes at 4° C. Residual activity of PP1c was then measured using the EnzChek Phosphatase Assay Kit (Thermo Fisher Scientific) according to the supplier's instructions.

Mammalian Cell Culture

HeLa cells were maintained in Dulbecco's Modified Eagle's Media (DMEM) supplemented with penicillin, streptomycin, glutamine and 10% fetal bovine serum (FBS). Ppp1r15a −/− and Ppp1r15b −/− MEF cells were maintained in DMEM supplemented with penicillin, streptomycin, glutamine, 55 μM β-mercaptoethanol, 1X non-essential amino acids (Sigma) and 10% FBS.

Protein Analyses on Immunoblots

Cells (90,000 cells/ml) were plated in a 24-well plate and treated as indicated. At the end of treatment cells were lysed in 150 μl Laemmli Buffer. Lysates were boiled at 95° C. for 5 minutes, sonicated and resolved on 4-12% Bolt Bis-Tris Plus Gels (Thermo Fisher Scientific). Proteins were transferred to the nitrocellulose membrane using the iBlot 2 system (Thermo Fisher Scientific) and analysed using the following antibodies: e-IF2α-P (44-728G, Thermo Fisher Scientific, 1:1000), e-IF2α (ab5369, Abcam, 1:1000), tubulin (T5168, Sigma-Aldrich, 1:4000), BiP (610978, BD Biosciences Pharmingen, 1:1000), ATF4 (sc-200, Santa Cruz Biotechnology, 1:500), Ppp1r15a (10449-1-AP, Proteintech, 1:1000) and Ppp1r15b (14634-1-AP, Proteintech, 1:1000). Proteins were visualized using ECL Prime (GE Healthcare).

Assessment of Translation Rates

Cells (90,000 cells/ml) were plated in 12-well plates, treated as indicated, labelled with 100 μCi/ml $^{35}$S-methionine (Hartmann Analytic) for 10 minutes at 37° C., washed with ice-cold PBS and lysed in 120 μl Laemmli Buffer. Lysates were boiled at 95° C. for 5 minutes, sonicated and resolved on 4-12% Bolt Bis-Tris Plus Gels (Thermo Fisher Scientific). Gels were then stained with InstantBlue (Expedeon) and analyzed by phosphorimaging.

Animals

All animal care and procedures were performed in compliance with the regulation on the use of Animals in Research (UK Animals Scientific Procedures Act of 1986 and the EU Directive 2010/63/EU) with local ethical approval.

C57BL/6J male mice were obtained from The Jackson Laboratory or Charles River. HD-N171-82Q (HD) transgenic mice were obtained from The Jackson Laboratory and maintained in mixed background (C3H/B6).

All mice were housed in groups (2-3 per cage), in individually ventilated cages with ad libitum access to food and water and were maintained in 12 hour light/dark cycle (7 am-7 pm).

Pharmacological Treatments

The acetate salt of TST3 or GBZ was dissolved in water and sonicated for 10 minutes. The solution was aliquoted and kept at −20° C. until use. Once thawed a tube was kept at 4° C. and used within 24 hours.

TST3 or GBZ was administered by oral gavage at 2 mg/kg (unless otherwise specified). Mice received a single dose or were treated chronically—one time per day.

To produce an experimental group HD-N171-82Q transgenic males were crossed with C3H/B6 F1 wild type females. 4 weeks old transgenic males and their wild type littermate male controls were randomized in different groups and treated with TST3 for 4 weeks.

Pharmacokinetics Studies

Pharmacokinetics studies were performed by XenoGesis. TST3 was administrated orally in C57BL/6J males. Plasma samples were prepared by protein precipitation with methanol containing internal standards. Tissues were weighed and prepared by homogenisation (1:3 in phosphate buffered saline) and protein precipitated with methanol containing internal standard. Following the addition of methanol, plasma and tissue samples were placed at −20° C. for 1 hour (or overnight) to allow proteins to precipitate. The samples were then centrifuged at 2,500×g (3,400 rpm) for 20 minutes at 4° C. The supernatants were analysed by LC-MS/MS.

Rotarod

TST3 treatment of HD-N171-82Q transgenic males and their wild type littermate male controls started at 4 weeks of age and was continued for 4 weeks before the test. During the habituation phase mice were placed on a static rod for 1 minute and then trained for 1 minute at fixed speed 4 rpm. Habituation phase was repeated. Rotarod testing was performed in three trials. In each trial mice were allowed to run on an accelerating rod from 4 to 40 rpm for up to 300 seconds and the latency to fall was counted. Presented is the average of three trials.

Monitoring Motor Performance After Acute TST3 Administration

In order to assess the GBZ-like side effects (due to the adrenergic activity) of treatment the motor performance of mice was monitored after a single administration of TST3. To this end mice were treated with TST3 and left in a cage for 60 minutes. Mice behaviour was monitored every 15 minutes. Mice similarly treated with GBZ were used as a control.

Statistical Analysis

The comparisons were carried out using Student t-test or two-way analysis of variance (ANOVA). Significant differences are indicated in the corresponding figures.

Compound Synthesis

Synthetic Procedure:

To a suspension of 2,3-Dichlorobenzaldehyde (22.00 g, 0.12570 mol) and aminoguanidine bicarbonate (17.1 g, 0.12570 mol) in Methanol (220 ml) was added acetic acid (22 ml) at 25° C. The resulting reaction mixture was heated at 70° C. for next ~30 minutes. Upon heating the suspension became clear. Reaction completion was monitored on TLC using Dichloromethane/Methanol (8/2) as mobile phase. After completion of reaction, the reaction mixture was allowed to cool down to 25° C. and concentrated under vacuum. The resulting residue was suspended in diethyl ether (100 ml) and resulting product was collected by filtration. This process was repeated 3 times. At the end of the above process we could get the desired (E)-2-(2,3-dichlorobenzylidene)hydrazine-1-carboximidamide ("TST3"). LC-MS: m/z=231.23 (M+H). The resulting product was also analyzed by 1H-NMR, 13C-NMR, potentiometric titration, HPLC and CHN analysis.

REFERENCES

Boens, S., Szekér, K., Van Eynde, A., and Bollen, M. (2013). Interactor-guided dephosphorylation by protein phosphatase-1. Methods Mol. Biol. 1053, 271-281.

Bollen, M., Peti, W., Ragusa, M. J., and Beullens, M. (2010). The extended PP1 toolkit: designed to create specificity. Trends Biochem. Sci. 35,450-458.

Boyce, M., Bryant, K. F., Jousse, C., Long, K., Harding, H. P., Scheuner, D., Kaufman, R. J., Ma, D., Coen, D. M., Ron, D., et al. (2005). A selective inhibitor of eIF2alpha dephosphorylation protects cells from ER stress. Science 307, 935-939.

Chen, R., Rato, C., Yan, Y., Crespillo-Casado, A., Clarke, H. J., Harding, H. P., Marciniak, S. J., Read, R. J., Ron, D., and Nelson, W. J. (2015). G-actin provides substrate-specificity to eukaryotic initiation factor 2α holophosphatases. Science 4, e04871.

Choy, M. S., Page, R., and Peti, W. (2012a). Regulation of protein phosphatase 1 by intrinsically disordered proteins. Biochem. Soc. Trans. 40, 969-974.

Choy, M. S., Page, R., and Peti, W. (2012b). Regulation of protein phosphatase 1 by intrinsically disordered proteins. Biochem. Soc. Trans. 40, 969-974.

Choy, M. S., Hieke, M., Kumar, G. S., Lewis, G. R., Gonzalez-DeWhitt, K. R., Kessler, R. P., Stein, B. J., Hessenberger, M., Nairn, A. C., Peti, W., et al. (2014). Understanding the antagonism of retinoblastoma protein dephosphorylation by PNUTS provides insights into the PP1 regulatory code. Proceedings of the National Academy of Sciences 111, 4097-4102.

Choy, M. S., Yusoff, P., Lee, I. C., Newton, J. C., Goh, C. W., Page, R., Shenolikar, S., and Peti, W. (2015). Structural and Functional Analysis of the GADD34:PP1 eIF2α Phosphatase. Cell Reports.

Das, I., Krzyzosiak, A., Schneider, K., Wrabetz, L., D'Antonio, M., Barry, N., Sigurdardottir, A., and Bertolotti, A. (2015). Preventing proteostasis diseases by selective inhibition of a phosphatase regulatory subunit. Science 348, 239-242.

Gilmartin, A. G., Faitg, T. H., Richter, M., Groy, A., Seefeld, M. A., Darcy, M. G., Peng, X., Federowicz, K., Yang, J., Zhang, S. -Y., et al. (2014). Allosteric Wip1 phosphatase inhibition through flap-subdomain interaction. Nat Chem Biol 1-10.

Harding, H. P., Novoa, I., Zhang, Y., Zeng, H., Schapira, M., and Ron, D. (2000). Regulated translation initiation controls stress-induced gene expression in mammalian cells. Mol. Cell 6, 1099-1108.

Heroes, E., Lesage, B., Görnemann, J., Beullens, M., Van Meervelt, L., and Bollen, M. (2012). The PP1 binding code: a molecular-lego strategy that governs specificity. FEBS Journal 280, 584-595.

Jousse, C., Oyadomari, S., Novoa, I., Lu, P., Zhang, Y., Harding, H. P., and Ron, D. (2003). Inhibition of a constitutive translation initiation factor 2alpha phosphatase, CReP, promotes survival of stressed cells. The Journal of Cell Biology 163, 767-775.

Lee, Y. Y., Cevallos, R. C., and Jan, E. (2009). An upstream open reading frame regulates translation of GADD34 during cellular stresses that induce eIF2alpha phosphorylation. J. Biol. Chem. 284, 6661-6673.

Novoa, I., Zeng, H., Harding, H. P., and Ron, D. (2001). Feedback inhibition of the unfolded protein response by GADD34-mediated dephosphorylation of eIF2alpha. The Journal of Cell Biology 153, 1011-22.

Robert, F., Kapp, L. D., Khan, S. N., Acker, M. G., Kolitz, S., Kazemi, S., Kaufman, R. J., Merrick, W. C., Koromilas, A. E., Lorsch, J. R., et al. (2006). Initiation of protein synthesis by hepatitis C virus is refractory to reduced eIF2.GTP.Met-tRNA(i)(Met) ternary complex availability. Molecular Biology of the Cell 17, 4632-4644.

Tsaytler, P., and Bertolotti, A. (2013). Exploiting the selectivity of protein phosphatase 1 for pharmacological intervention. Febs J. 280, 766-770.

Tsaytler, P., Harding, H. P., Ron, D., and Bertolotti, A. (2011). Selective inhibition of a regulatory subunit of protein phosphatase 1 restores proteostasis. Science 332, 91-94.

Virshup, D. M., and Shenolikar, S. (2009). From promiscuity to precision: protein phosphatases get a makeover. Mol. Cell 33,537-545.

References for Example B

1. H. P. Harding, Y. Zhang, A. Bertolotti, H. Q. Zeng, D. Ron, Perk is essential for translational regulation and cell survival during the unfolded protein response. *Mol. Cell.* 5, 897-904 (2000).
2. D. Scheuner et al., Translational control is required for the unfolded protein response and in vivo glucose homeostasis. *Mol. Cell.* 7, 1165-1176 (2001).
3. H. P. Harding et al., An integrated stress response regulates amino acid metabolism and resistance to oxidative stress. *Mol. Cell.* 11, 619-633 (2003).
4. G. D. Pavitt, D. Ron, New Insights into Translational Regulation in the Endoplasmic Reticulum Unfolded Protein Response. *Cold Spring Harbor Perspectives in Biology.* 4, a012278-a012278 (2012).
5. I. Novoa, H. Zeng, H. P. Harding, D. Ron, Feedback inhibition of the unfolded protein response by GADD34-mediated dephosphorylation of eIF2alpha. *The Journal of Cell Biology.* 153, 1011-22. (2001).
6. C. Jousse et al., Inhibition of a constitutive translation initiation factor 2alpha phosphatase, CReP, promotes survival of stressed cells. *The Journal of Cell Biology.* 163, 767-775 (2003).
7. Tsaytler, H. P. Harding, D. Ron, A. Bertolotti, Selective inhibition of a regulatory subunit of protein phosphatase 1 restores proteostasis. *Science.* 332, 91-94 (2011).
8. I. Das et al., Preventing proteostasis diseases by selective inhibition of a phosphatase regulatory subunit. *Science.* 348, 239-242 (2015).
9. S. Boens, K. Szekér, A. Van Eynde, M. Bollen, Interactor-guided dephosphorylation by protein phosphatase-1. *Methods Mol. Biol.* 1053, 271-281 (2013).
10. H. P. Harding et al., Regulated translation initiation controls stress-induced gene expression in mammalian cells. *Mol. Cell.* 6, 1099-1108 (2000).
11. Y. Y. Lee, R. C. Cevallos, E. Jan, An upstream open reading frame regulates translation of GADD34 during cellular stresses that induce eIF2alpha phosphorylation. *J. Biol. Chem.* 284, 6661-6673 (2009).
12. H. P. Harding et al., Ppp1r15 gene knockout reveals an essential role for translation initiation factor 2 alpha (eIF2alpha) dephosphorylation in mammalian development. *Proc. Natl. Acad. Sci. U.S.A.* 106, 1832-1837 (2009).
13. B. Abdulkarim et al., A missense mutation in PPP1R15B causes a syndrome including diabetes, short stature and microcephaly. *Diabetes*, db150477 (2015).
14. S. Jazcilevich, S. Villa-Trevino, Induction of fatty liver in the rat after cycloheximide administration. *Lab. Invest.* 23, 590-594 (1970).
15. M. Costa-Mattioli et al., eIF2alpha phosphorylation bidirectionally regulates the switch from short- to long-term synaptic plasticity and memory. *Cell.* 129, 195-206 (2007).

16. E. T. Powers, R. I. Morimoto, A. Dillin, J. W. Kelly, W. E. Balch, Biological and chemical approaches to diseases of proteostasis deficiency. *Annu. Rev. Biochem.* 78, 959-991 (2009).

17. G. Schilling et al., Intranuclear inclusions and neuritic aggregates in transgenic mice expressing a mutant N-terminal fragment of huntingtin. *Hum. Mol. Genet.* 8, 397-407 (1999).

The invention claimed is:

1. A method of treating a subject having a polyglutamine disorder, wherein the method comprises administering to the subject a therapeutically effective amount of a PPP1R15B selective inhibitor, wherein the PPP1R15B selective inhibitor is (E)-2-(2,3-dichlorobenzylidene)hydrazine-1-carboximidamide- or a salt thereof.

2. A method as claimed in claim 1, wherein the polyglutamine disorder is chosen from Huntington's disease or an ataxia.

3. A method as claimed in claim 2, wherein the polyglutamine disorder is Huntington's disease.

4. A method of treating a subject having Parkinson's disease, wherein the method comprises administering to the subject a therapeutically effective amount of a PPP1R15B selective inhibitor, wherein the PPP1R15B selective inhibitor is (E)-2-(2,3-dichlorobenzylidene)hydrazine-1-carboximidamide, or a salt thereof.

5. A method of treating a subject having Alzheimer's disease, wherein the method comprises administering to the subject a therapeutically effective amount of a PPP1R15B selective inhibitor, wherein the PPP1R15B selective inhibitor is (E)-2-(2,3-dichlorobenzylidene)hydrazine-1-carboximidamide-or a salt thereof.

6. A method as claimed in claim 2, wherein the polyglutamine disorder is an ataxia.

* * * * *

UNITED STATES PATENT AND TRADEMARK OFFICE
CERTIFICATE OF CORRECTION

PATENT NO. : 11,364,211 B2
APPLICATION NO. : 15/564863
DATED : June 21, 2022
INVENTOR(S) : Anne Bertolotti et al.

It is certified that error appears in the above-identified patent and that said Letters Patent is hereby corrected as shown below:

In the Claims

In Claim 1, Column 51, Lines 28-29, replace "(E)-2-(2,3-dichlorobenzylidene)hydrazine-1-carboximidamide- or" with --(E)-2-(2,3-dichlorobenzylidene)hydrazine-1-carboximidamide or--.

In Claim 4, Column 52, Lines 25-26, replace "(E)-2-(2,3-dichlorobenzylidene)hydrazine-1-carboximidamide- or" with --(E)-2-(2,3-dichlorobenzylidene)hydrazine-1-carboximidamide or--.

In Claim 5, Column 52, Lines 31-32, replace "(E)-2-(2,3-dichlorobenzylidene)hydrazine-1-carboximidamide- or" with --(E)-2-(2,3-dichlorobenzylidene)hydrazine-1-carboximidamide or--.

Signed and Sealed this
Twenty-seventh Day of September, 2022

Katherine Kelly Vidal
*Director of the United States Patent and Trademark Office*

```
                           SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer sequence GAPDH (f)

<400> SEQUENCE: 1
accacagtcc atgccatcac                                                   20

<210> SEQ ID NO 2
<211> LENGTH: 20
<212> TYPE: DNA
<213> ORGANISM: Artificial Sequence
<220> FEATURE:
<223> OTHER INFORMATION: Primer sequence GAPDH (r)

<400> SEQUENCE: 2
tccaccaccc tgttgctgta                                                   20

<210> SEQ ID NO 3
<211> LENGTH: 20
<212> TYPE: DNA
<213> ORGANISM: Artificial Sequence
<220> FEATURE:
<223> OTHER INFORMATION: Primer sequence PPP1R15A (f)

<400> SEQUENCE: 3
cctcctgaaa cttggggact                                                   20

<210> SEQ ID NO 4
<211> LENGTH: 20
<212> TYPE: DNA
<213> ORGANISM: Artificial Sequence
<220> FEATURE:
<223> OTHER INFORMATION: Primer sequence PPP1R15A (r)

<400> SEQUENCE: 4
gctgtgatgt gggataagcg                                                   20

<210> SEQ ID NO 5
<211> LENGTH: 674
<212> TYPE: PRT
<213> ORGANISM: Homo sapiens
<220> FEATURE:
<223> OTHER INFORMATION: PR15A_HUMAN

<400> SEQUENCE: 5

Met Ala Pro Gly Gln Ala Pro His Gln Ala Thr Pro Trp Arg Asp Ala
1               5                   10                  15

His Pro Phe Phe Leu Leu Ser Pro Val Met Gly Leu Leu Ser Arg Ala
            20                  25                  30

Trp Ser Arg Leu Arg Gly Leu Gly Pro Leu Glu Pro Trp Leu Val Glu
        35                  40                  45

Ala Val Lys Gly Ala Ala Leu Val Glu Ala Gly Leu Glu Gly Glu Ala
    50                  55                  60

Arg Thr Pro Leu Ala Ile Pro His Thr Pro Trp Gly Arg Arg Pro Glu
```

```
                65                  70                  75                  80
Glu Glu Ala Glu Asp Ser Gly Gly Pro Gly Glu Asp Arg Glu Thr Leu
                    85                  90                  95
Gly Leu Lys Thr Ser Ser Leu Pro Glu Ala Trp Gly Leu Leu Asp
                100                 105                 110
Asp Asp Asp Gly Met Tyr Gly Arg Glu Ala Thr Ser Val Pro Arg
                115                 120                 125
Gly Gln Gly Ser Gln Phe Ala Asp Gly Gln Arg Ala Pro Leu Ser Pro
                130                 135                 140
Ser Leu Leu Ile Arg Thr Leu Gln Gly Ser Asp Lys Asn Pro Gly Glu
145                 150                 155                 160
Glu Lys Ala Glu Glu Gly Val Ala Glu Glu Gly Val Asn Lys
                165                 170                 175
Phe Ser Tyr Pro Pro Ser His Arg Glu Cys Cys Pro Ala Val Glu Glu
                180                 185                 190
Glu Asp Asp Glu Glu Ala Val Lys Lys Glu Ala His Arg Thr Ser Thr
                195                 200                 205
Ser Ala Leu Ser Pro Gly Ser Lys Pro Ser Thr Trp Val Ser Cys Pro
210                 215                 220
Gly Glu Glu Glu Asn Gln Ala Thr Glu Asp Lys Arg Thr Glu Arg Ser
225                 230                 235                 240
Lys Gly Ala Arg Lys Thr Ser Val Ser Pro Arg Ser Ser Gly Ser Asp
                245                 250                 255
Pro Arg Ser Trp Glu Tyr Arg Ser Gly Glu Ala Ser Glu Glu Lys Glu
                260                 265                 270
Glu Lys Ala His Lys Glu Thr Gly Lys Gly Glu Ala Ala Pro Gly Pro
                275                 280                 285
Gln Ser Ser Ala Pro Ala Gln Arg Pro Gln Leu Lys Ser Trp Trp Cys
                290                 295                 300
Gln Pro Ser Asp Glu Glu Glu Gly Glu Val Lys Ala Leu Gly Ala Ala
305                 310                 315                 320
Glu Lys Asp Gly Glu Ala Glu Cys Pro Pro Cys Ile Pro Pro Ser
                325                 330                 335
Ala Phe Leu Lys Ala Trp Val Tyr Trp Pro Gly Glu Asp Thr Glu Glu
                340                 345                 350
Glu Glu Asp Glu Glu Glu Asp Glu Asp Ser Asp Ser Gly Ser Asp Glu
                355                 360                 365
Glu Glu Gly Glu Ala Glu Ala Ser Ser Ser Thr Pro Ala Thr Gly Val
                370                 375                 380
Phe Leu Lys Ser Trp Val Tyr Gln Pro Gly Glu Asp Thr Glu Glu Glu
385                 390                 395                 400
Glu Asp Glu Asp Ser Asp Thr Gly Ser Ala Glu Asp Glu Arg Glu Ala
                405                 410                 415
Glu Thr Ser Ala Ser Thr Pro Pro Ala Ser Ala Phe Leu Lys Ala Trp
                420                 425                 430
Val Tyr Arg Pro Gly Glu Asp Thr Glu Glu Glu Glu Asp Glu Asp Val
                435                 440                 445
Asp Ser Glu Asp Lys Glu Asp Ser Glu Ala Ala Leu Gly Glu Ala
                450                 455                 460
Glu Ser Asp Pro His Pro Ser His Pro Asp Gln Arg Ala His Phe Arg
465                 470                 475                 480
Gly Trp Gly Tyr Arg Pro Gly Lys Glu Thr Glu Glu Glu Glu Ala Ala
                485                 490                 495
```

Glu Asp Trp Gly Glu Ala Glu Pro Cys Pro Phe Arg Val Ala Ile Tyr
             500                 505                 510

Val Pro Gly Glu Lys Pro Pro Pro Trp Ala Pro Pro Arg Leu Pro
             515                 520                 525

Leu Arg Leu Gln Arg Arg Leu Lys Arg Pro Glu Thr Pro Thr His Asp
530                 535                 540

Pro Asp Pro Glu Thr Pro Leu Lys Ala Arg Lys Val Arg Phe Ser Glu
545                 550                 555                 560

Lys Val Thr Val His Phe Leu Ala Val Trp Ala Gly Pro Ala Gln Ala
                 565                 570                 575

Ala Arg Gln Gly Pro Trp Glu Gln Leu Ala Arg Asp Arg Ser Arg Phe
             580                 585                 590

Ala Arg Arg Ile Thr Gln Ala Gln Glu Glu Leu Ser Pro Cys Leu Thr
             595                 600                 605

Pro Ala Ala Arg Ala Arg Ala Trp Ala Arg Leu Arg Asn Pro Pro Leu
             610                 615                 620

Ala Pro Ile Pro Ala Leu Thr Gln Thr Leu Pro Ser Ser Ser Val Pro
625                 630                 635                 640

Ser Ser Pro Val Gln Thr Thr Pro Leu Ser Gln Ala Val Ala Thr Pro
                 645                 650                 655

Ser Arg Ser Ser Ala Ala Ala Ala Ala Leu Asp Leu Ser Gly Arg
                 660                 665                 670

Arg Gly

<210> SEQ ID NO 6
<211> LENGTH: 713
<212> TYPE: PRT
<213> ORGANISM: Homo sapiens
<220> FEATURE:
<223> OTHER INFORMATION: PR15B_HUMAN

<400> SEQUENCE: 6

Met Glu Pro Gly Thr Gly Gly Ser Arg Lys Arg Leu Gly Pro Arg Ala
1                 5                  10                  15

Gly Phe Arg Phe Trp Pro Pro Phe Phe Pro Arg Arg Ser Gln Ala Gly
             20                  25                  30

Ser Ser Lys Phe Pro Thr Pro Leu Gly Pro Glu Asn Ser Gly Asn Pro
             35                  40                  45

Thr Leu Leu Ser Ser Ala Gln Pro Glu Thr Arg Val Ser Tyr Trp Thr
    50                  55                  60

Lys Leu Leu Ser Gln Leu Leu Ala Pro Leu Pro Gly Leu Leu Gln Lys
65                  70                  75                  80

Val Leu Ile Trp Ser Gln Leu Phe Gly Gly Met Phe Pro Thr Arg Trp
                 85                  90                  95

Leu Asp Phe Ala Gly Val Tyr Ser Ala Leu Arg Ala Leu Lys Gly Arg
             100                 105                 110

Glu Lys Pro Ala Ala Pro Thr Ala Gln Lys Ser Leu Ser Ser Leu Gln
             115                 120                 125

Leu Asp Ser Ser Asp Pro Ser Val Thr Ser Pro Leu Asp Trp Leu Glu
    130                 135                 140

Glu Gly Ile His Trp Gln Tyr Ser Pro Pro Asp Leu Lys Leu Glu Leu
145                 150                 155                 160

Lys Ala Lys Gly Ser Ala Leu Asp Pro Ala Ala Gln Ala Phe Leu Leu
                 165                 170                 175

```
Glu Gln Gln Leu Trp Gly Val Glu Leu Leu Pro Ser Ser Leu Gln Ser
            180                 185                 190

Arg Leu Tyr Ser Asn Arg Glu Leu Gly Ser Ser Pro Ser Gly Pro Leu
        195                 200                 205

Asn Ile Gln Arg Ile Asp Asn Phe Ser Val Val Ser Tyr Leu Leu Asn
        210                 215                 220

Pro Ser Tyr Leu Asp Cys Phe Pro Arg Leu Glu Val Ser Tyr Gln Asn
225                 230                 235                 240

Ser Asp Gly Asn Ser Glu Val Val Gly Phe Gln Thr Leu Thr Pro Glu
                245                 250                 255

Ser Ser Cys Leu Arg Glu Asp His Cys His Pro Gln Pro Leu Ser Ala
            260                 265                 270

Glu Leu Ile Pro Ala Ser Trp Gln Gly Cys Pro Pro Leu Ser Thr Glu
            275                 280                 285

Gly Leu Pro Glu Ile His His Leu Arg Met Lys Arg Leu Glu Phe Leu
            290                 295                 300

Gln Gln Ala Asn Lys Gly Gln Asp Leu Pro Thr Pro Asp Gln Asp Asn
305                 310                 315                 320

Gly Tyr His Ser Leu Glu Glu Glu His Ser Leu Leu Arg Met Asp Pro
                325                 330                 335

Lys His Cys Arg Asp Asn Pro Thr Gln Phe Val Pro Ala Ala Gly Asp
            340                 345                 350

Ile Pro Gly Asn Thr Gln Glu Ser Thr Glu Glu Lys Ile Glu Leu Leu
            355                 360                 365

Thr Thr Glu Val Pro Leu Ala Leu Glu Glu Ser Pro Ser Glu Gly
            370                 375                 380

Cys Pro Ser Ser Glu Ile Pro Met Glu Lys Glu Pro Gly Glu Gly Arg
385                 390                 395                 400

Ile Ser Val Val Asp Tyr Ser Tyr Leu Glu Gly Asp Leu Pro Ile Ser
                405                 410                 415

Ala Arg Pro Ala Cys Ser Asn Lys Leu Ile Asp Tyr Ile Leu Gly Gly
            420                 425                 430

Ala Ser Ser Asp Leu Glu Thr Ser Ser Asp Pro Glu Gly Glu Asp Trp
            435                 440                 445

Asp Glu Glu Ala Glu Asp Gly Phe Asp Ser Asp Ser Ser Leu Ser
450                 455                 460

Asp Ser Asp Leu Glu Gln Asp Pro Glu Gly Leu His Leu Trp Asn Ser
465                 470                 475                 480

Phe Cys Ser Val Asp Pro Tyr Asn Pro Gln Asn Phe Thr Ala Thr Ile
                485                 490                 495

Gln Thr Ala Ala Arg Ile Val Pro Glu Glu Pro Ser Asp Ser Glu Lys
            500                 505                 510

Asp Leu Ser Gly Lys Ser Asp Leu Glu Asn Ser Ser Gln Ser Gly Ser
            515                 520                 525

Leu Pro Glu Thr Pro Glu His Ser Ser Gly Glu Glu Asp Asp Trp Glu
            530                 535                 540

Ser Ser Ala Asp Glu Ala Glu Ser Leu Lys Leu Trp Asn Ser Phe Cys
545                 550                 555                 560

Asn Ser Asp Asp Pro Tyr Asn Pro Leu Asn Phe Lys Ala Pro Phe Gln
                565                 570                 575

Thr Ser Gly Glu Asn Glu Lys Gly Cys Arg Asp Ser Lys Thr Pro Ser
            580                 585                 590

Glu Ser Ile Val Ala Ile Ser Glu Cys His Thr Leu Leu Ser Cys Lys
```

-continued

```
                595                 600                 605
Val Gln Leu Leu Gly Ser Gln Glu Ser Glu Cys Pro Asp Ser Val Gln
    610                 615                 620

Arg Asp Val Leu Ser Gly Gly Arg His Thr His Val Lys Arg Lys Lys
625                 630                 635                 640

Val Thr Phe Leu Glu Glu Val Thr Glu Tyr Tyr Ile Ser Gly Asp Glu
                645                 650                 655

Asp Arg Lys Gly Pro Trp Glu Glu Phe Ala Arg Asp Gly Cys Arg Phe
            660                 665                 670

Gln Lys Arg Ile Gln Glu Thr Glu Asp Ala Ile Gly Tyr Cys Leu Thr
            675                 680                 685

Phe Glu His Arg Glu Arg Met Phe Asn Arg Leu Gln Gly Thr Cys Phe
            690                 695                 700

Lys Gly Leu Asn Val Leu Lys Gln Cys
705                 710
```